United States Patent
Brunner-Schwarz et al.

(10) Patent No.: US 12,303,598 B2
(45) Date of Patent: May 20, 2025

(54) PHARMACEUTICAL COMPOSITION COMPRISING A GLP-1-AGONIST AND METHIONINE

(71) Applicant: Sanofi-Aventis Deutschland GmbH, Frankfurt (DE)

(72) Inventors: Anette Brunner-Schwarz, Frankfurt (DE); Werner Mueller, Frankfurt (DE); Verena Siefke-Henzler, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 290 days.

(21) Appl. No.: 17/747,723

(22) Filed: May 18, 2022

(65) Prior Publication Data

US 2023/0028647 A1 Jan. 26, 2023

Related U.S. Application Data

(63) Continuation of application No. 16/921,422, filed on Jul. 6, 2020, now abandoned, which is a continuation of application No. 16/013,617, filed on Jun. 20, 2018, now abandoned, which is a continuation of application No. 15/595,929, filed on May 15, 2017, now Pat. No. 10,028,910, which is a continuation of application No. 13/509,507, filed as application No. PCT/EP2010/067249 on Nov. 11, 2010, now Pat. No. 9,707,176.

(30) Foreign Application Priority Data

Nov. 13, 2009 (DE) .......................... 102009052832.6
Mar. 18, 2010 (DE) .......................... 102010011919.9

(51) Int. Cl.
A61K 38/26 (2006.01)
A61K 9/00 (2006.01)
A61K 9/08 (2006.01)
A61K 38/22 (2006.01)
A61K 47/10 (2017.01)
A61K 47/20 (2006.01)
A61P 3/10 (2006.01)

(52) U.S. Cl.
CPC .............. *A61K 9/08* (2013.01); *A61K 9/0019* (2013.01); *A61K 38/2278* (2013.01); *A61K 38/26* (2013.01); *A61K 47/10* (2013.01); *A61K 47/20* (2013.01); *A61P 3/10* (2018.01)

(58) Field of Classification Search
CPC ...... A61K 38/26; A61K 38/2278; A61K 9/08; A61K 9/0019

See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 4,153,689 A | 5/1979 | Hirai et al. |
| 4,165,370 A | 8/1979 | Coval |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Dorschug et al. |
| 5,177,058 A | 1/1993 | Dorschug |
| 5,187,177 A | 2/1993 | Garzaran |
| 5,227,293 A | 7/1993 | Stengelin et al. |
| 5,253,785 A | 10/1993 | Haber et al. |
| 5,272,135 A | 12/1993 | Takruri |
| 5,358,708 A | 10/1994 | Patel |
| 5,358,857 A | 10/1994 | Stengelin et al. |
| 5,370,629 A | 12/1994 | Michel et al. |

(Continued)

FOREIGN PATENT DOCUMENTS

| | | |
|---|---|---|
| AU | 593274 B2 | 2/1990 |
| AU | 612324 B2 | 7/1991 |

(Continued)

OTHER PUBLICATIONS

"Buffer" Oxford Dictionary of Biochemistry and Molecular Biology, Oxford University Press, 2001, p. 83.
"Insulin Aspart Injection." Formulated Preparations: Specific Monographs. British Pharmacopoeia 3. pp. 1-3 (2012).
"Preferable." Merriam-Webster.com. Merriam-Webster, n.d. Web. Sep. 7, 2015. http://www.merriamwebster.com/dictionary/preferable).
"Suspension" Stedman's Medical Dictionary, 20th Edition, p. 1450 (Williams & Wilkins Co., Baltimore 1961).

(Continued)

*Primary Examiner* — Gyan Chandra
(74) *Attorney, Agent, or Firm* — Lathrop GPM LLP; James V. DeGiulio

(57) ABSTRACT

A liquid composition comprising a GLP-1 agonist or/and a pharmacologically tolerable salt thereof and, optionally, at least one pharmaceutically acceptable excipient, wherein the composition comprises methionine, as add-on therapy with metformin and/or with long-acting insulin/insulin derivates where appropriate.

6 Claims, 6 Drawing Sheets

Figure 1:
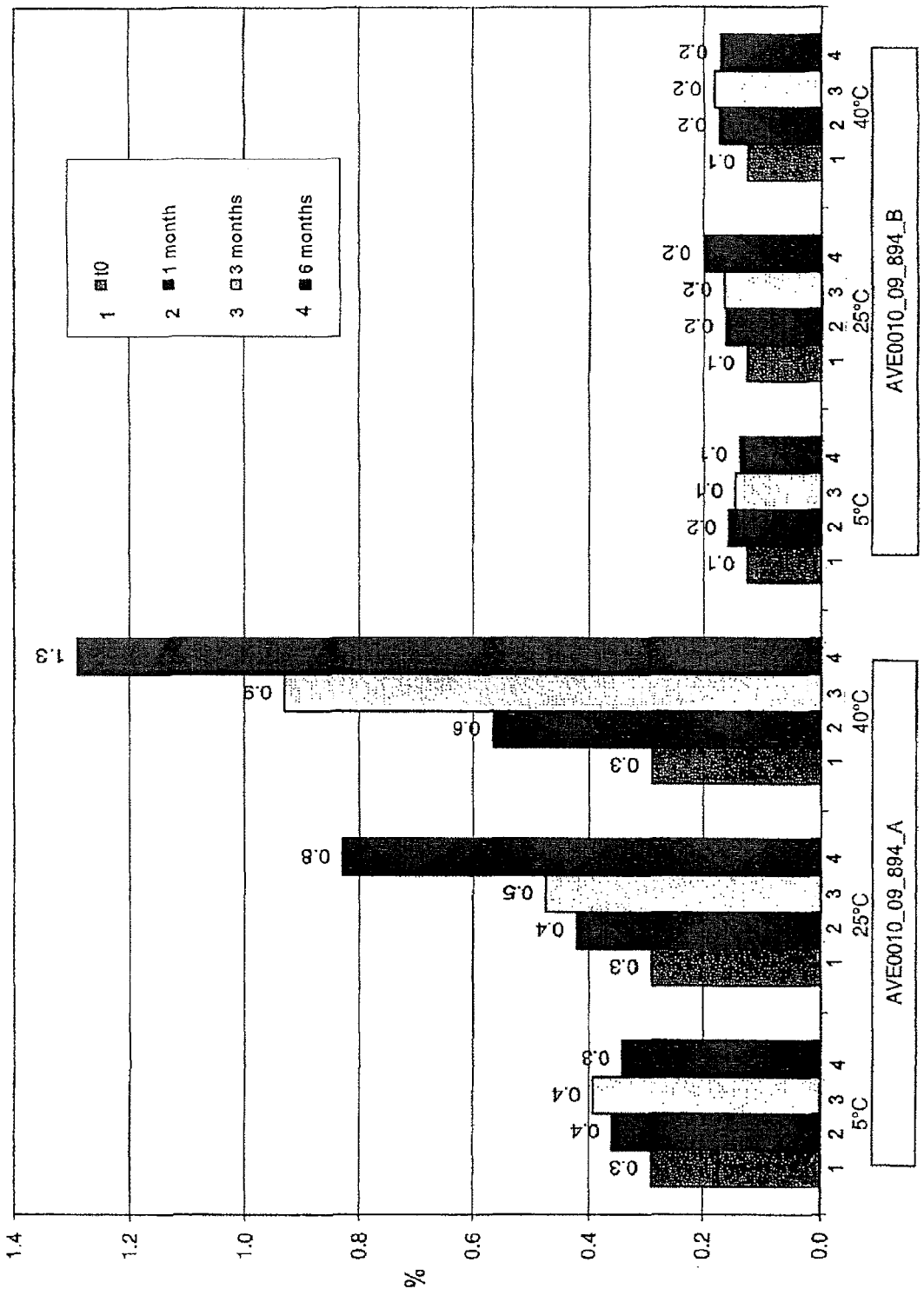

Specification includes a Sequence Listing.

(56) References Cited

U.S. PATENT DOCUMENTS

| | | |
|---|---|---|
| 5,397,771 A | 3/1995 | Bechgaard et al. |
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |
| 5,478,323 A | 12/1995 | Westwood et al. |
| 5,496,924 A | 3/1996 | Habermann et al. |
| 5,506,203 A | 4/1996 | Backstrom et al. |
| 5,509,905 A | 4/1996 | Michel et al. |
| 5,514,646 A | 5/1996 | Chance et al. |
| 5,524,286 A | 6/1996 | Chiesa et al. |
| 5,534,488 A | 7/1996 | Hoffmann |
| 5,545,618 A | 8/1996 | Buckley et al. |
| 5,547,929 A | 8/1996 | Anderson, Jr. et al. |
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Doerschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,935,566 A | 8/1999 | Yuen et al. |
| 5,948,751 A | 9/1999 | Kimer et al. |
| 5,952,297 A | 9/1999 | De et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | Defelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Doerschug |
| 6,110,703 A | 8/2000 | Egel-Mitani et al. |
| 6,174,856 B1 | 1/2001 | Langballe et al. |
| 6,191,102 B1 | 2/2001 | Dimarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | Desimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,410,511 B2 | 6/2002 | L'Italien et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,737,401 B2 | 5/2004 | Kim et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Doerschug et al. |
| 6,902,744 B1 | 6/2005 | Kolterman et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | Defelippis et al. |
| 7,115,563 B2 | 10/2006 | Younis et al. |
| 7,119,086 B2 | 10/2006 | Di et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | Defelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 9,526,764 B2 | 12/2016 | Werner |
| 9,707,176 B2 | 7/2017 | Brunner-Schwarz |
| 9,821,032 B2 | 11/2017 | Niemoller |
| 10,028,910 B2 | 7/2018 | Brunner-Schwarz |
| 10,029,011 B2 | 7/2018 | Hagendorf et al. |
| 10,117,909 B2 | 11/2018 | Werner |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | Defelippis et al. |
| 2003/0170691 A1 | 9/2003 | Gimeno et al. |
| 2003/0212248 A1 | 11/2003 | Furman |
| 2004/0022792 A1 | 2/2004 | Klinke |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | Defelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |

(56) References Cited

U.S. PATENT DOCUMENTS

| | | |
|---|---|---|
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0104210 A1 | 4/2009 | Tota et al. |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0048468 A1* | 2/2010 | Gegg, Jr. .................. A61P 3/08 530/324 |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2013/0317477 A1 | 11/2013 | Edwards et al. |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |
| 2016/0199452 A1 | 7/2016 | Souhami et al. |
| 2016/0235818 A1 | 8/2016 | Bergmann et al. |
| 2016/0287674 A1 | 10/2016 | Roy et al. |
| 2016/0296601 A1 | 10/2016 | Belder et al. |
| 2016/0354445 A1 | 12/2016 | Hess et al. |
| 2017/0080057 A1 | 3/2017 | Silvestre et al. |
| 2017/0119852 A1 | 5/2017 | Boka et al. |
| 2017/0136094 A1 | 5/2017 | Silvestre et al. |
| 2017/0143801 A1 | 5/2017 | Niemoller |
| 2017/0281733 A1 | 10/2017 | Werner et al. |
| 2017/0326069 A1 | 11/2017 | Brunner-Schwarz et al. |
| 2018/0000902 A1 | 1/2018 | Boka et al. |
| 2018/0092965 A1 | 4/2018 | Roy et al. |
| 2018/0133290 A1 | 5/2018 | Souhami et al. |
| 2018/0200370 A1 | 7/2018 | Hagendorf |
| 2019/0142747 A1 | 5/2019 | Brunner-Schwarz |
| 2019/0192635 A1 | 6/2019 | Werner |
| 2020/0188516 A1 | 6/2020 | Hagendorf |
| 2021/0038514 A1 | 2/2021 | Brunner-Schwarz |
| 2022/0016217 A1 | 1/2022 | Werner |
| 2022/0133890 A1 | 5/2022 | Hagendorf |
| 2023/0028647 A1 | 1/2023 | Brunner-Schwarz |
| 2024/0108692 A1 | 4/2024 | Werner |

FOREIGN PATENT DOCUMENTS

| | | | |
|---|---|---|---|
| AU | 200072263 A1 | 2/2001 | |
| CA | 1173388 A | 8/1984 | |
| CA | 1258427 A | 8/1989 | |
| CA | 1336329 C | 7/1995 | |
| CA | 1341203 C | 3/2001 | |
| CA | 2662084 A1 | 3/2008 | |
| CA | 2685638 A1 | 5/2011 | |
| CN | 1276731 A | 12/2000 | |
| CN | 1413582 A | 4/2003 | |
| CN | 1662252 A | 8/2005 | |
| CN | 101366692 A | 2/2009 | |
| CN | 101444618 A | 6/2009 | |
| CN | 101454019 A | 6/2009 | |
| CN | 101670096 A | 3/2010 | |
| DE | 2219635 A1 | 11/1972 | |
| DE | 3240177 A1 | 5/1983 | |
| DE | 19637230 A1 | 3/1998 | |
| DE | 102008003566 A1 | 7/2009 | |
| DE | 102008003568 A1 | 7/2009 | |
| DE | 102008051834 A1 * | 4/2010 | ............ A61K 38/26 |
| DE | 102008053048 A1 | 4/2010 | |
| EA | 006019 B1 | 8/2005 | |
| EP | 0018609 B1 | 9/1983 | |
| EP | 0046979 B1 | 9/1983 | |
| EP | 0132769 A1 | 2/1985 | |
| EP | 0140084 A1 | 5/1985 | |
| EP | 0166529 A1 | 1/1986 | |
| EP | 0180920 A2 | 5/1986 | |
| EP | 0200383 A2 | 11/1986 | |
| EP | 0211299 A2 | 2/1987 | |
| EP | 0214826 A2 | 3/1987 | |
| EP | 0224885 A1 | 6/1987 | |
| EP | 0227938 A2 | 7/1987 | |
| EP | 0229956 A1 | 7/1987 | |
| EP | 0229998 A2 | 7/1987 | |
| EP | 0254516 A2 | 1/1988 | |
| EP | 0305760 A2 | 3/1989 | |
| EP | 0368187 A2 | 5/1990 | |
| EP | 0375437 A2 | 6/1990 | |
| EP | 0383472 A2 | 8/1990 | |
| EP | 0194864 B1 | 6/1992 | |
| EP | 0419504 A1 | 1/1994 | |
| EP | 0600372 A1 | 6/1994 | |
| EP | 0668282 A1 | 8/1995 | |
| EP | 0668292 A2 | 8/1995 | |
| EP | 0678522 A1 | 10/1995 | |
| EP | 0837072 A2 | 4/1998 | |
| EP | 0845265 A1 | 6/1998 | |
| EP | 0885961 A1 | 12/1998 | |
| EP | 1076066 A1 | 2/2001 | |

(56) References Cited

FOREIGN PATENT DOCUMENTS

| | | |
|---|---|---|
| EP | 1172114 A2 | 1/2002 |
| EP | 1196444 A1 | 4/2002 |
| EP | 1222207 A1 | 7/2002 |
| EP | 1523993 A1 | 4/2005 |
| EP | 1364029 B1 | 12/2005 |
| EP | 1906991 A2 | 4/2008 |
| EP | 2112161 A2 | 10/2009 |
| EP | 2187950 A1 | 5/2010 |
| EP | 2324853 A1 | 5/2011 |
| EP | 2329848 A1 | 6/2011 |
| EP | 2389945 A1 | 11/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61-212598 A | 9/1986 |
| JP | S63-99096 A | 4/1988 |
| JP | H02-218696 A | 8/1990 |
| JP | 2-264798 A | 10/1990 |
| JP | H03-504240 A | 9/1991 |
| JP | H06-506444 A | 7/1994 |
| JP | 2001-521004 A | 11/2001 |
| JP | 2002-516880 A | 6/2002 |
| JP | 2003-505347 A | 2/2003 |
| JP | 2005-508895 A | 4/2005 |
| JP | 2005-532365 A | 10/2005 |
| JP | 2006-515267 A | 5/2006 |
| JP | 2006-137678 A | 6/2006 |
| JP | 2007-204498 A | 8/2007 |
| JP | 2009-091363 A | 4/2009 |
| JP | 2009-519961 A | 5/2009 |
| JP | 2012-505852 A | 3/2012 |
| JP | 2012-255040 A | 12/2012 |
| RU | 2008116057 A | 10/2009 |
| RU | 2386631 C2 | 4/2010 |
| TW | 157005 B | 5/1991 |
| TW | 562806 B | 11/2003 |
| WO | WO 1983/000288 A1 | 2/1983 |
| WO | WO 1988/006599 A1 | 9/1988 |
| WO | WO 1989/010937 A1 | 11/1989 |
| WO | WO 1990/007522 A1 | 7/1990 |
| WO | WO 1990/011299 A1 | 10/1990 |
| WO | WO 1991/003550 A1 | 3/1991 |
| WO | WO 1991/016929 A1 | 11/1991 |
| WO | WO 1992/000321 A1 | 1/1992 |
| WO | WO 1992/012999 A1 | 8/1992 |
| WO | WO 1993/018786 A1 | 9/1993 |
| WO | WO 1994/014461 A1 | 7/1994 |
| WO | WO 1995/000550 A1 | 1/1995 |
| WO | WO 1995/024183 A1 | 9/1995 |
| WO | WO 1996/004307 A1 | 2/1996 |
| WO | WO 1996/007399 A1 | 3/1996 |
| WO | WO 1996/011705 A1 | 4/1996 |
| WO | WO 1996/032414 A1 | 10/1996 |
| WO | WO 1996/034882 A1 | 11/1996 |
| WO | WO 1996/041606 A2 | 12/1996 |
| WO | WO 1997/001331 A2 | 1/1997 |
| WO | WO 1997/048413 A1 | 12/1997 |
| WO | WO 1998/005351 A1 | 2/1998 |
| WO | WO 1998/008531 A1 | 3/1998 |
| WO | WO 1998/008871 A1 | 3/1998 |
| WO | WO 1998/008873 A1 | 3/1998 |
| WO | WO 1998/019698 A1 | 5/1998 |
| WO | WO 1998/030231 A1 | 7/1998 |
| WO | WO 1998/035033 A1 | 8/1998 |
| WO | WO 1998/039022 A1 | 9/1998 |
| WO | WO 1998/042749 A1 | 10/1998 |
| WO | WO 1998/056406 A1 | 12/1998 |
| WO | WO 1998/056418 A1 | 12/1998 |
| WO | WO 1999/007404 A1 | 2/1999 |
| WO | WO 1999/021573 A1 | 5/1999 |
| WO | WO 1999/021578 A1 | 5/1999 |
| WO | WO 1999/024071 A1 | 5/1999 |
| WO | WO 1999/025727 A2 | 5/1999 |
| WO | WO 1999/025728 A1 | 5/1999 |
| WO | WO 1999/040788 A1 | 8/1999 |
| WO | WO 1999/043708 A1 | 9/1999 |
| WO | WO 1999/046283 A1 | 9/1999 |
| WO | WO 1999/062558 A1 | 12/1999 |
| WO | WO 2000/023098 A1 | 4/2000 |
| WO | WO 2000/023099 A1 | 4/2000 |
| WO | WO 2000/029013 A1 | 5/2000 |
| WO | WO 2000/041546 A2 | 7/2000 |
| WO | WO 2000/066629 A1 | 11/2000 |
| WO | WO 2000/074736 A1 | 12/2000 |
| WO | WO 2001/000223 A2 | 1/2001 |
| WO | WO 2001/002039 A1 | 1/2001 |
| WO | WO 2001/004156 A1 | 1/2001 |
| WO | WO 2001/012155 A1 | 2/2001 |
| WO | WO 2001/021154 A2 | 3/2001 |
| WO | WO 2001/024814 A1 | 4/2001 |
| WO | WO 2001/024826 A2 | 4/2001 |
| WO | WO 2001/025278 A1 | 4/2001 |
| WO | WO 2001/028555 A1 | 4/2001 |
| WO | WO 2001/032157 A2 | 5/2001 |
| WO | WO 2001/037808 A1 | 5/2001 |
| WO | WO 2001/043762 A2 | 6/2001 |
| WO | WO 2001/051071 A2 | 7/2001 |
| WO | WO 2001/052937 A1 | 7/2001 |
| WO | WO 2001/093837 A2 | 12/2001 |
| WO | WO 2002/000243 A2 | 1/2002 |
| WO | WO 2002/014823 A1 | 2/2002 |
| WO | WO 2002/024214 A2 | 3/2002 |
| WO | WO 2002/064115 A1 | 8/2002 |
| WO | WO 2002/065985 A2 | 8/2002 |
| WO | WO 2002/066628 A2 | 8/2002 |
| WO | WO 2002/068660 A1 | 9/2002 |
| WO | WO 2002/070722 A1 | 9/2002 |
| WO | WO 2002/076495 A1 | 10/2002 |
| WO | WO 2002/079250 A1 | 10/2002 |
| WO | WO 2003/002021 A2 | 1/2003 |
| WO | WO 2003/020201 A2 | 3/2003 |
| WO | WO 2003/032923 | 4/2003 |
| WO | WO 2003/035028 A1 | 5/2003 |
| WO | WO 2003/035051 A2 | 5/2003 |
| WO | WO 2003/035099 | 5/2003 |
| WO | WO 2003/044210 A2 | 5/2003 |
| WO | WO 2003/053339 A2 | 7/2003 |
| WO | WO 2003/066084 A1 | 8/2003 |
| WO | WO 2003/094951 A1 | 11/2003 |
| WO | WO 2003/094956 A1 | 11/2003 |
| WO | WO 2003/097812 A2 | 11/2003 |
| WO | WO 2003/101395 A2 | 12/2003 |
| WO | WO 2003/105888 A1 | 12/2003 |
| WO | WO 2004/005342 A1 | 1/2004 |
| WO | WO-2004035623 A2 * | 4/2004 ................ A61P 1/00 |
| WO | WO 2004/045592 A2 | 6/2004 |
| WO | WO 2004/064862 A1 | 8/2004 |
| WO | WO 2004/078196 A1 | 9/2004 |
| WO | WO 2004/078197 A1 | 9/2004 |
| WO | WO 2004/078198 A1 | 9/2004 |
| WO | WO 2004/080480 A1 | 9/2004 |
| WO | WO 2004/096854 A2 | 11/2004 |
| WO | WO 2004/105781 A2 | 12/2004 |
| WO | WO 2004/107979 A1 | 12/2004 |
| WO | WO 2005/021022 A2 | 3/2005 |
| WO | WO 2005/023291 A2 | 3/2005 |
| WO | WO 2005/028516 A2 | 3/2005 |
| WO | WO 2005/046716 A1 | 5/2005 |
| WO | WO 2004/050115 A2 | 6/2005 |
| WO | WO 2005/048950 A2 | 6/2005 |
| WO | WO 2005/112949 A1 | 12/2005 |
| WO | WO 2005/117948 A1 | 12/2005 |
| WO | WO 2006/000567 A1 | 1/2006 |
| WO | WO 2006/015879 A1 | 2/2006 |
| WO | WO 2006/029634 A2 | 3/2006 |
| WO | WO 2006/051103 A2 | 5/2006 |
| WO | WO 2006/051110 A2 | 5/2006 |
| WO | WO 2006/058620 A2 | 6/2006 |
| WO | WO 2006/083952 A2 | 8/2006 |
| WO | WO 2006/110551 A2 | 10/2006 |

(56) References Cited

FOREIGN PATENT DOCUMENTS

| WO | WO-2006111169 A1 * | 10/2006 | ............ A61K 38/26 |
| --- | --- | --- | --- |
| WO | WO 2007/001150 A2 | 1/2007 | |
| WO | WO 2007/006307 A2 | 1/2007 | |
| WO | WO 2007/024700 A2 | 3/2007 | |
| WO | WO 2007/028394 A2 | 3/2007 | |
| WO | WO 2007/031187 A1 | 3/2007 | |
| WO | WO 2007/035665 A1 | 3/2007 | |
| WO | WO 2007/036299 A2 | 4/2007 | |
| WO | WO 2007/037607 A1 | 4/2007 | |
| WO | WO 2007/044867 A2 | 4/2007 | |
| WO | WO 2007/050656 A2 | 5/2007 | |
| WO | WO 2007/075534 A2 | 7/2007 | |
| WO | WO 2007/081792 A2 | 7/2007 | |
| WO | WO 2007/081824 A2 | 7/2007 | |
| WO | WO 2007/082381 A1 | 7/2007 | |
| WO | WO 2007/095288 A2 | 8/2007 | |
| WO | WO 2007/104786 A1 | 9/2007 | |
| WO | WO 2007/109221 A2 | 9/2007 | |
| WO | WO 2007/113205 A1 | 10/2007 | |
| WO | WO 2007/120899 A2 | 10/2007 | |
| WO | WO 2008/006496 A1 | 1/2008 | |
| WO | WO 2008/013938 A2 | 1/2008 | |
| WO | WO 2008/021560 A2 | 2/2008 | |
| WO | WO 2008/023050 A1 | 2/2008 | |
| WO | WO 2008/028914 A1 | 3/2008 | |
| WO | WO 2008/034881 A1 | 3/2008 | |
| WO | WO 2008/124522 A2 | 10/2008 | |
| WO | WO 2008/133908 A2 | 11/2008 | |
| WO | WO 2008/145323 A1 | 12/2008 | |
| WO | WO 2009/004627 A2 | 1/2009 | |
| WO | WO 2009/030498 A2 | 3/2009 | |
| WO | WO 2009/030499 A1 | 3/2009 | |
| WO | WO 2009/039963 A1 | 4/2009 | |
| WO | WO 2009/048959 A1 | 4/2009 | |
| WO | WO 2009/056569 A1 | 5/2009 | |
| WO | WO 2009/063072 A2 | 5/2009 | |
| WO | WO 2009/087081 A2 | 7/2009 | |
| WO | WO 2009/087082 A2 | 7/2009 | |
| WO | WO 2009/089181 A1 | 7/2009 | |
| WO | WO 2009/098318 A1 | 8/2009 | |
| WO | WO 2009/102467 A2 | 8/2009 | |
| WO | WO 2009/134380 A2 | 11/2009 | |
| WO | WO 2009/143014 A1 | 11/2009 | |
| WO | WO 2010/030670 A2 | 3/2010 | |
| WO | WO 2010/043566 A2 | 4/2010 | |
| WO | WO 2010/044867 A1 | 4/2010 | |
| WO | WO 2010/089304 A1 | 8/2010 | |
| WO | WO 2010/092163 A2 | 8/2010 | |
| WO | WO 2010/138671 A1 | 12/2010 | |
| WO | WO 2011/003822 A2 | 1/2011 | |
| WO | WO 2011/003823 A1 | 1/2011 | |
| WO | WO 2011/012719 A1 | 2/2011 | |
| WO | WO 2011/017554 A2 | 2/2011 | |
| WO | WO 2011/029892 A2 | 3/2011 | |
| WO | WO 2011/058082 A1 | 5/2011 | |
| WO | WO 2011/058083 A1 | 5/2011 | |
| WO | WO 2011/089203 A1 | 7/2011 | |
| WO | WO 2011/103575 A1 | 8/2011 | |
| WO | WO 2011/122921 A2 | 10/2011 | |
| WO | WO 2011/128374 A1 | 10/2011 | |
| WO | WO 2011/144673 A2 | 11/2011 | |
| WO | WO 2011/144674 A2 | 11/2011 | |
| WO | WO 2011/147980 A1 | 12/2011 | |
| WO | WO 2011/157402 A1 | 12/2011 | |
| WO | WO 2011/160066 A1 | 12/2011 | |
| WO | WO 2012/012352 A2 | 1/2012 | |
| WO | WO 2012/028172 A1 | 3/2012 | |
| WO | WO 2012/055967 A2 | 5/2012 | |
| WO | WO 2012/065996 A1 | 5/2012 | |
| WO | WO 2012/066086 A1 | 5/2012 | |
| WO | WO 2012/080320 A1 | 6/2012 | |
| WO | WO 2012/104342 A1 | 8/2012 | |
| WO | WO 2012/125569 A2 | 9/2012 | |
| WO | WO 2012/156296 A1 | 11/2012 | |
| WO | WO 2012/156299 A1 | 11/2012 | |
| WO | WO 2012/177929 A2 | 12/2012 | |
| WO | WO 2013/060850 A1 | 5/2013 | |
| WO | WO 2014/017849 A1 | 1/2014 | |
| WO | WO 2014/118355 A1 | 8/2014 | |
| WO | WO 2014/202483 A1 | 12/2014 | |
| WO | WO 2015/059302 A1 | 4/2015 | |

OTHER PUBLICATIONS

"Suspension" Taber's Cyclopedic Medical Dictionary, 19th Edition, p. 2097 (F.A. Davis Co., Philadelphia 2001).

(Feb. 2009) "European Public Assessment Report (EPAR) Optisulin", EPAR Summary for the Public, pp. 1-3.

(May 23, 2014) "Evaluation of the Blood Levels of the Drug (Lixisenatide), the Plasma Glucose Levels and Safety in Paediatric and Adult Patients with Type 2 Diabetes", NCT01572649, pp. 1-6.

(Oct. 11, 2016) "24-week Treatment with Lixisenatide in Type 2 Diabetes Insufficiently Controlled with Metformin and Insulin Glargine (GetGoal-Duo1)", ClinicalTrials.gov Identifier: NCT00975286, pp. 1-20.

18th World Health Congress (Helsinki). WMA Declaration of Helsinki—Ethical Principles for Medical Research Involving Human Subjects; WMA; Jun. 1964, pp. 1-8.

Abbas et al., "Impairment of synaptic plasticity and memory formation in GLP-1 receptor KO mice: Interaction between type 2 diabetes and Alzheimer's disease," Behav. Brain Res. 205:265-271 (2009).

Abraira et al., "Glycaemic separation and risk factor control in the Veterans Affairs Diabetes Trial: an interim report." Diabetes Obes Metab 11(2):150-56. (2009; Epub Jul. 29, 2008).

Action to Control Cardiovascular Risk in Diabetes Study Group, "Effects of intensive glucose lowering in type 2 diabetes." N Engl J. Med. 358(24):2545-59 (2008).

Actrapid® prescribing information, Apr. 2011, pp. 1-4.

Actrapid® summary of product characteristics, Apr. 2011, pp. 1-11.

Aderinwale et al., "Current therapies and new strategies for the management of Alzheimer's disease," Am J Alzheimers Dis Other Demen., 25(5):414-24 (2010).

Adis R&D Profile "Insulin Glargine: Glargine, HOE 71GT15, HOE 71GT80, HOE 901", Drugs R&D 2(2):107-109 (Aug. 1999).

Agholme et al., "An In Vitro Model for Neuroscience: Differentiation of SH-SY5Y Cells into Cells with Morphological and Biochemical Characteristics of Mature Neurons" J Alzheimer's Disease, 20:1069-82 (2010).

Aguilar, "Heart failure and diabetes: Time to pay attention" American Heart Journal, 162(5):795-97 (Nov. 2011).

Ahmad & Swann, and Bloomgren "Exenatide and rare adverse events." N Engl J Med 358(18):1969-72 (May 2008).

Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.

Ahren, "GLP-1 for type 2 diabetes", Experimental Cell Research, 317(9):1239-45 (Jan. 2011).

Ahualli "The Double Duct Sign" Radiology 244(1):314-5 (Jul. 2007).

Akbar, "Sub-Optimal postprandial blood glucose level in diabetics attending the outpatient clinic of a University Hospital" Saudi Med Journal, 24(10):1109-1112 (Oct. 2003).

Albert-Ludwigs University Freiburg, Institute fur Medizinische Biometrie und Statistik "Non-Inferiority Trials" dated Mar. 29, 2017, one page.

American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).

American Diabetes Association Annual Scientific Sessions, "New Diabetes Compound AVE0010 Showed Clear Dose Response Results With Once-A-Day Injection in Phase IIb Study", published Jun. 9, 2008, two pages.

(56) References Cited

OTHER PUBLICATIONS

American Diabetes Association, "Diagnosis and Classification of Diabetes Mellitus", Diabetes Care, 37 (Supplement 1):S81-S90 (Jan. 2014).
American Diabetes Association, "Standards of Medical Care in Diabetes—2011", Diabetes Care, 34 (Supplement 1):S11-S61 (Jan. 2011).
American Diabetes Association, "Standards of Medical Care in Diabetes—2017" Diabetes Care 40(Supplement 1):S1-S142 (Jan. 2017).
American Diabetes Association, "Standards of Medical Care in Diabetes—2008." Diabetes Care 31(Supplement 1):S12-S54.
American Diabetes Association, "Standards of Medical Care in Diabetes." Diabetes Care 28(Supplement 1): S4-S36 (Jan. 2005).
American Diabetes Association, "Type 2 diabetes in children and adolescents." Diabetes Care 23(3):381-89 (Mar. 2000).
Ampudia-Blasco et al., "Basal Plus Basal-Bolus approach in type 2 diabetes." Diabetes Technol Ther. 13 Suppl 1:S75-83 (Jun. 2011).
Aoki et al., Hydrolysis of Nonionic Surfactants, Ann. Rept. Takeda Res. Lab. 27, 172-176 (1968).
Apidra® prescribing information, Apr. 2012, pp. 1-6.
Aquiliante, "Sulfonylurea pharmacogenomics in type 2 diabetes: the influence of drug target and diabetes risk polymorphisms" Expert Rev Cardiovasc Ther. 8(3):359-72 (Mar. 2010).
Arnolds & Rave, "Basal insulin glargine vs prandial insulin lispro in type 2 diabetes," Lancet 378(9636):370-71 (2008).
Arnolds et al., "Further improvement in postprandial glucose control with addition of exenatide or sitagliptin to combination therapy with insulin glargine and metformin—a proof-of-concept study" Diabetes Care 33(7):1509-15 (2010).
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Ashford & Landi, "Stabilizing Properties of Tween 80 in Dilute Protein Solutions" Bull Parenteral Drug Assoc. 20(3):74-84 (May-Jun. 1966).
Atkinson et al., "Validation of a general measure of treatment satisfaction, the Treatment Satisfaction Questionnaire for Medication (TSQM), using a national panel study of chronic disease." Health Qual Life Outcomes. 2:12, pp. 1-13 (Feb. 2004).
Auerbach et al., "Angiogenesis assays: Problems and Pitfalls," Cancer and Metastasis Reviews, 19:167-72 (2000).
Aventis SEC Form 20-F; pp. 1-303 (Apr. 8, 2002).
Bakaysa et al., "Physicochemical basis for the rapid time-action of Lys.sup.B28 and Pro.sup.B29-insulin: Dissociation of a protein-ligand complex," Protein Science 5:2521-31 (1996).
Bam et al., "Stability of Protein Formulations: Investigation of Surfactant Effects by a Novel EPR Spectroscopic Technique," Pharmaceutical Research, 12(1):2-11 (Jan. 1995).
Bam et al., "Tween protects recombinant human growth hormone against agitation-induced damage via hydrophobic interactions" J. Ph. Sci. 87(12):1554-59 (Dec. 1998).
Banks et al., "Brain Uptake of the Glucagon-Like Peptide-1 Antagonist Exendin(9-39) after Intranasal Administration" Journal of Pharmacology and Experimental Therapeutics, 309:469-75 (2004).
Barnett "Lixisenatide: evidence for its potential use in the treatment of type 2 diabetes." Core Evidence 6:67-79 (published online Sep. 8, 2011).
Barnett & Owens, "Insulin Analogues," Lancet 349(9044):47-51 (1997).
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Barnett, "Dosing of Insulin Glargine in the Treatment of Type 2 Diabetes," Clinical Ther. 29(6):987-99 (Jun. 2007).
Barnett, "Insulin glargine in the treatment of type 1 and type 2 diabetes" Vascular Health and Risk Management 2:59-67 (published Jan. 25, 2006).
Bastyr et al., "Therapy focused on lowering postprandial glucose, not fasting glucose, may be superior for lowering HbA1c. IOEZ Study Group." Diabetes Care 23(9):1236-41 (Sep. 2000).
Bates et al., "Kinetics of hydrolysis of polyoxyethylene (20) sorbitan fatty acid ester surfactants," J. Pharmacy and Pharmacology 25(6):470-77 (Jun. 1973).
Beckman et al., "Diabetes and atherosclerosis: epidemiology, pathophysiology, and management." JAMA 287(19):2570-81 (May 2002).
Behar et al.. "Functional gallbladder and sphincter of oddi disorders." Gastroenterology 130(5):1498-1509 (2006).
Beintema & Campagne, "Molecular Evolution of Rodent Insulins," Mol. Biol. Evol. 4(1): 10-18, 1987.
Bell et al., "Sequence of the human insulin gene." 284(5751):26-32 (Mar. 1980).
Bennett, "Impact of the new WHO classification and diagnostic criteria." Diabetes Obes Metab 1(Supplement 2):S1-S6 (1999).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Berchtold & Hilgenfeld, "Binding of Phenol to R6 Insulin Hexamers" Biopolymers 51(2):165-72 (1999).
Bergenstal et al., "Type 2 Diabetes: Assessing the Relative Risks and Benefits of Glucose-lowering Medications" The American Journal of Medicine 123(4):e9-e18 (Apr. 2010).
Berger "Towards more physiological insulin therapy in the 1990s—A comment," Diabetes Research and Clinical Practice, 6(4): S25-31 (May 1989).
Berlie et al., "Glucagon-like peptide-1 receptor agonists as add-on therapy to basal insulin in patients with type 2 diabetes: a systematic review." Diabetes, Metabolic Syndrome and Obesity: Targets and Therapy 5:165-74 (2012).
Berlinsulin® H prescribing information, Apr. 2012, pp. 1-4.
Berlinsulin® H summary of product characteristics, Apr. 2012, pp. 1-11.
Bertram et al., "The Genetics of Alzheimer Disease: Back to the Future," Neuron, 68:270-81 (2010).
Best, Mathmatics and Statistics pp. 1-39, 1988.
Bethel & Feinglos, "Basal insulin therapy in type 2 diabetes." J Am Board Fam Pract. 18(3):199-204 (May-Jun. 2005).
Bhatt et al., "Chemical pathways of peptide degradation. I. Deamidation of adrenocorticotropic hormone," Pharm Res. 7(6):593-9 (1990).
Blanchard et al., "Time sequence of maturation of dystrophic neurites associate with Aβ deposits in APP/PS1 transgenic mice" Experimental Neurology, 184:247-63 (2003).
Bland and Altman, "Measurement error" BMJ 312:1654 (Jun. 29, 1996).
Bolen et al., "Systematic Review: Comparative Effectiveness and Safety of Oral Medications for Type 2 Diabetes Mellitus," Ann. Intern. Med. 147:386-399 (Epub Jul. 16, 2007).
Bolli "The pharmacokinetic basis of insulin therapy in diabetes mellitus," Diabetes Research and Clinical Practice, 6(4):S3-15 (May 1989).
Bolli et al., "Efficacy and safety of lixisenatide once daily vs. placebo in people with Type 2 diabetes insufficiently controlled on metformin (GetGoal-F1)." Diabetic Medicine 31:176-184 (published online Oct. 24, 2013).
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.

(56) References Cited

OTHER PUBLICATIONS

Boutajangout et al., "Characterisation of cytoskeletal abnormalities in mice transgenic for wild-type human tau and familial Alzheimer's disease mutants of APP and presenilin-1" Neurobiology of Disease, 15:47-60 (2004).
Boutajangout et al., "Increased tau phosphorylation but absence of formation of neurofibrillary tangles in mice double transgenic for human tau and Alzheimer mutant (M146L) presenilin-1" 318(1):29-33 (2002).
Brange "Galenics of Insulin" 1987, p. 35-36.
Brange & Langkjaer, "Chemical stability of insulin 3. Influence of excipients, formulation, and pH," Acta Pharma. Nord. 4(3):149-58 (1992).
Brange & Langkjaer, "Insulin Structure and Stability" Chapter 11; Pharm Biotechnol 5:315-50 (1993).
Brange et al., "Monomeric insulins and their experimental and clinical implications," Diabetes Care 13(9):923-45 (Sep. 1990).
Brange et al., "Neutral insulin solutions physically stabilized by addition of Zn2+," Diabetic Medicine 3:532-6 (Nov.-Dec. 1986).
Brange et al., "Toward Understanding Insulin Fibrillation," Journal of Pharmaceutical Sciences, 86(5):517-25 (1997).
Brange, "Design of Insulin Analogues for Meal-Related Therapy", J. Diabetes Complications 7(2):106-112 (Apr.-Jun. 1993). Abstract only.
Brazier et al., "Testing the validity of the Euroqol and comparing it with the SF-36 health survey questionnaire." Qual Life Res 2(3):169-80 (Jun. 1993).
Britannica, "Liquid", The Britannica Dictionary, 2023, Retrieved from url: <https://www.britannica.com/dictionary/liquid>.
Britannica, "Safety Testing in Animals", Pharmaceutical Industry—Drug Development, Regulation, Research, Jul. 26, 1999, Retrieved from url: <www.britannica.com/technology/pharmaceutical-industry/Safety-testing-in-animals#ref624890>.
Brod et al., "Adherence patterns in patients with type 2 diabetes on basal insulin analogues: missed, mistimed and reduced doses." Curr Med Res Opin. 28(12):1933-46 (2012).
Brod et al., "Examining correlates of treatment satisfaction for injectable insulin in type 2 diabetes: lessons learned from a clinical trial comparing biphasic and basal analogues." Health Quality of Life Outcomes. 5:8 (2007), pp. 1-10.
Broderick et al., "Guidelines for the Management of Spontaneous Intracerebral Hemorrhage in Adults," Circulation 116:e391-e413 (2007).
Brown & Nichols, "Slow response to loss of glycemic control in type 2 diabetes mellitus." Am J Manag Care. 9(3):213-17 (2003).
Bucceri et al., "Gallbladder and gastric emptying: relationship to cholecystokininemia in diabetics." Eur. J. Intern. Med. 13(2):123-28 (Mar. 2002).
Burgermeister et al. "The Isolation of Insulin from the Pancreas," Insulin, Part 2, p. 715-727 (1975).
Burke et al., "Nature of the B10 amino acid residue," Int. J. Peptide Protein Res., 23(4):394-401 (Apr. 1984).
Buse et al., "Use of twice-daily exenatide in Basal insulin-treated patients with type 2 diabetes: a randomized, controlled trial." Annals of Internal Medicine 154(2):103-12 (Jan. 2011).
Buse et al., "Effects of exenatide (Exendin-4) on glycemic control over 30 weeks in sulfonylurea-treated patients with type 2 diabetes." Diabetes Care 27(11):2628-35 (Nov. 2004).
Byetta® European Public Assessment Report (EPAR), pp. 1-36 (Feb. 16, 2012).
Byetta® Labeling Revision, pp. 1-24 (Jan. 11, 2008).
Byetta® Prescribing Information, pp. 1-34 (Revised Oct. 2009).
Byetta® Product information—EMA, pp. 1-2 (Jun. 10, 2016).
Byetta® Summary of Product Characteristics, updated Jul. 22, 2016, last accessed Jul. 31, 2017, pp. 1-13.
Byetta® Summary of Product Characteristics, updated Jan. 27, 2015, last accessed Apr. 18, 2015, pp. 1-12.
Byetta® Summary of Product Characteristics. Annex I, pp. 1-71, (2011).
Byrne et al., "Inhibitory Effects of Hyperglycemia on Fed Jejunal Motility: Potential Role of Hyperinsulinaemia," Euro. J. Clin. Invest. 28(1):72-78 (1998).
Cadario, "Sitagliptin" Drug Information Perspectives, 30(4):1-6 (2010).
Campas et al., "AVE-0010 GLP-1 Receptor Agonist Treatment of Diabetes", Drugs of the Future 33(10):838-40 (Oct. 2008).
Campbell et al., "Insulin Glargine," Clin. Therapeutics 23(12):1938-57 (2001).
Canadian Cardiovascular Society Grading of Angina Pectoris. From http://www.sscts.org/pages/classificationanginaccs.aspx. Accessed May 27, 2016, one page.
Canadian Diabetes Association. Clinical Practice Guidelines Expert Committee. Canadian Diabetes Association 2008. Clinical Practice Guidelines for the Prevention and Management of Diabetes in Canada. Canadian Journal of Diabetes S162-S167 (2008).
Cannon et al. for the Pravastatin or Atorvastatin Evaluation and Infection Therapy-Thrombolysis in Myocardial Infarction Investigators. "Intensive versus Moderate Lipid Lowering with Statins after Acute Coronary Syndromes." N Engl J Med 350(15):1495-504 (Apr. 2004; Epub Mar. 8, 2004).
Caprio, "Obesity and Type 2 Diabetes: The Twin Epidemic" Diabetes Spectrum 16(4):230 (2003).
Casas et al., "Massive CA1/2 Neuronal Loss with Intraneuronal and N-Terminal Truncated Aβ 42 Accumulation in a Novel Alzheimer Transgenic Model" American Journal of Pathology 165(4):1289-1300 (2004).
Centers for Disease Control and Prevention. National diabetes fact sheet: general information and national estimates on diabetes in the United States, 2003. Rev ed. Atlanta, GA: U.S. Department of Health and Human Services, Centers for Disease Control and Prevention, pp. 1-8, 2004.
Chancel, "Natixis Conference on Diabetes." Sanofi, Paris, pp. 1-23 (Nov. 8, 2011).
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Charles et al., "Prevention of Type 2 Diabetes Role of Metformin" Review Article, Drugs 1999; 58 Suppl. 1:71-73 (Sep. 1999).
Chatterjee et al., "Insulin glargine and its place in the treatment of Types 1 and 2 diabetes mellitus." Expert Opin Pharmacother 7(10):1357-71 (2006).
Chawla et al., "Aggregation of Insulin, Containing Surfactants, in Contact with Different Materials", Diabetes 34(5):420-24 (May 1985).
Chen et al., Tissue-specific Expression of Unique mRNAs That Encode Proglucagon-derived Peptides or Exendin 4 in the Lizard, J. Biol. Chem. 272(7):4108-15 (1997).
Cheung et al., "Effects of all-trans-retinoic acid on human SH-SY5Y neuroblastoma as in vitro model in neurotoxicity research" Neuro Toxicology, 30:127-35 (2009).
Chi et al., "Excipients and their Effects on the Quality of Biologics" pp. 1-9, (May 2012).
Childs et al., "Defining and Reporting Hypoglycemia in Diabetes," Diabetes Care 28(5):1245-9 (May 2005).
Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC35&&GDL_Disease_ID=A6D1OE80-887D-49A7-B3BB-0517D38CE757, accessed on May 14, 2014, pp. 1-12.
Christensen et al., "Lixisenatide for type 2 diabetes mellitus," Expert Opin. 20(4):549-57 (Epub Mar. 11, 2011).
Christensen et al., "Lixisenatide, a Novel GLP-1 Receptor Agonist for the Treatment of Type 2 Diabetes Mellitus", IDrugs: The Investigational Drugs Journal 12(8):503-13 (Aug. 2009).
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/archive/NCT00688701/2012_09_30/changes Accessed on Jun. 2, 2016, pp. 1-5 submitted.

(56) References Cited

OTHER PUBLICATIONS

Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.
Cochran et al., "The Use of U-500 in Patients with Extreme Insulin Resistance" Diabetes Care, 28(5):1240-44 (2005).
Colagiuri, "Diabesity: therapeutic options" Diabetes, Obesity and Metabolism 12(6):463-73 (Jun. 2010).
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino et al., "Therapy with insulin glargine (Lantus) in toddlers, children and adolescents with type 1 diabetes," Diabetes Research and Clinical Practice (2005), vol. 70, pp. 1-7.
Community register of medicinal products for human use, Chemical Subgroup A10BX, "Lyxumia" European Commission—Public Health, p. 1-2 (May 2, 2013).
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo et al., "Postprandial plasma-glucose and -insulin responses to different complex carbohydrates," Diabetes 26(12):1178-83 (Dec. 1977).
Croom et al., "Liraglutide a Review of its Use in Type 2 Diabetes Mellitus," Drugs, 69(14):1985-2004 (2009).
Cryer "Hypoglycemia is the limiting factor in the management of diabetes," Diabetes Metab. Res. Rev. 15(1):42-46 (Jan.-Feb. 1999).
Cvetkovic et al., "Exenatide a Review of Its Use in Patients with Type 2 Diabetes Mellitus (as an Adjunct to Metformin and/or a Sulfonylurea)," Drugs, 67(6):935-54 (2007).
Czech et al., "Proteolytical processing of mutated human amyloid precursor protein in transgenic mice" Molecular Brain Research 47:108-116 (1997).
D'Alessio et al., "GLP-1 Receptor Agonists: Strategies for PPG Control," Medical Nursing Edu., 3:1-26 (Jan. 2010).
D'Alessio et al., "Glucagon-like Peptide 1 Enhances Glucose Tolerance Both by Stimulation of Insulin Release and by Increasing Insulin-independent Glucose Disposal," J. Clin. Invest. 93(5):2263-66 (1994).
D'Alessio et al., "The role of dysregulated glucagon secretion in type 2 diabetes" Diabetes, Obesity and Metabolism, 13(Supppl.1):126-132 (Oct. 2011).
Das et al., "The British Cardiac Society Working group definition of myocardial infarction: implications for practice." Heart 92(1):21-6 (Jan. 2006; Epub Apr. 14, 2005).
Database, Adiscti, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
DCCT, Diabetes Control and Complications Trial/ Epidemiology of Diabetes Interventions and Complications Research Group: Intensive diabetes therapy and carotid intima-media thickness in type 1 diabetes. N Engl J Med 348(23):2294-303 (Jun. 2003).
DCCT, Diabetes Control and Complications Trial/ Epidemiology of Diabetes Interventions and Complications Research Group: Intensive diabetes treatment and cardiovascular disease in patients with type 1 diabetes. N Engl J Med. 353(25):2643-59 (Dec. 2005).
De Arriba et al., "Carbonyl stress and NMDA receptor activation contribute to methylglyoxal neurotoxicity" Free Radical Biology & Medicine, 40:779-90 (2006).
De la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).
De Le Pena, "Pharmacokinetics and Pharmadynamics of High-Dose Human Regular U-500 Insulin Versus Human Regular U-1 00 Insulin in Healthy Obese Subjects" Diabetes Care, 34(12):2496-501 (2011).
De Lemos et al., "Early intensive vs. a delayed conservative simvastatin strategy in patients with acute coronary syndromes: phase Z of the A to Z trial." JAMA 292(11):1307-16 (Sep. 2004; Epub Aug. 30, 2004).
De Rosa, et al. "Intranasal administration of nerve growth factor (NGF) rescues recognition memory deficits in A D11 anti-NGF transgenic mice." Proc Natl Acad. Sci., 102:3811-16 (2005).
De Venciana et al., "Postprandial versus preprandial blood glucose monitoring in women with gestational diabetes mellitus requiring insulin therapy." N Engl J Med 333(19):1237-41 (Nov. 1995).
Deacon et al., "Dipeptidyl Peptidase IV Inhibition Potentiates the Insulinotropic Effect of Glucagon-Like Peptide 1 in the Anesthetized Pig," Diabetes 47(5):764-69 (1998).
Deacon et al., "Dipeptidyl Peptidase IV Resistant Analogues of Glucagon-Like Peptide-1 Which Have Extended Metabolic Stability and Improved Biological Activity," Diabetologia 41(3):271-78 (1998).
Definition of "Combination", Concise Oxford English Dictionary, edited by A. Stevenson and M. Waite, Oxford University press, 12th Edition, Aug. 2011, 4 pages submitted, see p. 285.
Definition of "induce" Dictionary.com; last accessed Sep. 29, 2016, pp. 1-6.
Definition of "prevent" Dictionary.com; last accessed Sep. 29, 2016, pp. 1-6.
Definition of "reduce" Dictionary.com; last accessed Aug. 13, 2017, pp. 1-4.
Definition of "hypoglycemia" Stedman's Medical Dictionary, 5th Edition, Japan, published on Feb. 20, 2002, p. 853; in Japanese, English translation also submitted.
Definition of indication, Merriam-Webster online, accessed Oct. 22, 2015, 2 pages.
Definition of palliative, http://medicaldictionary.thefreedictionary.com/, accessed on Nov. 6, 2014, pp. 1-2.
Definition of Phase, Clinical Trials.gov NIH, accessed Mar. 16, 2016, one page.
Definition of sphincter of pancreatic duct in the Medical Dictionary, http://medicaldictionary.thefreedictionary.com/, accessed on May 22, 2014, pp. 1-2.
DeFronzo "Effects of Exenatide (Exendin-4) on Glycemic Control and Weight Over 30 Weeks in Metformin-Treated Patients with Type 2 Diabetes", Diabetes Care 28(5):1092-1100 (May 2005).
DeFronzo "Pathogenesis of Type 2 Diabetes Implications for Metformin" Short Communication, Drugs 1999; 58(Suppl 1):29-30 (Sep. 1999).
DeFronzo "Pharmacologic Therapy for Type 2 Diabetes Mellitus." Ann Int Med. 131:281-303 (1999).
Degn et al., "Effect of Intravenous Infusion of Exenatide (Synthetic Exendin-4) on Glucose-Dependent Insulin Secretion and Counterregulation During Hypoglycemia." Diabetes 53(9):2397-2403 (Sep. 2004).
Del Prato & Tiengo, "The importance of first-phase insulin secretion: implications for the therapy of type 2 diabetes mellitus." Diabetes Metab Res Rev. 17(3):164-74 (May-Jun. 2001).
Del Prato et al., "Global Partnership for Effective Diabetes Management. Tailoring treatment to the individual in type 2 diabetes practical guidance from the Global partnership for effective diabetes managment." Int J Clin Pract. 64(3):295-304 (Feb. 2010).

(56) References Cited

OTHER PUBLICATIONS

Delatour et al., "Alzheimer pathology disorganizes cortico-cortical circuitry: direct evidence from a transgenic animal model" Neurobiology of Disease, 16:41-47 (2004).
Denker et al., "Exenatide (Exendin-4)-Induced Pancreatitis: A case report" Diabetes Care 29(2):471 (Feb. 2006).
Derewenda et al., "Phenol Stabilizes More Helix in a New Symmetrical Zinc Insulin Hexamer" Nature 338(6216):594-96 (Apr. 1989).
Devries et al., "Sequential intensification of metformin treatment in type 2 diabetes with liraglutide followed by randomized addition of basal insulin prompted by A1C targets." Diabetes Care 35:1446-54 (2012).
DeWitt & Hirsch, "Outpatient insulin therapy in type 1 and type 2 diabetes mellitus: scientific review." JAMA 289(17):2254-64 (May 2003).
Dewitt, "Case Study: Treating New On-Set Catabolic Type 2 Diabetes With Glargine and Lispro", Clinical Diabetes vol. 24, No. 4, pp. 180-181,(Oct. 2006).
Diabetes Prevention Program Research Group. "Reduction in the incidence of type 2 diabetes with lifestyle intervention or metformin." N Engl J. Med. 346(6):393-403 (2002).
Dietrich, et al. (Dec. 12, 2016) "The DPP4 Inhibitor Linagliptin Protects from Experimental Diabetic Retinopathy", PLoS ONE, vol. 11, No. 12, pp. 1-17.
Dinneen & Gerstein, "The association of microalbuminuria and mortality in non-insulin dependent diabetes mellitus. A systematic overview of the literature." Arch Intern Med 157(13):1413-8 (Jul. 1997).
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon et al., "Regeneration of Insulin Activity From the Separated and Inactive A and B Chains," Nature, vol. 188, No. 4752 (1960), pp. 721-724.
Dolan, "Modeling valuations for EuroQol health states." Med Care 35(11):1095-1108 (Nov. 1997).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Donahue et al., "Postchallenge glucose concentration and coronary heart disease in men of Japanese ancestry. Honolulu Heart Program." Diabetes 36(6):689-92 (Jun. 1987).
Donelli, "Plastic Biliary Stent Occlusion: Factors Involved and Possible Preventive Approaches," Clinical Medicine & Research 5(1):53-60 (Mar. 2007).7.
Dormandy et al., "Secondary prevention of macrovascular events in patients with type 2 diabetes in the PROactive Study (PROspective pioglitAzone Clinical Trial in macrovascular Events): a randomised controlled trial," Lancet. 366(9493):1279-89 (Oct. 8, 2005).
Doyle et al., "Mechanisms of action of glucagon-like peptide 1 in the pancreas" Pharmacal Ther. (Mar. 2007) pp. 546-593, vol. 113, No. 3.
Drucker et al., "The incretin system: glucagon-like peptide-1 receptor agonists and dipeptidyl peptidase-4 inhibitors in type 2 diabetes." Lancet; 368(9548):1696-705 (Nov. 11, 2006).
Drucker, "Glucagon-Like Peptides," Diabetes 47(2):159-69 (1998).
Drucker, "Mini review: The Glucagon-Like Peptides," Endocrinology 142(2):521-27 (2001).
Drucker, "The Biology of Incretin Hormones," Cell Metab. 3(3):153-65 (2006).
Druet et al., "Characterization of insulin secretion and resistance in type 2 diabetes of adolescents." J Clin Endocrinol Metab 91(2):401-404 (Feb. 2006; epub Nov. 15, 2005).
Drug Facts and Comparison; J. B. Lippincot Company, St. Louis, MO; pp. 1781-1790 (1988).
DrugBank, "Insulin glargine," available online at http://www.drugbank.ca/drugs/DB00047, 16 pages (accessed online Sep. 23, 2014).
Drury et al., "Diabetic nephropathy," British Medical Bulletin, vol. 45, No. 1, 1989, pp. 127-147.
Dubois et al., "Revising the definition of Alzheimer's disease: a new lexicon." Lancet Neural. 9: 1118-27 (2010).
Dunn et al., "Insulin Glargine: An Updated Review of its Use in the Management of Diabetes Mellitus" Drugs 63(16):1743-1778 (2003).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
During et al., "Glucagon-like peptide-1 receptor is involved in learning and neuroprotection" Nat Med (2003) pp. 1173-1179, vol. 9.
Eckert et al., "Assessing the progression of Parkinson's disease: A metabolic network approach," Lancet Neurol. 6(10):926-32 (Oct. 2007).
Eckert et al., "Alzheimer's Disease-like Alterations in Peripheral Cells from Presenilin-1 Transgenic Mice" Neurobiology of Disease 8, 331-342 (2001).
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6017; Clinical Trial Eudra CT No. 2007-005884-92, accessed Apr. 24, 2015, one page.
EFC6018; Clinical trial EudraCT 2007-005887-29, "Getgoal-Mono" accessed Jul. 27, 2014; pp. 1-16.
EMA Press Release, "European Medicines Agency recommends suspension of Avandia, Avandamet and Avaglim" pp. 1-2 (Sep. 23, 2010).
EMEA Public Statement on Insuman Infusat (Feb. 14, 2000), at http://www.ema.europa.eu/ema/index.jsp?curl=pages/news_and_events/news/2010/08/news_detail_001094.jsp&mid=WC0b01ac058004d5c1 (accessed Jun. 1, 2017); pp. 1-2.
Encyclopedia of Drugs, "Metformin" Moscow, Drug Register of 2001, p. 549, English translation provided pp. 1-2.
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
English translation of Search Report for Chinese Patent Application No. 201280053404.6; dated Feb. 10, 2015, pp. 1-3.
English translation of Search Report for Chinese Patent Application No. 20140220537.9; dated Feb. 13, 2015, pp. 1-2.
English translation of the TIPO Search Report for ROC Patent Application No. 101131466 dated Mar. 2, 2016, one page.
English translation of the TIPO Search Report for ROC Patent Application No. 104116749, dated Feb. 22, 2016, one page.
English Translation of TIPO Search Report for ROC Patent Application No. 101130936, dated Dec. 1, 2015, one page.
European Diabetes Policy Group, "A desktop guide to Type 2 diabetes mellitus." Diabetic Medicine 16 (9):716-730 (1999).
European Medicines Agency—Science Medicines Health "Toujeo" EPAR Summary for the Public, first published Nov. 5, 2009, pp. 1-3.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
European Medicines Agency, "Toujeo (previously Optisulin) insulin glargine," <http://www.ema.europa.eu/ema/index.jsp?curl=pages/medicines/human/medicines/000309/human_med_000955.jsp&mid=WC0b01ac058001d124>, last updated Jan. 25, 2016, visited Feb. 3, 2016, pp. 1-6—screenshot of "About" tab of webpage and printouts of "About" tab of webpage with listed items collapsed and expanded.
European Medicines Agency, "Guideline on clinical investigation of medicinal products in the treatment of hypertension" (EMA/238/1995 Rev 3) pp. 1-18 (Nov. 18, 2010).

(56) References Cited

OTHER PUBLICATIONS

European Medicines Agency, "Note for guidance on non-clinical safety studies for the conduct of human clinical trials and marketing authorization for pharmaceuticals" pp. 1-22 (Jul. 2008).
European Medicines Agency, Committee for Medicinal Products for Human Use (CHMP), "Assessment report—Lyxumia", pp. 1-81 (Nov. 28, 2012).
European Medicines Agency, Lyxumia 10/20 micrograms solution for injection, Summary of Product Characteristics, Date of first authorisation: Feb. 1, 2013, pp. 1-82 (retrieved from the internet on Mar. 12, 2018).
EuroQol Group, "EuroQol—a new facility for the measurement of health-related quality of life." Health policy (Amsterdam, Netherlands) 16(3):199-208 (Dec. 1990).
Ex Parte Herrmann, Appeal No. 2009-001777 U.S. Appl. No. 10/616,457 (B. Pai. Nov. 13, 2009).
Excerpts from "Handbook of Pharmaceutical Excipients" 2nd Edition (eds. A. Wade and P. J. Weller) American Pharmaceutical Association, Washington, The Pharmaceutical Press, London; pp. 1-55 (1994).
Executive Summary, "Standards of Medical Care in Diabetes-2009" Diabetes Care,32(Suppl. 1):S6-S12 (Jan. 2009).
Extended European Search Report for Euorpean Application No. 98 11 0889.7; dated Oct. 14, 1998, pp. 1-4.
Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 0270.2; dated Sep. 19, 2011, pp. 1-8.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 30 5126; dated Apr. 11, 2013, pp. 1-7.
Extended European Search Report for European Application No. 13 30 5432.0; dated Sep. 13, 2013, pp. 1-5.
Extended European Search Report for European Application No. 14 16 6877.2; of Aug. 18, 2014, pp. 1-6.
Extended European Search Report for European Application No. 14 19 7154.9: dated Apr. 8, 2015, pp. 1-7.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Extended European Search Report for European Application No. 15 15 9064.3; dated Oct. 19, 2015, pp. 1-4.
Extended European Search Report for European Application No. 16 19 0103.8; dated Jun. 23, 2017, pp. 1-5.
Extended European Search Report for European Application No. 17 20 2727.8; dated Dec. 20, 2017, pp. 1-9.
Fabunmi et al., "Patient characteristics, drug adherence patterns, and hypoglycemia costs for patients with type 2 diabetes mellitus newly initiated on exenatide or insulin glargine." Curr Med Res Opin. 25(3):777-86 (2009).
Faichney, "Metformin in Type 1 diabetes: Is This a Good or Bad Idea?" Diabetes Care 26(5):1655 (May 2003).
Faivre et al., "Effect of GIP Analogues in Neuronal Signalling, Cell Proliferation and Learning and Memory." Regulatory Peptides; 164(1):40-41 (Sep. 9, 2010, published online Aug. 20, 2010).

Farag & Gaballa, "Diabesity: an overview of a rising epidemic" Nephrol Dial Transplant 26(1):28-35 (Jan. 2011; Epub Nov. 2, 2010).
FDA—Food and Drug Administration, CFR—Code of Federal Regulations Title 21, Chapter 1, Subchapter D, Part 312.21, "Phases of an investigation" pp. 1-2, Apr. 1, 2015.
FDA Frequently Asked Questions about Combination Products;accessed from www.fda.gov/CombinationProducts/AboutCombinationProducts/usm101496.1/htm, 2009 downloaded Jul. 13, 2012, pp. 1-18.
FDA Guidance for Industry, US Department of Health and Human Services, Food and Drug Administration, Center for Drug Evaluation and Research (CDER), pp. 1-11, Feb. 2014.
FDA label of Apidra®, May 2014, pp. 1-35.
FDA label of Humalog®, Mar. 2013, pp. 1-27.
FDA label of Lantus®, Oct. 2013, pp. 1-44.
FDA, "Guidance of Industry—Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
FDA, Food and Drug Administration. Guidance for Industry—Diabetes Mellitus: Developing Drugs and Therapeutic Biologics for Treatment and Prevention. pp. 1-34 (Feb. 2008).
Feinglos et al., "Effects of liraglutide (NN2211), a long-acting GLP-1 analogue, on glycaemic control and bodyweight in subjects with type 2 diabetes." Diabetic Medicine, 22(8):1016-23 (Jul. 2005).
Fieller, Symposium on Interval Estimation; "Some Problems with Interval Estimation" Journal of the Royal Statistical Society 16(2):175-85 (1954).
Final Office Action from U.S. Appl. No. 12/617,805; mailed Feb. 11, 2013, pp. 1-13.
Final Office Action from U.S. Appl. No. 12/617,805; mailed Jan. 12, 2012, pp. 1-14.
Final Office Action from U.S. Appl. No. 12/617,805; mailed Jan. 13, 2015, pp. 1-11.
Final Office Action from U.S. Appl. No. 12/617,805; mailed May 25, 2016, pp. 1-9.
Final Office Action issued in U.S. Appl. No. 13/123,835; mailed Feb. 12, 2013, pp. 1-13.
Final Office Action issued in U.S. Appl. No. 13/123,835; mailed Nov. 18, 2015, pp. 1-16.
Final Office Action issued in U.S. Appl. No. 13/602,913; mailed on Apr. 2, 2015, pp. 1-7.
Final Office Action issued in U.S. Appl. No. 13/602,913; mailed on Jun. 20, 2014, pp. 1-27.
Final Office Action issued in U.S. Appl. No. 13/602,913; mailed on Sep. 13, 2013, pp. 1-11.
Final Rejection in U.S. Appl. No. 13/633,496; mailed Aug. 26, 2015, pp. 1-16.
Final Rejection in U.S. Appl. No. 13/633,496; mailed Nov. 18, 2014, pp. 1-11.
Final Rejection in U.S. Appl. No. 13/633,496; mailed Nov. 4, 2013, pp. 1-7.
Final Rejection in U.S. Appl. No. 13/633,496; mailed Oct. 13, 2016, pp. 1-10.
Final Rejection in U.S. Appl. No. 13/633,563; mailed Apr. 8, 2016, pp. 1-12.
Final Rejection in U.S. Appl. No. 13/633,563; mailed Apr. 22, 2015, pp. 1-12.
Final Rejection in U.S. Appl. No. 13/633,563; mailed Apr. 28, 2017, pp. 1-12.
Final Rejection in U.S. Appl. No. 13/633,563; mailed Dec. 16, 2013, pp. 1-58.
Final Rejection issued in U.S. Appl. No. 12/617,811; mailed Jan. 4, 2013, pp. 1-6.
Final Rejection issued in U.S. Appl. No. 12/617,811; mailed Jul. 31, 2015, pp. 1-15.
Final Rejection issued in U.S. Appl. No. 13/110,568; mailed Feb. 21, 2013, pp. 1-20.
Final Rejection issued in U.S. Appl. No. 13/310,118; mailed Aug. 2, 2012, pp. 1-20.

(56) References Cited

OTHER PUBLICATIONS

Final Rejection issued in U.S. Appl. No. 13/363,956; mailed May 20, 2014, pp. 1-16.
Final Rejection issued in U.S. Appl. No. 13/382,442; mailed Jul. 17, 2013, pp. 1-30.
Final Rejection issued in U.S. Appl. No. 13/382,442; mailed Jun. 13, 2014, pp. 1-29.
Final Rejection issued in U.S. Appl. No. 13/382,442; mailed Aug. 11, 2015, pp. 1-35.
Final Rejection issued in U.S. Appl. No. 13/382,442; mailed Sep. 21, 2016, pp. 1-32.
Final Rejection issued in U.S. Appl. No. 13/382,772; mailed Jun. 3, 2014, pp. 1-34.
Final Rejection issued in U.S. Appl. No. 13/382,772; mailed Feb. 10, 2015, pp. 1-36.
Final Rejection issued in U.S. Appl. No. 13/382,772; mailed Feb. 24, 2016, pp. 1-36.
Final Rejection issued in U.S. Appl. No. 13/467,707; mailed Feb. 12, 2016, pp. 1-12.
Final Rejection issued in U.S. Appl. No. 13/467,707; mailed Feb. 25, 2014, pp. 1-18.
Final Rejection issued in U.S. Appl. No. 13/467,707; mailed Jan. 7, 2015, pp. 1-8.
Final Rejection issued in U.S. Appl. No. 13/468,422; mailed Jan. 6, 2014, pp. 1-21.
Final Rejection issued in U.S. Appl. No. 13/468,422; mailed Jan. 23, 2015, pp. 1-27.
Final Rejection issued in U.S. Appl. No. 13/469,633; mailed Dec. 4, 2013, pp. 1-17.
Final Rejection issued in U.S. Appl. No. 13/469,633; mailed Jan. 23, 2015, pp. 1-12.
Final Rejection issued in U.S. Appl. No. 13/509,507; mailed Jul. 23, 2015, pp. 1-11.
Final Rejection issued in U.S. Appl. No. 13/509,507; mailed May 13, 2016, pp. 1-11.
Final Rejection issued in U.S. Appl. No. 13/509,542, mailed Jan. 28, 2015, pp. 1-26.
Final Rejection issued in U.S. Appl. No. 13/509,542, mailed Feb. 10, 2016, pp. 1-40.
Final Rejection issued in U.S. Appl. No. 13/509,542; mailed Nov. 21, 2013, pp. 1-34.
Final Rejection issued in U.S. Appl. No. 13/595,590; mailed Apr. 2, 2014, pp. 1-7.
Final Rejection issued in U.S. Appl. No. 13/595,590; mailed Dec. 19, 2014, pp. 1-14.
Final Rejection issued in U.S. Appl. No. 13/661,476, mailed on Oct. 2, 2014, pp. 1-33.
Final Rejection issued in U.S. Appl. No. 13/692,640; mailed Jan. 6, 2015, pp. 1-11.
Final Rejection issued in U.S. Appl. No. 13/692,640; mailed Jun. 2, 2015, pp. 1-12.
Final Rejection issued in U.S. Appl. No. 13/700,631; mailed Apr. 13, 2015, pp. 1-19.
Final Rejection issued in U.S. Appl. No. 13/700,631; mailed Jun. 18, 2014, pp. 1-25.
Final Rejection issued in U.S. Appl. No. 13/819,114; mailed Mar. 2, 2015, pp. 1-10.
Final Rejection issued in U.S. Appl. No. 14/172,151; mailed Jul. 20, 2015, pp. 1-18.
Final Rejection issued in U.S. Appl. No. 14/172,151; mailed Jan. 4, 2016, pp. 1-20.
Final Rejection issued in U.S. Appl. No. 14/303,895; mailed Apr. 27, 2016, pp. 1-10.
Final Rejection issued in U.S. Appl. No. 15/162,563; mailed Dec. 18, 2017, pp. 1-16.
Final-Rejection issued in U.S. Appl. No. 13/432,811; mailed Dec. 12, 2014, pp. 1-8.
Final-Rejection issued in U.S. Appl. No. 13/432,811; mailed Feb. 10, 2016, pp. 1-9.
Final-Rejection issued in U.S. Appl. No. 13/432,811; mailed Mar. 31, 2015, pp. 1-9.
Final-Rejection issued in U.S. Appl. No. 13/432,811; mailed Sep. 6, 2013, pp. 1-8.
Fonseca et al., "Efficacy and Safety of the Once-Daily GLP-1 Receptor Agonist Lixisenatide in Monotherapy" Diabetes Care, 35:1225-31 (Jun. 2012).
Forlenza et al., "Diagnosis and biomarkers of predementia in Alzheimer's disease," BMC Medicine 8:89 pp. 1-14 (Dec. 2010).
Forman et al., "Higher levels of albuminuria within the normal range predict incident hypertension." J Am Soc Nephrol 19(10):1983-88 (Oct. 2008).
Fox et al., Protein Science 10: 622-30 (2001).
Fransson et al., "Oxidation of Human Insulin-Like Growth Factor I in Formulation Studies: Kinetics of Methionine Oxidation in Aqueous Solution and in Solid State" Pharmaceutical Research 13(8):1252-57 (Aug. 1996).
Galloway & Root, "New forms of insulin," Diabetes 21 (2 Suppl):637-48 (1972).
Gallwitz, "Liraglutide. GLP-1 Receptor Agonist Treatment of Type 2 Diabetes Treatment of Obesity," Drugs of the Future, 33(1):13-20 (Jan. 2008).
Game "Novel hypoglycaemic agents: Considerations in patients with chronic kidney disease" Nephron Clin Pract. 126(1):14-18 (Jan. 11, 2014).
Gandhi & Wood, "Molecular pathogenesis of Parkinson's disease." Hum Mol Genet 14:2749-55 (2005).
Ganz et al., "The association of body mass index with the risk of type 2 diabetes: a case-control study nested in an electronic health records system in the United States." Diabetology & Metabolic Syndrome, 6:50, pp. 1-8 (Apr. 2014).
Garber et al., "Liraglutide versus glimepiride monotherapy for type 2 diabetes (LEAD-3 Mono): a randomised, 52-week, phase III, double blind, parallel-treatment trial", The Lancet, 373(9662):473-81 (Feb. 7, 2009).
Garg, R., et al., "U-500 insulin: why, when and how to use in clinical practice", Diabetes/Metabolism Research and Reviews, 23:265-268 (2007).
Garriques et al., "The Effect of Mutations on the Structure of Insulin Fibrils Studied by Fourier Transform Infrared (FTIR) Spectroscopy and Electron Microscopy," Journal of Pharmaceutical Sciences, 91(12):2473-80 (2002).
Gatlin & Gatlin, "Formulation and Administration Techniques to Minimize Injection Pain and Tissue Damage Associated with Parenteral Products" in Injectable Drug Development, Chapter 17; pp. 401-421 (eds. P.K. Gupta and G.A. Brazeau) (CRC Press) (1999).
Gault et al. "GLP-1 agonists facilitate hippocampal L TP and reverse the impairment oiL TP induced by beta-amyloid." Eur J Pharmacal; 587(1-3):112-7 (Jun. 10, 2008; published online Mar. 29, 2008).
Gavin—Committee Report, "Report of the Expert Committee on the Diagnosis and Classification of Diabetes Mellitus," Diabetes Care, 20(7):1183-97 (Jul. 1997).
Geiger, Chem. Zeitung, 100(3), p. 54-56. (Jan. 1976).
GenBank: AAA52578.1 "GM-CSF [*Homo sapiens*]" dated Nov. 8, 1994; accessed Jan. 18, 2017, one page.
GenBank: AAA59149.1 "Interleukin 4 [*Homo sapiens*]" dated Jan. 6, 1995; accessed Jan. 18, 2017, one page.
GenBank: AAP20099.1 "Interferon Alpha 2B [*Homo sapiens*]" dated Apr. 30, 2003; accessed Jan. 18, 2017, one page.
Gengler et al., "Vai(8)GLP-1 rescues synaptic plasticity and reduces dense core plaques in APP/PS1 mice" Neurobiol Aging (2012) pp. 265-276, vol. 33.
Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Gerich, "Insulin glargine: long-acting basal insulin analog for improved metabolic control." Curr Med Res Opin. 20(1):31-37 (Jan. 2004).

(56) References Cited

OTHER PUBLICATIONS

Gerstein et al., "Albuminuria and risk of cardiovascular events, death, and heart failure in diabetic and nondiabetic individuals." JAMA 286(4):421-6 (Jul. 2001).
Giacometti et al., "In vitro activity of the histatin derivative P-113 against multidrug-resistant pathogens responsible for pneumonia in immunocompromised patients." 49(3):1249-52 (Mar. 2005).
Gillies et al., "Insulin Glargine" Drugs 59(2)L253-60 (Feb. 2000).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Giugliano et al., "Treatment regimens with insulin analogues and haemoglobin A1c target of <7% in type 2 diabetes: A systematic review." Diabetes Research and Clinical Practice 92(1):1-10 (Apr. 2011; Epub Sep. 6, 2010).
Glucophage XR, Product Information, Bristol-Meyers Squibb Company (Jan. 2009).
Godoy-Matos, "The role of glucagon on type 2 diabetes at a glance," Diabetology & Metabolic Syndrome 6:91, pp. 1-5 (Aug. 2014).
Goke et al., "Distribution of GLP-1 Binding Sites in the Rat Brain: Evidence that Exendin-4 is a Ligand of Brain GLP-1 Binding Sites," Eur. J. Neurosci. 7(11):2294-2300 (1995).
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Goldstein et al.. Tests of Glycemia in Diabetes. Diabetes Care 18(6):896-909 (Jun. 1995).
Gough, K. et al.; Assessment of Dose Proportionality: Report from the Statisticians in the Pharmaceutical Industry/ Pharmacokinetics UK Joint Working Party; Drug Information Journal, vol. 29, 1995, pp. 1039-1048.
Goykhman et al., "Insulin Glargine: a review 8 years after its introduction." Expert Opin. Pharmacother. 10(4):705-18 (2009).
Grau & Saudek, "Stable Insulin Preparation for Implanted Insulin Pumps", Diabetes 36(12):1453-59 (Dec. 1987).
Greig et al., "Once Daily Injection of Exendin-4 to Diabetic Mice Achieves Long-Term Beneficial Effects on Blood Glucose Concentrations." Diabetologia 42(1):45-50 (1999).
Gromada et al., "Alpha-Cells of the Endocrine Pancreas: 35 Years of Research but the Enigma Remains" Endocrine Reviews 28(1):84-116 (Jan. 2007).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Gualandi-Signorini & Giorgi, "Insulin formulations—a review" European Review for Medical and Pharmacological Sciences 5:73-83 (2001).
Gura, "Systems for Identifying New Drugs are Often Faulty," Science, 278(5340):1041-042 (1997).
Gutniak et al., "Antidiabetogenic Effect of Glucagon-Like Peptide-1 (7-36) Amide in Normal Subjects and Patients with Diabetes Mellitus," N. Engl. J. Med. 326:1316-1322 (1992).
Gygi et al., "Quantitative analysis of complex protein mixtures using isotope-coded affinity tags." Nat Biotechnol. 17(10):994-99 (Oct. 1999).
Halimi, "DPP-4 inhibitors and GLP-1 analogues: for whom? Which place for incretins in the management of type 2 diabetic patients?", Diabetes & Metabolism 34(Supplement 2):S91-S95 (Feb. 2008).
Hallas-Moller, "The Lente Insulins", Diabetes 5:7-14 (Jan.-Feb. 1956).
Hamilton et al., "Novel GLP-1 mimetics developed to treat type 2 diabetes promote progenitor cell proliferation in the brain" J Neurosci Res (2011) pp. 481-489, vol. 89.
Hamilton et al., "Receptors for the incretin glucagon-like peptide-1 are expressed on neurons in the central nervous system" Neuroreport(2009) vol. 20 No. 13, pp. 1161-1166.
Hanas et al., "2010 Consensus Statement on the Worldwide Standardization of the Hemoglobin A1C Measurement." Diabetes Care 33(8):1903-04 (Aug. 2010).
Hanefeld & Temelkova-Kurktschiev, "The postprandial state and the risk of atherosclerosis." Diabet Med. 14 Suppl 3:S6-11 (1997).
Hanefeld M. Normnahe postprandiale Hyperglykamie-eine essenzielle Komponente guter Diabeteskontrolle und Pravention kardiovaskularer Erkrankungen (Near-normal postprandial hyperglycemia—an essential component of good diabetes control and prevention of cardiovascular diseases). Paul Langerhans lecture 2007. Diabetologie und Stoffwechsel 2007; 2:362-369. in German with English abstract.
Hanna et al., Canadian Diabetes Association Clinical Practice Guidelines Expert Committee "Pharmacologic Management of Type 2 Diabetes" Canadian Journal of Diabetes, 27(Supp 2):S37-S42 (Dec. 2003).
Harkavyi & Whitton, "Glucagon-like peptide 1 receptor stimulation as a means of neuroprotection" British Journal of Pharmacology 159(3):495-501 (2010; Epub Jan. 29, 2010).
Harkavyi et al., "Glucagon-like peptide I receptor stimulation reverses key deficits in distinct rodent models of Parkinson's disease" J Neuroinftamm (2008) pp. 1-9, vol. 5, No. 19.
Harris "Clinical inertia in patients with T2DM requiring insulin in family practice." Can Fam Physician.56(12):e418-e424 (2010).
Hartmann et al., "Biological Activity of des-(B26-B30)-Insulinamide and Related Analogues in Rat Hepatocyte Cultures," Diabetologia 32(7):416-20 (1989).
Hasslacher et al., "Diabetic kidney disease" Exp and Clin Endocrinol Diabetes 122(7):391-94 (Jul. 2014).
Heile & Schneider, "The Evolution of Insulin Therapy in Diabetes Mellitus", J Fam Pract 61(5 Suppl.):S6-12 (May 2012).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).
Hellstrom et al., "T1388 GTP-010 as a Therapetuic Tool in IBS Pain Relief: Prospective, Randomized, Palebo-Controlled Study of a GLP-1 Analog", Gastroenterology, 134(4):A-544; Absract T1388 (Apr. 2008).
Higgins et al., "Oxidative Stress: Emerging Mitochondrial and Cellular Themes and Variations in Neuronal Injury", Journal of Alzheimer's Disease, 20:S453-S473 (2010).
Hillier & Pedula, "Characteristics of an adult population with newly diagnosed Type 2 Diabetes. The relation of obesity and age of onset." Diabetes Care 24(9):1522-27 (Sep. 2001).
Himeno et al., "Beneficial effects of exendin-4 on experimental polyneuropathy in diabetic mice" Diabetes (2011) pp. 2397-2406, vol. 60.
Hinds et al., "Synthesis and characterization of poly(ethylene glycol)-insulin conjugates." Bioconjugate Chem. 11(2):195-201 (Mar.-Apr. 2000).
Hinnen, "Therapeutic Options for the Management of Postprandial Glucose in Patients With Type 2 Diabetes on Basal Insulin" Clinical Diabetes 33(4):175-80 (2015).
HOE 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671 079.
Hollander & Kushner, "Type 2 Diabetes Comorbidities and Treatment Challenges: Rationale for DPP4-Inhibitors" Postgraduate Medicine, 122(3):71-80 (May 2010).
Holman et al., "10-Year Follow-up of Intensive Glucose Control in Type 2 Diabetes." N Engl J. Med. 359(15):1577-89 (2008).

(56) References Cited

OTHER PUBLICATIONS

Holman et al., "Three-year efficacy of complex insulin regimens in type 2 diabetes." N Engl J Med. 361(18):1736-47 (Oct. 2009; Epub Oct. 22, 2009).
Holscher "Incretin Analogues that have been Developed to Treat Type 2 Diabetes Hold Promise as a Novel Treatment Strategy for Alzheimer's Disease" Recent Patents on CNS Drug Discovery(2010) vol. 5 No. 2, pp. 109-117.
Holscher "The role of GLP-1 in neuronal activity and neurodegeneration" Vitamins and hormones 84:331-54 (2010).
Holscher "Development of Beta-Amyloid-induced neurodegeneration in Alzheimer's disease and novel neuroprotective strategies," Reviews in Neuroscience, 16:181-212 (2005).
Holscher "Possible Causes of Alzheimer's Disease: Amyloid Fragments, Free Radical, and Calcium Homeostasis" Neurobiology of Disease 5:129-41 (1998).
Holscher et al., "New roles for insulin-like hormones in neuronal signaling and protection: new hopes for novel treatments of Alzheimer's disease?" Neuro. Aging 31:1495-1502 (2008).
Holst & Vilsboll. "Combining GLP-1 receptor agonists with insulin: therapeutic rationales and clinical findings." Diabetes, Obesity and Metabolism 15(1):3-14 (2013).
Holst, "Glucagon-like Peptide-1, a Gastrointestinal Hormone with a Pharmaceutical Potential," Current Medicinal Chemistry 6:1005-17 (1999).
Home et al., "Insulin treatment: a decade of change," British Medical Bulletin, 1989, vol. 45, No. 1, pp. 92-110.
Home et al., "Management of type 2 diabetes: updated NICE guidance" BMJ 336: 1306-1308 (Jun. 2008).
http://diabetes.emedtv.com/lantus/generic-lantus.html; one page, last accessed Dec. 23, 2015.
Hubschle et al., "Anti-atherosclerotic activity of lixisenatide in ApoE knockout mice" Abstract 809, Diabetologia, 55(Supplement 1):S334 (Oct. 2012).
Humalog® prescribing information, Apr. 2012, pp. 1-6.
Hunter et al., "Drugs developed to treat diabetes. Liraglutide and lixisenatide, cross the blood brain barrier and enhance neurogenesis", BMC Neuroscience, (2012) vol. 13, p. 6.
IDF Clinical Guidelines Task Force. Global guideline for Type 2 diabetes. Brussels: International Diabetes Federation, pp. 1-82 (Aug. 2005).
IDF, International Diabetes Federation Guideline Development Group, "Guideline for management of postmeal glucose in diabetes" Diabetes Res Clin Pract, pp. 1-13, (2012).
Inpharma, Product News. "AVE0010 set to deliver in type 2 diabetes mellitus," Database Adisnews, retrieved from STN, Jun. 2008, pp. 1-3.
Insuman Infusat entry in Rote Liste, one page (2001).
Insuman Infusat; FASS Entry for Insuman Infusat; pp. 1-6 (Jan. 2000). English translation of Jun. 5, 2017, pp. 1-8 also submitted.
Insuman® Comb25 prescribing information, Feb. 2011, pp. 1-4.
Insuman® Infusat prescribing information, Feb. 2011, pp. 1-4.
International Search Report and Written Opinion received for PCT Patent Application No. PCT/EP2010/067249, dated Feb. 4, 2011.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/000018; dated Jun. 30, 2009, pp. 1-8.
International Search Report by the ISA for International Application No. PCT/EP2009/063195; dated May 6, 2010, one page.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-6.
International Search Report by the ISA for International Application No. PCT/EP2012/055660; dated May 10, 2012, pp. 1-15.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.
International Search Report by the ISA for International Application No. PCT/EP2015/079285; dated Mar. 9, 2016, pp. 1-7.
International Search Report by the ISA for International Application No. PCT/EP2016/050804; dated Mar. 4, 2016, pp. 1-4.
International Search Report by the ISA for International Application No. PCT/EP2016/055267; dated Jun. 7, 2016, pp. 1-8.
International Search Report by the ISA for International Application No. PCT/EP2016/055267; dated May 20, 2016, pp. 1-7.
International Search Report by the ISA for International Application No. PCT/EP2016/055954; dated Sep. 9, 2016, pp. 1-12.
Inzucchi et al. "Management of Hyperglycemia in Type 2 Diabetes: A Patient-Centered Approach" Diabetes Care, 35:1364-79 (Jun. 2012).
Inzucchi et al., "Management of hyperglycemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).
Isacson et al., "The glucagon-like peptide 1 receptor agonist exendin-4 improves reference memory performance and decreases immobility in the forced swim test" Eur J Pharmacal. 650(1):249-55 (Jan. 2011; Epub Oct. 14, 2010.).
Ismail-Beigi et al., "Individualizing Glycemic Targets in Type 2 Diabetes Mellitus: Implications of Recent Clinical Trials" Annals of Internal Medicine 154(8):554-559 (Apr. 2011).
ISPAD, International Diabetes Federation; "Global/IDF/ISPAD Guideline for Diabetes in Childhood and Adolescence," pp. 1-132 (2011).
Jackson et al., "Neutral regular insulin," Diabetes 21(4):235-45 (1972).
Jain, "Barriers to Drug Delivery in Solid Tumors," Scientific American, 271(1):58-65 (Jul. 1994).
Jang et al., "Neuroprotective Effects of *Triticum aestivum* L. against β-Amyloid-induced Cell Death and Memory Impairments" Phytother. Res. 24:76-84 (2010).
Janka et al., "Comparison of basal insulin added to oral agents versus twice-daily premixed insulin as initial insulin therapy for type 2 diabetes." Diabetes Care 28(2):254-59 (Feb. 2005).
Januvia—EPAR Summary for the Public, pp. 1-3 (Aug. 2012).

(56) References Cited

OTHER PUBLICATIONS

Jekel et al., "Use of endoproteinase Lys-C from Lysobacter enzymogenes in protein sequence analysis," Anal Biochem. 134(2):347-54 (1983).
Jendle et al., "Insulin and GLP-1 analog combinations in type 2 diabetes mellitus: a critical review." Expert Opin. Investig. Drugs 21(10):1463-74 (2012).
Jimenez et al., "Inflammatory Response in the Hippocampus of PS1M146L/APP751SL Mouse Model of Alzheimer's Disease: Age-Dependent Switch in the Microglial Phenotype from Alternative to Classic" Neurobiology of Disease, 28(45):11650-661 (2008).
Johnson et al., "Diabetes, Insulin Resistance, and Metabolic Syndrome in Horses" Journal of Diabetes Science and Technology, 6(3):534-40 (May 2012).
Johnson et al., "When is a unit of insulin not a unit of insulin? Detemir dosing in type 2 diabetes" Poster, one page, 2008. http://professional.diabetes.org/ContenUPosters/2008/p8-LB.pdf.
Jones et al. "Surfactant-Stabilized Protein Formulations: A Review of Protein-Surfactant interactions and Novel Analytical Methodologies," Therapeutic Protein & Peptide Delivery, ACS Symposium Series; Chapter 12, pp. 206-222 (1997).
Jones et al., "Effect of metformin in pediatric patients with type 2 diabetes: a randomized controlled trial." Diabetes Care 25(1):89-94 (Jan. 2002).
Jones, "Insulin Glargine Aventis Pharma", IDrugs 3(9):1081-87 (Sep. 2000).
Jorgensen et al., "Five fold increase of insulin concentration delays the absorption of subcutaneously injected human insulin suspension in pigs", Diabetes Research and Clinical Practice, 50:161-167 (2000).
Juniper et al., "Determining a minimal important change in a disease-specific quality of life questionnaire." J Clin Epidemiol 47(1):81-87 (Jan. 1994).
Kaarsholm et al., "Engineering stability of the insulin monomer fold with application to structure-activity relationships," Biochemistry 32(40):10773-8 (1993).
Kadima "Role of Metal Ions in the T- to R-Allosteric Transition in the Insulin Hexamer," Biochem. 38(41):13443-53 (Oct. 1999).
Kaduszkiewicz et al.., "Cholinesterase inhibitors for patients with Alzheimer's disease: systematic review of randomised clinical trials." BMJ 331:321 (2005).
Kaech & Banker, "Culturing hippocampal neurons" Nat Protoc. 1(5):2406-15 (2006).
Kahn et al., "Glycemic durability of rosiglitazone, metformin, or glyburide monotherapy." N Engl J. Med. 355(23):2427-43 (2006).
Kakhki et al., "Normal values of gallbladder ejection fraction using 99 mTc-sestamibi scintigraphy after a fatty meal formula." J Gastrointestin Liver Dis. 16(2):157-61 (Jun. 2007).
Kamisawa et al., "Pancreatographic investigation of pancreatic duct system and pancreaticobiliary malformation" J. Anal. 212(2):125-34 (2008).
Kanazawa et al., "Criteria and Classification of Obesity in Japan and Asia-Oceania", Asia Pacific J. Clin Nutr. 11 (Suppl. 7):S732-S737 (Dec. 2002).
Kang et al., "Subcutaneous Insulin Absorption Explained by Insulin's Physicochemical Properties-Evidence from Absorption Studies of Soluble Human Insulin and Insulin Analogues in Humans," Diabetes Care, 14(11):942-48 (Nov. 1991).
Kao et al., "The evaluation of gallbladder function by quantitative radionuclide cholescintigraphy in patients with noninsulin-dependent diabetes mellitus." Nucl. Med Commun.14(10):868-72 (1993).
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Kastin et al., "Entry of exedin-4 into brain is rapid but may be limited at high doses" International Journal of Obesity and Related Metabolic Disorders: Journal of the International Association for the Study of Obesity (2003) vol. 27 No. 3, pp. 313-318.
Kastin et al., "Interactions of Glucagon-like peptide (GLP-1) with blood brain barrier" Journal of Molecular Neuroscience (2001) pp. 7-14, vol. 18, No. 2.
Katakam et al., "Effect of Surfactants on the Physical Stability of Recombinant Human Growth Hormone" J Pharm Sci 84(6):713-16 (Jun. 1995).
Katz et al., "The clinical burden of type 2 diabetes in patients with acute coronary syndromes: Prognosis and implications for short- and long-term management" Diabetes and Vascular Disease Research, 11(6):395-409 (Nov. 2014).
Kelly et al., "Systematic review: glucose control and cardiovascular disease in type 2 diabetes." Ann Intern Med 151(6):394-403 (Sep. 2009; Epub Jul. 20, 2009).
Kemmler et al., "Studies on the Conversion of Proinsulin to Insulin," The Journal of Biological Chemistry, 246(22):6786-91 (1971).
Kendall et al., "Clinical Application of Incretin-Based Therapy: Therapeutic Potential, Patient Selection and Clinical Use." European Journal of Internal Medicine. 20(Suppl 2):S329-39 (Jul. 2009).
Kendall et al., "Effets of Exenatide (Exendin-4) on Glycemic Control Over 30 Weeks in Patients With Type 2 Diabetes Treated With Metformin and a Sulfonylurea" Diabetes Care 28:1083-91 (May 2005).
Kharkevich, "Pharmacology", 10th Ed., GEOTAR-Media, 2010, 908 pages, p. 42. [Russian w/ English translation].
Khaw et al., "Glycated haemoglobin, diabetes, and mortality in men in Norfolk cohort of European Prospective Investigation of cancer and Nutrition (EPIC Norfolk)." BMJ 322(7277):15-18 (Jan. 2001).
Kielgast et al., "Treatment of type 1 diabetic patients with glucagon-like peptide-1 (GLP-1) and GLP-1R agonists." Curr Diabetes Rev. 5(4):266-75 (Nov. 2009).
Kim et al, "Exendin-4 protects dopaminergic neurons by inhibition of microglial activation and matrix metalloproteinase-3 expression in an animal model of Parkinson's disease," J. Endocrin. 202:431-439 (2009).
Kim et al., "Retinopathy in Monkeys with Spontaneous Type 2 Diabetes" Investigative Opth & Visual Science, 45(12):4543-53 (Dec. 2004).
King et al., Global burden of diabetes, 1995-2025. Prevalence, numerical estimates and projections. Diabetes Care 21(9):1414-31 (Sep. 1998).
Knee et al., "A Novel Use of U-500 Insulin for Continuous Subcutaneous Insulin Infusion in Patients With Insulin Resistance: A Case Series", Endocrine Practice, 9(3):181-86 (May/Jun. 2003).
Knudsen et al., "Potent Derivatives of Glucagon-Like Peptide-1 With Pharmacokinetic Properties Suitable for Once Daily Administration", J. Med. Chem. 43(9):1664-69 (2000).
Kohn et al., "pi-shifted insulin analogs with extended in vivo time action and favorable receptor selectivity," Peptide 28:935-48 (2007).
Kohner "Diabetic retinopathy," British Medical Bulletin, vol. 45, No. 1, 1989, pp. 148-173.
Kolotkin et al., "Assessing impact of weight on quality of life." Obes Res. 3(1):49-56 (Jan. 1995).
Kolotkin et al., "Development of a brief measure to assess quality of life in obesity." Obes Res. 9(2):102-11 (Feb. 2001).
Kolterman et al., "Synthetic Exendin-4 (Exenatide) Significantly Reduces Postprandial and Fasting Plasma Glucose in Subjects with Type 2 Diabetes," J. Clin. Endocrine. Metab. 88(7):3082-89 (2003).
Korczyn and Nussbaum, "Emerging Therapies in the Pharmacological Treatment of Parkinson's Disease," Drugs 62:775-766 (2002).
Korytkowski, "When oral agents fail: practical barriers to starting insulin." Int J Obes Relat Metab Disord. 26 Suppl 3:S18-24 (Sep. 2002).
Krishnamurthy et al., Constancy and variability of gallbladder ejection fraction: impact on diagnosis and therapy. J Nucl Med. 45(11):1872-77 (Nov. 2004).
Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).
Langston et al., "Chronic Parkinsonism in Humans Due to a Product of Meperedine-Analog Synthesis" Science 219(4587):979-80 (1983).

(56) References Cited

OTHER PUBLICATIONS

Langui et al., "Subcellular Topography of Neuronal Aβ Peptide in APPxPS1 Transgenic Mice" American Journal of Pathology 165(5):1465-77 (2004).
Lantus®—FDA Drug Approval Label for Lantus® (NDA 02-1081) (Apr. 20, 2000) at https://www.accessdata.fda.gov/scripts/cder/daf/index.cfm?event=overview.process&ApplNo=021081 (accessed Jan. 25, 2018), pp. 1-14.
Lantus®—FDA Drug Approval Letter for Lantus® (NDA 02-1081) at https://www.accessdata.fda.gov/scripts/cder/daf/index.cfm?event=overview.process&ApplNo=021081 (accessed Jan. 25, 2018), pp. 1-5.
Lantus® 100U/ml solution for injection (insulin glargine); published in vol. 24 No. 9 of Pract. Diab. Int. Nov./Dec. 2007, p. 472.
Lantus® Annex I—Summary of product characteristics. Date of first authorisation: Jun. 9, 2000, pp. 1-164.
Lantus® Drug Description, downloaded Nov. 12, 2015, one page.
Lantus® entry in Physician's Desk Reference; pp. 1-6 (2001).
Lantus® prescribing information, May 2012, pp. 1-6.
Lantus® Product Information—European Medicines Agency, first published Aug. 5, 2009, pp. 1-2.
Larsen et al., "Combination of the insulin sensitizer, pioglitazone, and the long-acting GLP-1 human analog, liraglutide, exerts potent synergistic glucose-lowering efficacy in severely diabetic ZDF rats," Diabetes, Obesity and Metabolism, 10:301-311 (2008).
Larsen et al., "Sequence-Assisted Peptide Synthesis (SAPS)," J. Pept. Res. 52(6):470-76 (1998).
Laursen et al., "Enhanced monitoring of biopharmaceutical product purity using liquid chromatography-mass spectrometry." 1218(28):4340-48 (Jul. 2011; Epub May 2011).
Lawson et al., "Coordination of gastric and gallbladder emptying after ingestion of a regular meal." Gastroenterology. 85(4):866-70 (Oct. 1983).
Lee et al., "Goals of Glycemic Control in Frail Older Patients with Diabetes" JAMA 305(13):1350-51 (Apr. 2011).
Lee et al., "Ischemia-induced changes in glucagon-like peptide-1 receptor and neuroprotective effect of its agonist exendin-4, in experimental transient cerebral ischemia" J Neurosc Res (2009) pp. 1103-1113, vol. 89.
Lee et al., "Effect of Brij-78 on Systemic Delivery of Insulin from an Ocular Device" J Pharm Sci 86(4):430-33 (Apr. 1997).
Lee et al., "Review on the Systemic Delivery of Insulin via the Ocular Route" Int'l J Pharmaceutics 233(1-2):1-18 (Feb. 2002).
Lee, et al. (Sep. 30, 2015) "Epidemiology of diabetic retinopathy, diabetic macular edema and related vision loss", Eye and Vision, vol. 65, No. 1, pp. 1-25.
Leib et al., "Direct quantitation of peptide mixtures without standards using clusters formed by electrospray ionization mass spectrometry." Anal Chem. 81(10):3965-72 (May 2009).
Lens, "The terminal carboxyl groups of insulin," Biochimica et Biophysica Acta 3:367-70 (1949).
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Levemir® prescribing information, Dec. 2011, pp. 1-6.
Levene & Simms, "Calculation of isoelectric point," J Bioi Chern. 55:801-13 (1923).
Levin et al., "Combination therapy with insulin glargine and exenatide: real-world outcomes in patients with type 2 diabetes." Current Medical Research & Opinion 28(2):1-8 (2012).
Levine et al., "Oxidation of Methionine in Proteins: Roles in Antioxidant Defense and Cellular Regulation" IUBMB Life, 50:301-07 (Oct. 2000).
Leyer et al., "The role of the C-terminus of the insulin B-chain in modulating structural and functional properties of the hormone," Int J Pep Protein Res. 46(5):397-407 (1995).
Li & Holscher, "Common pathological processes in Alzheimer disease and type 2 diabetes: A review" Brain Research Reviews, 56:384-402 (2007).
Li et al., "Chronic treatment of exendin-4 affects cell proliferation and neuroblast differentiation in the adult mouse hippocampal dentate gyrus." Neurosci Lett 19:1205-19 (2010).
Li et al., "Enhancing the GLP-1 receptor signaling pathway leads to proliferation and neuroprotection in human neuroblastoma cells" Journal of Neurochemistry, 113:1621-631 (2010).
Lill, "Production of fast-acting insulins and delayed-release insulins—how can this problem be solved by technology? Insulin formulations," Pharmazie in unserer Zeit 30(1):56-61 (2001). (English Translation Included).
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposit ed, pp. 1-3.
Li et al., "GLP-1 receptor stimulation preserves primary cortical and dopaminergic neurons in cellular and rodent models of stroke and Parkinsons" PNAS (2009) pp. 1285-1290, vol. 106, No. 4.
Li et al., "GLP-1 Receptor Stimulation Reduces Amyloid-beta Peptide Accumulation and Cytotoxicity in Cellular and Animal Models of Alzheimer's Disease" J Alzheimers Dis (2010) pp. 1205-1219, vol. 19.
Insulinpraparat Wikipedia, http://de.wikipedia.org/wiki/Insulinpr%C3%A4parat, pp. 1-15 (Feb. 5, 2013).
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
Lotharius et al., "Effect of Mutant a-Synuclein on Dopamine Homeostasis in a New Human Mesencephalic Cell Line," Journal of Biological Chemistry, 277:38884-94 (2002).
Lotharius et al., "Progressive Degeneration of Human Mesencephalic Neuron-Derived Cells Triggered by Dopamine-Dependent Oxidative Stress Is Dependent onthe Mixed-Lineage Kinase Pathway," Journal of Neuroscience, 25:6329-42 (2005).
Lougheed et al., "Physical Stability of Insulin Formulations," Diabetes, 32(5):424-32 (May 1983).
Lougheed et al., "Insulin Aggregation in Artificial Delivery Systems" Diabetologia 19(1):1-9 (Jul. 1980).
Lovshin & Drucker, "Incretin-based therapy for type 2 diabetes mellitus." Nat. Rev. Endocrinol. 5(5):262-69 (May 2009).
Lyxumia®, 10 micrograms solution for injection, Summary of Product Characteristics, updated Oct. 31, 2014, pp. 1-12.
Lyxumia®, Annex I—Summary of product characteristics. Date of first authorisation: Feb. 1, 2013, pp. 1-92.
Lyxumia®, Chemical Subgroup A10BX, Community Register of Medicinal Products for Human Use, European Commission Public Health, p. 1-2 (May 2, 2013).
Lyxumia—, Product Information—European Medicines Agency, first published Mar. 14, 2013, pp. 1-2.
Mac Conell et al., "Exenatide resulted in significantly greater improvements in postprandial glycaemic control compared to sitagliptin," Diabetologia 51(Supplement 1) p. S348, Abstract 872, one page (2008).
Madsbad, "Impact of postprandial glucose control on diabetes-related complications: How is the evidence evolving?" Journal of Diabetes and Its Complications, 30:374-85 (2016; available online Oct. 9, 2015).
Mainous et al., "Impact of the population at risk of diabetes on projections of diabetes burden in the United States: an epidemic on the way." Diabetologia 50(5):934-40 (May 2007; Epub Nov. 21, 2006).
Mancuso et al., "Clinical features and pathogenesis of Alzheimer's disease: involvement of mitochondria and mitochondrial DNA," Adv Exp Med Biol., 685:34-44 (2010).
Manning et al., "Stability of Protein Pharmaceuticals," Pharm Research, 6(11):903-18 (Nov. 1989).

(56) References Cited

OTHER PUBLICATIONS

Marbury, et al., "A Pilot Study to Examine the Feasability of Insulin Glargine in Subjects With Impaired Fasting Glucose, Impaired Glucose Tolerance or New-Onset Type 2 Diabetes", Experimental and Clinical Endocrinology & Diabetes: Official Journal, German Society of Endocrinology and German Diabetes Associate, 116(5):282-88 (May 2008).
Margolis, "Diagnosis of Huntington's Disease," Ciin. Chem. 49:1726-32 (2003).
Markussen et al., "Soluble, prolonged-acting insulin derivatives. I. Degree of protraction and crystallizability of insulins substituted in the termini of the B-chain," Prot. Eng. 1(3), 1987, pp. 205-213.
Markussen et al., "Soluble, prolonged-acting insulin derivatives. II. Degree of protraction and crystallizability of insulins substituted in positions A17, B8, B13, B27 and B30," Prot. Eng. 1(3), 1987, pp. 215-223.
Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, pp. 157-166.
Martin et al. "Neurodegenation in excitotoxcity, global cerebral ischemia, and target deprivation: A perspective on the contributions of aptopsis and necrosis," Brain Res. Bull, 46:281-309 (1998).
Martin et al., "Exendin-4 improves glycemic control, ameliorates brain and pancreatic pathologies and extends survival in a mouse model of Huntington's Disease" Diabetes (2009) pp. 318-328, vol. 58, No. 2.
Mashkovsky et al., Lekarstvennye sredstva (Medicinal Drugs), Manual for Physicians, 2002, 1(14): 8-9. [Russian w/ English translation].
Matthews et al., "Homeostasis model assessment: insulin resistance and β-cell function from fasting plasma glucose and insulin concentrations in man." Diabetologia 28(7):412-419 (Jul. 1985).
Mattson "Calcium and neurodegeneration." Aging Cell 6:337-50 (2007).
McClean et al., "The diabetes drug Liraglutide prevents degenerative processes in a mouse model of Alzheimer's disease" Journal of Neuroscience 31(17):6587-94 (2011).
McClean. et al., "Glucagon-like peptide-1 analogues enhance synaptic plasticity in the brain: A link between diabetes and Alzheimer's disease" European Journal of Pharmacology (2010) pp. 158-162, vol. 630.
McFarlane, "Insulin therapy and type 2 diabetes: management of weight gain," J Clin Hypertens (Greenwich). 11(10):601-7 (Oct. 2009).
McKeage & Goa, "Insulin Glargine: A Review of its Therapeutic Use as Long-Acting Agent for the Management of Type 1 and Type 2 Diabetes Mellitus," Drugs 61(11):1599-1624 (Sep. 2001).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Mecklenburg & Guinn, "Complications of insulin pump therapy: the effect of insulin preparation," Diabetes Care 8 (4):367-70 (1985).
Medline Plus, "Obesity" available at http://www.nlm.nih.gov/medlineplus/obesity.html, Retrieved Aug. 22, 2013, one page.
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Meier et al., "Effect of lixisenatide vs liraglutide on glycaemic control, gastric emptying and safety parameters in optimised insulin glargine type 2 diabetes mellitus +/- metformin" Poster and Abstract 926, 50th EASD Annual Meeting, Vienna, Austria Sep. 15-19, 2014, pp. 1-3.
Meier, "GLP-1 receptor agonists for individualized treatment of type 2 diabetes mellitus." Nat. Rev. Endocrinol. 8:728-42 (2012).
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Merck Index, "Metformin", The Merck Index, 15th Edition (2013), RSC Publishing, 4 pages submitted, p. 1102.
Merrifield, "Solid Phase Synthesis." Science 232(4748):341-47 (1986).
Mikhail, "Is liraglutide a useful addition to diabetes therapy?" Endocr Practice 16(6):1028-37 (Nov.-Dec. 2010).
Miller et al., "Type 2 diabetes in the child and adolescent", In: Lifshitz F (ed) Pediatric Endocrinology: 5th edition, vol. 1, New York, Marcel Dekker, pp. 169-188 (2007).
Miyazaki et al., "Improved glycemic control and enhanced insulin sensitivity in type 2 diabetic subjects treated with pioglitazone", Diabetes Care, 24(4):710-19 (Apr. 2001).
Mokdad et al., "The association of body mass index with the risk of type 2 diabetes: a case-control study nested in an electronic health records system in the United States." JAMA, 289(1):76-79 (Jan. 2003).
Monnier & Colette, "Addition of rapid-acting insulin to basal insulin therapy in type 2 diabetes: indications and modalities." Diabetes Metab 32(1):7-13 (Feb. 2006).
Monnier et al., "Postprandial and Basal Glucose in Type 2 Diabetes: Assessment and Respective Impacts" Diabetes Technology & Therapeutics, 13(Supplement 1):S25-S32 (2011).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Monnier et al., The loss of postprandial glycemic control precedes stepwise deterioration of fasting with worsening diabetes. Diabetes Care. 30(2):263-69 (2007).
Moreno-Gonzalez et al., "Extracellular Amyloid-β and Cytotoxic Glial Activation Induce Significant Entorhinal Neuron Loss in Young PS1M146L/APP751SL Mice" Journal of Alzheimer's Disease 18:755-776 (2009).
Moretto et al., "Efficacy and Tolerability of Exenatide Monotherapy Over 24 Weeks in Antidiabetic Drug-Naive Patients with Type 2 Diabetes: A Randomized, Double-Blind, Placebo-Controlled, Parallel-Group Study", Clinical Therapeutics, 30(8):1448-60 (Aug. 2008).
Mudaliar & Edelman, "Insulin therapy in type 2 diabetes." Endocrinol Metab Clin North Am. 30(4):935-82 (Dec. 2001).
Muller et al., "Insulin Signaling in the Yeast *Saccharomyces cerevisiae*. 1. Stimulation of Glucose Metabolism and Snf 1 Kinase by Human Insulin," Biochemistry, 37(24):8683-95 (Jun. 1998).
Muzaffar et al., "The Mechanism of Enhanced Insulin Amyloid Fibril Formation by NaClIs Better Explained by a Conformational Change Model," PLoS One, Nov. 21, 2011, pp. 1-11, 6(11):e27906.
Nakagawa et al., "Receptor gene expression of glucagon-like peptide-1, but not of glucose-dependent insulinotropic polypeptide, in rat nodose ganglion cells" Auton Neurosci (2004) pp. 36-43, vol. 110.
Nathan et al., "Insulinotropic Action of Glucagon like Peptide-1-(7-37) in Diabetic and Nondiabetic Subjects," Diabetes Care 15(2):270-76 (1992).
Nathan et al., "Medical Management of Hyperglycemia in Type 2 Diabetes: A Consensus Algorithm for the Initiation and Adjustment of Therapy" Diabetes Care 32(1):193-203 (Jan. 2009).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008).
Nathan et al., "Management of hyperglycemia in type 2 diabetes mellitus: a consensus algorithm for the initiation and adjustment of therapy. Update regarding the thiazolidinediones." Diabetologia. 51(1):8-11 (2008).
Nathan et al., "Medical Management of Hyperglycemia in Type 2 Diabetes: A Consensus Algorithm for the Initiation and Adjustment of Therapy. A Consensus statement of the American Diabetes

(56) References Cited

OTHER PUBLICATIONS

Association and the European Association for the Study of Diabetes." Diabetes Care 31(1):173-75 (Jan. 2008).
Nathan et al., "Modern-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
Nathan et al., "Translating the A1c Assay Into Estimated Average Glucose values." Diabetes Care 31(8):1473-78 (Aug. 2008; Epub Jun. 7, 2008).
Nauck et al., "Glucagon-like peptide 1 (GLP-1) as a new therapeutic approach for type 2-diabetes," Exp Clin Endocrinol. Diabetes 105(4):187-95 (1997).
Nauck et al., "Comparative evaluation of incretin-based antidiabetic medications and alternative therapies to be added to melformin in the case of monotherapy failure," Journal of Diabetes Investigation 1(1-2):24-36 (Feb.-Apr. 2010).
Nauck et al., "Effects of Subcutaneous Glucagon-Like Peptide 1 (GLP-1 [7-36 Amide]) in Patients with NIDDM," Diabetologia 39(12):1546-53 (1996).
Nauck et al., "Glucagon-Like Peptide 1 and its Potential in the Treatment of Non-Insulin-Dependent Diaetes Mellitus," Horm. Metab. Res. 29(9):411-16 (1997).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
NCT00299871, ClinicalTrials.gov, "Dose Ranging Study of the GLP-1 Agonist AVE0010 in Metformin-Treated Subjects With Type 2 Diabetes Mellitus," last updated Jun. 22, 2010, Retrieved Nov. 7, 2011, pp. 1-3.
NCT00688701 Clinical Trials.gov "GLP-1 Receptor Agonist Lixisenatide in Patients with Type 2 Diabetes for Glycemic Control and Safety Evaluation in Monotherapy (Getgoal-Mono)" accessed Jul. 27, 2014; pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00713830, Clinical Trials.gov "GLP-1 Agonist in Patients with Type 2 Diabetes for Glycemic Control and Safety Evaluation, on Top of Sulfonylurea" pp. 1-3, accessed Mar. 16, 2016 (updated Jul. 13, 2008).
NCT00715624 Clinical Trials.gov "GLP-1 Agonist AVE0010 in Patients With Type 2 Diabetes for Glycemic Control and Safety Evaluation, on Top of Basal Insulin" (updated Mar. 2, 2011), p. 1-3.
NCT00715624 Clinical Trials.gov "GLP-1 Receptor Agonist Lixisenatide in Patients With Type 2 Diabetes for Glycemic Control and Safety Evaluation, on Top of Basal Insulin (Getgoal-L)" (2008-2014), p. 1-6 (Feb. 2011). D6 version.
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (Getgoal-P)" pp. 1-8 (Jun. 27, 2011).
NCT00765817, Clinical Trials.gov "Addition of Exenatide to Insulin Glargine in Type 2 Diabetes Mellitus" last updated Oct. 26, 2016, last accessed Jan. 19, 2018, pp. 1-8.
NCT00866658 ClinicalTrials.gov, "GLP-1 agonist AVE0010 in patients with type 2 diabetes for glycemic control and safety evaluation, on top of basal insulin +/- sulfonylurea" p. 1-3, accessed Mar. 16, 2016 (updated Aug. 3, 2010).
NCT00866658 ClinicalTrials.gov, "GLP-1 agonist AVE0010 in patients with type 2 diabetes for glycemic control and safety evaluation, on top of basal insulin +/- sulfonylurea" p. 1-3, accessed Mar. 16, 2016 (updated Jan. 19, 2010).
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01169779, Clinical Trials.gov, "Efficacy and Safety of Lixisenatide in Patients with Type 2 diabetes mellitus insufficiently controlled by metformin," pp. 1-3, accessed Mar. 16, 2016 (updated Mar. 28, 2011).
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01195454, NIH Clinical Trials, "Euglycemic clamp dose-response study comparing insulin glargine U300 with Lantus U100" last updated Sep. 3, 2010, pp. 1-3.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
Needleman et al., "A General Method Applicable to the Search for Similarities in the Amino Acid Sequence of Two Proteins," J. Mol. Biol. 48:443-453 (1970).
Neidle, "18.2 Failure Modes in the Discovery Process" Cancer Drug Design and Discovery, Elsevier/Academic Press, pp. 427-431 (2008).
Nettleton et al. "Characterization of the Oligomeric States of Insulin in Self-Assembly and Amyloid Fibril Formation by Mass Spectrometry," Biophysical J., v79, 2000, p. 1053-1065.
NHSC—National Horizon Scanning Center, "AVE0010 (ZP10) for type 2 diabetes mellitus" University of Birmingham, England; pp. 1-6 (Dec. 2008).
Nice, National Institute for Health and Care Excellence, "Evidence summary: new medicine, ESNM26: Type 2 diabetes: lixisenatide; Key points from the evidence" pp. 1-26 (Sep. 24, 2013).
Nice, National Institute for Health and Care Excellence, "Type 2 diabetes in adults: management" pp. 1-45 (Dec. 2, 2015).
Nicklas et al.., "Inhibition of NADH-Linked Oxidation in Brain Mitochondria by 1-Methyl-4-Phenyl-Pyridine, a Metabolite of the Neurotoxin, 1-Methyl-4-Phenyl-1,2,5,6-Tetrahydropyridine" Life Sciences 36:2503-508 (1985).
Nielsen et al., "Pharmacology of Exenatide (Synthetic Exendin-4): A Potential Therapeutic for Improved Glycemic Control of Type 2 Diabetes," Regul. Pept. 117(2):77-88 (2004).
Nih, National Institute of Diabetes and Digestive and Kidney Disease, "Hypoglycimia" pp. 1-8, accessed Mar. 16, 2016.
Nihonn-Iyakuhin-shu Iryoyaku "Pioglitazone hydrochloride, Insulin sensitizing hypoglycemic agent" 2009 Edition, Jiho Inc. p. 1901 (2009).
Nilsson et al., "Effects of GI vs content of cereal fibre of the evening meal on glucose tolerance at a subsequent standardized breakfast." Eur. J Clin Nutr. 62:712-20 (2008; epub May 23, 2007).

(56) References Cited

OTHER PUBLICATIONS

Noble et al., "Insulin Lispro: A Fast-Acting Insulin Analog," Am Fam Physician, 57(2):279-86 (1998).
Non-Final Office Action from U.S. Appl. No. 12/617,805; mailed Jul. 24, 2014, pp. 1-12.
Non-Final Office Action from U.S. Appl. No. 12/617,805; mailed May 2, 2012, pp. 1-11.
Non-Final Office Action from U.S. Appl. No. 12/617,805; mailed May 10, 2011, pp. 1-12.
Non-Final Office Action from U.S. Appl. No. 12/617,805; mailed Sep. 15, 2015, pp. 1-12.
Non-Final Office Action issued in U.S. Appl. No. 13/123,835; mailed Dec. 22, 2014, pp. 1-13.
Non-Final Office Action issued in U.S. Appl. No. 13/123,835; mailed Jul. 19, 2012, pp. 1-14.
Non-Final Office Action issued in U.S. Appl. No. 13/123,835; mailed May 28, 2015, pp. 1-11.
Non-Final Office Action issued in U.S. Appl. No. 13/602,913; mailed on Dec. 2, 2014, pp. 1-12.
Non-Final Office Action issued in U.S. Appl. No. 13/602,913; mailed on Jan. 13, 2014, pp. 1-53.
Non-Final Office Action issued in U.S. Appl. No. 13/602,913; mailed on May 17, 2013, pp. 1-7.
Non-Final Office Action issued in U.S. Appl. No. 15/146,255; mailed Sep. 18, 2017, pp. 1-10.
Non-Final Office Action issued in U.S. Appl. No. 15/275,867; mailed Jun. 1, 2017; pp. 1-11.
Non-Final Office Action issued in U.S. Appl. No. 15/340,969; mailed Jul. 24, 2017, pp. 1-6.
Non-Final Rejection in U.S. Appl. No. 13/633,496; mailed Apr. 21, 2016, pp. 1-12.
Non-Final Rejection in U.S. Appl. No. 13/633,496; mailed Apr. 29, 2013, pp. 1-53.
Non-Final Rejection in U.S. Appl. No. 13/633,496; mailed Apr. 6, 2015, pp. 1-14.
Non-Final Rejection in U.S. Appl. No. 13/633,496; mailed May 22, 2014, pp. 1-11.
Non-Final Rejection in U.S. Appl. No. 13/633,496; mailed May 25, 2017, pp. 1-10.
Non-Final Rejection in U.S. Appl. No. 13/633,563; mailed Dec. 1, 2014, pp. 1-9.
Non-Final Rejection in U.S. Appl. No. 13/633,563; mailed Jul. 1, 2013, pp. 1-56.
Non-Final Rejection in U.S. Appl. No. 13/633,563; mailed Jun. 4, 2014, pp. 1-11.
Non-Final Rejection in U.S. Appl. No. 13/633,563; mailed Oct. 6, 2015, pp. 1-12.
Non-Final Rejection in U.S. Appl. No. 13/633,563; mailed Oct. 5, 2016, pp. 1-12.
Non-Final Rejection issued in U.S. Appl. No. 14/995,910; mailed Dec. 11, 2017, pp. 1-7.
Non-Final Rejection issued in U.S. Appl. No. 12/617,811; mailed Apr. 27, 2011, pp. 1-10.
Non-Final Rejection issued in U.S. Appl. No. 12/617,811; mailed Jan. 14, 2015, pp. 1-15.
Non-Final Rejection issued in U.S. Appl. No. 12/617,811; mailed Jun. 21, 2012, pp. 1-7.
Non-Final Rejection issued in U.S. Appl. No. 12/617,811; mailed Oct. 27, 2011, pp. 1-13.
Non-Final Rejection issued in U.S. Appl. No. 13/110,568; mailed Mar. 19, 2012, pp. 1-18.
Non-Final Rejection issued in U.S. Appl. No. 13/310,118, mailed Mar. 29, 2013, pp. 1-21.
Non-Final Rejection issued in U.S. Appl. No. 13/310,118, mailed Mar. 25, 2015, pp. 1-15.
Non-Final Rejection issued in U.S. Appl. No. 13/310,118; mailed Mar. 19, 2012, pp. 1-19.
Non-Final Rejection issued in U.S. Appl. No. 13/363,956; mailed Apr. 10, 2013, pp. 1-15.
Non-Final Rejection issued in U.S. Appl. No. 13/363,956; mailed Feb. 11, 2015, pp. 1-18.
Non-Final Rejection issued in U.S. Appl. No. 13/363,956; mailed May 29, 2015, pp. 1-17.
Non-Final Rejection issued in U.S. Appl. No. 13/363,956; mailed Nov. 20, 2013, pp. 1-10.
Non-Final Rejection issued in U.S. Appl. No. 13/382,442; mailed Nov. 7, 2012, pp. 1-26.
Non-Final Rejection issued in U.S. Appl. No. 13/382,442; mailed Dec. 19, 2013, pp. 1-29.
Non-Final Rejection issued in U.S. Appl. No. 13/382,442; mailed Feb. 5, 2015, pp. 1-31.
Non-Final Rejection issued in U.S. Appl. No. 13/382,442; mailed Mar. 31, 2016, pp. 1-29.
Non-Final Rejection issued in U.S. Appl. No. 13/382,442; mailed Sep. 20, 2017, pp. 1-28.
Non-Final Rejection issued in U.S. Appl. No. 13/382,772; mailed Nov. 21, 2013, pp. 1-42.
Non-Final Rejection issued in U.S. Appl. No. 13/382,772; mailed Sep. 29, 2014, pp. 1-33.
Non-Final Rejection issued in U.S. Appl. No. 13/382,772; mailed Sep. 14, 2015, pp. 1-42.
Non-Final Rejection issued in U.S. Appl. No. 13/467,707; mailed Jul. 15, 2013, pp. 1-20.
Non-Final Rejection issued in U.S. Appl. No. 13/467,707; mailed Jul. 25, 2014, pp. 1-22.
Non-Final Rejection issued in U.S. Appl. No. 13/467,707; mailed Jun. 30, 2016, pp. 1-9.
Non-Final Rejection issued in U.S. Appl. No. 13/467,707; mailed Nov. 7, 2016, pp. 1-17.
Non-Final Rejection issued in U.S. Appl. No. 13/467,707; mailed Sep. 16, 2015, pp. 1-13.
Non-Final Rejection issued in U.S. Appl. No. 13/468,422; mailed Nov. 4, 2015; pp. 1-27.
Non-Final Rejection issued in U.S. Appl. No. 13/469,633; mailed Aug. 19, 2013, pp. 1-25.
Non-Final Rejection issued in U.S. Appl. No. 13/469,633; mailed Aug. 22, 2014, pp. 1-23.
Non-Final Rejection issued in U.S. Appl. No. 13/469,633; mailed Mar. 27, 2013, pp. 1-39.
Non-Final Rejection issued in U.S. Appl. No. 13/509,507; mailed Aug. 6, 2013, pp. 1-11.
Non-Final Rejection issued in U.S. Appl. No. 13/509,507; mailed Sep. 19, 2014, pp. 1-9.
Non-Final Rejection issued in U.S. Appl. No. 13/509,507; mailed Feb. 19, 2015, pp. 1-10.
Non-Final Rejection issued in U.S. Appl. No. 13/509,507; mailed Dec. 8, 2015, pp. 1-14.
Non-Final Rejection issued in U.S. Appl. No. 13/509,507; mailed Sep. 21, 2016, pp. 1-7.
Non-Final Rejection issued in U.S. Appl. No. 13/509,542; mailed May 23, 2013, pp. 1-21.
Non-Final Rejection issued in U.S. Appl. No. 13/509,542; mailed Apr. 2, 2014, pp. 1-20.
Non-Final Rejection issued in U.S. Appl. No. 13/509,542; mailed Aug. 11, 2015, pp. 1-30.
Non-Final Rejection issued in U.S. Appl. No. 13/509,542; mailed Nov. 23, 2016, pp. 1-34.
Non-Final Rejection issued in U.S. Appl. No. 13/595,590; mailed Jun. 5, 2015, pp. 1-9.
Non-Final Rejection issued in U.S. Appl. No. 13/595,590; mailed Oct. 16, 2013, pp. 1-7.
Non-Final Rejection issued in U.S. Appl. No. 13/595,590; mailed Sep. 5, 2014, pp. 1-10.
Non-Final Rejection issued in U.S. Appl. No. 13/661,476, mailed on Dec. 4, 2013, pp. 1-11.
Non-Final Rejection issued in U.S. Appl. No. 13/661,476, mailed on Mar. 6, 2014, pp. 1-28.
Non-Final Rejection issued in U.S. Appl. No. 13/661,476, mailed on Sep. 16, 2013, pp. 1-19.
Non-Final Rejection issued in U.S. Appl. No. 13/661,476; mailed Jun. 4, 2015, pp. 1-31.

(56) References Cited

OTHER PUBLICATIONS

Non-Final Rejection issued in U.S. Appl. No. 13/692,640; mailed May 6, 2014, pp. 1-10.
Non-Final Rejection issued in U.S. Appl. No. 13/692,640; mailed Oct. 31, 2013, pp. 1-10.
Non-Final Rejection issued in U.S. Appl. No. 13/700,631; mailed Apr. 22, 2013, pp. 1-27.
Non-Final Rejection issued in U.S. Appl. No. 13/700,631; mailed Dec. 17, 2015, pp. 1-18.
Non-Final Rejection issued in U.S. Appl. No. 13/700,631; mailed Nov. 18, 2014, pp. 1-22.
Non-Final Rejection issued in U.S. Appl. No. 13/700,631; mailed Nov. 29, 2013, pp. 1-23.
Non-Final Rejection issued in U.S. Appl. No. 13/819,114; mailed Dec. 2, 2015, pp. 1-14.
Non-Final Rejection issued in U.S. Appl. No. 13/819,114; mailed Jul. 31, 2014, pp. 1-9.
Non-Final Rejection issued in U.S. Appl. No. 14/172,151; mailed Mar. 24, 2015, pp. 1-16.
Non-Final Rejection issued in U.S. Appl. No. 14/172,151; mailed Jan. 19, 2017, pp. 1-20.
Non-Final Rejection issued in U.S. Appl. No. 14/220,562; mailed Apr. 8, 2015, pp. 1-18.
Non-Final Rejection issued in U.S. Appl. No. 14/303,895; mailed Mar. 24, 2017, pp. 1-17.
Non-Final Rejection issued in U.S. Appl. No. 14/303,895; mailed May 21, 2015, pp. 1-11.
Non-Final Rejection issued in U.S. Appl. No. 14/303,895; mailed Sep. 9, 2015, pp. 1-12.
Non-Final Rejection issued in U.S. Appl. No. 14/624,575; mailed Mar. 26, 2015, pp. 1-14.
Non-Final Rejection issued in U.S. Appl. No. 14/965,586; mailed Mar. 22, 2017, pp. 1-17.
Non-Final Rejection issued in U.S. Appl. No. 15/068,286; mailed Apr. 11, 2017, pp. 1-12.
Non-Final Rejection issued in U.S. Appl. No. 15/073,364; mailed Nov. 9, 2017, pp. 1-8.
Non-Final Rejection issued in U.S. Appl. No. 15/144,270; mailed Dec. 13, 2017, pp. 1-25.
Non-Final Rejection issued in U.S. Appl. No. 15/162,563; mailed Feb. 8, 2017, pp. 1-13.
Non-Final Rejection issued in U.S. Appl. No. 15/197,378; mailed Jun. 15, 2017, pp. 1-13.
Non-Final Rejection issued in U.S. Appl. No. 15/237,285; mailed Sep. 29, 2017, pp. 1-10.
Non-Final Rejection issued in U.S. Appl. No. 15/411,557; mailed Mar. 19, 2018, pp. 1-11.
Non-Final Rejection issued in U.S. Appl. No. 13/467,757; mailed Apr. 17, 2013, pp. 1-9.
Non-Final Rejection issued in U.S. Appl. No. 13/468,422; mailed Jun. 4, 2014, pp. 1-24.
Non-Final Rejection issued in U.S. Appl. No. 13/468,422; mailed Mar. 27, 2013, pp. 1-27.
Non-Final Rejection issued in U.S. Appl. No. 13/468,422; mailed Sep. 16, 2013, pp. 1-19.
Non-Final Rejection issued in U.S. Appl. No. 13/382,772; mailed Apr. 10, 2013, pp. 1-48.
Non-Final Rejection issued is U.S. Appl. No. 15/595,929; mailed Sep. 20, 2017, pp. 1-9.
Non-Final-Rejection issued in U.S. Appl. No. 13/432,811; mailed Apr. 8, 2013, pp. 1-7.
Non-Final-Rejection issued in U.S. Appl. No. 13/432,811; mailed Jul. 29, 2014, pp. 1-8.
Non-Final-Rejection issued in U.S. Appl. No. 13/432,811; mailed Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Nowels et al., "Validation of the EQ-50 quality of life instrument in patients after myocardial infarction." Qual Life Res 14(1):95-105 (Feb. 2005).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Olansky "Do incretin-based therapies cause acute pancreatitis?" J Diabetes Technol. 4(1):228-29 (Jan. 2010).
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov, "Glucagon-like Peptide-1, a New Hormone of the Entero-insular Axis," Diabetologia 35(8):701-711 (1992).
Osterbye et al., "Sulfatide promotes the folding of proinsulin, preserves insulin crystals, and mediates its monomerization." Glycobiology 11(6):473-79 (Jun. 2001).
Ott et al., "Diabetes in Germany" (DIG) study. "A prospective 4-year-follow-up study on the quality of treatment for type 2 diabetes in daily practice." Dtsch Med Wochenschr. 134(7):291-7 (2009). English Absract submitted.
Owens et al., "Pharmacokinetics of 125I-labeled insulin glargine (HOE 901) in healthy men: comparison with NPH insulin and the influence of different subcutaneous injection sites." Diabetes Care 23(6):813-19 (Jun. 2000).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Park et al., "PPARalpha agonis fenofibrate improves diabetic nephropathy in db/db mice," Kidney International, 69:1511-17 (published online Mar. 1, 2006).
Park et al., "Long-term treatment of glucagon-like peptide-1 analog exendin-4 ameliorates diabetic nephropathy through improving metabolic anomalies in db/db mice." J Am Soc Nephrol, 18(4):1227-38 (Apr. 2007; Epub Mar. 14, 2007).
Parkin "Guideline for Management of Postmeal Glucose" International Diabetes Federation, pp. 1-32 (Oct. 2007).
Partial International Search Report by the ISA for International Application No. PCT/EP2016/055954; dated Jun. 21, 2016, pp. 1-6.
Patel & Advance Collaborative Group, "Effects of a fixed combination of perindopril and indapamide on macrovascular and microvascular outcomes in patients with type 2 diabetes mellitus (the Advance trial): a randomised controlled trial." Lancet 370(9590):829-40 (2007).
Patel & Borchardt, "Chemical pathways of peptide degradation. II. Kinetics of deamidation of an asparaginyl residue in a model hexapeptide," Pharmaceutical Research 7(7):703-11 (1990).
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (Jan. 2011).
Pederson et al., "Improved Glucose Tolerance in Zucker Fatty Rats by Oral Administration of the Dipeptidyl Peptidase IV Inhibitor Isoleucine Thiazolidide." Diabetes 47(8):1253-58 (1998).
Perfetti "Combining basal insulin analogs with glucagon-like peptide-1 mimetics." Diabetes Technology & Therapeutics 13(9):873-81 (2011).
Perry et al., "A new Alzheimer's disease interventive strategy: GLP-1." Current Drug Targets;5(6):565-71 (Aug. 2004).
Perry et al., "A novel neurotrophic property of glucagon-like peptide 1: a promoter of nerve cell growth factor mediated differentiation on PC12 cells" J Pharmacol Exp (2002) pp. 958-966, vol. 300.
Perry et al., "Evidence of GLP-1-mediated neuroprotection in an animal model of pyridoxine-induced peripheral sensory neuropathy" Exp Neural (2007) pp. 293-301, vol. 203, No. 2.
Perry et al., "Protection and reversal of excitotoxic neuronal damage by glucagon-like peptide-1 and exendin-4" J Pharmacol Exp Ther (2002) pp. 881-888, vol. 302.
Perry et al., "The glucagon-like peptides: a double-edged therapeutic sword" Trends in Pharmacological Sciences (2003) pp. 377-383, vol. 24.

(56) References Cited

OTHER PUBLICATIONS

Petersen & Christensen et al., "Clinical potential of lixisenatide once daily treatment for type 2 diabetes mellitus" Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Pillion et al., "Dodecylmaltoside-mediated Nasal and Ocular Absorption of Lyspro-Insulin: Independence of Surfactant from Multimer Dissociation," Pharmaceutical Research, 15(10): 1637-39 (Oct. 1998).
Pinget et al., "Efficacy and Safety of Lixisenatide Once Daily Versus Placebo in Patients With Type 2 Diabetes Insufficiently Controlled on Pioglitazone (GetGoal-P)" Diabetes, 61(Supp 1):A258, Poster 1010-P (Jun. 2012).
Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (Nov. 2013; Epub May 26, 2013).
Pinhas-Hamiel & Zeitler, "Clinical presentation and treatment of type 2 diabetes in children." Pediatric Diabetes 8(9):16-27 (Dec. 2007).
Pi-Sunyer et al., "The effects of pharmacologic agents for type 2 diabetes mellitus on body weight". Postgrad Med. 120(2):5-17 (Jul. 2008).
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Pohl & Wank, "Molecular Cloning of the Heloderman and Exendin-4 cDNAs in the Lizard," J. Biol. Chem. 273(16):9778-84 (1998).
Porter et al., "Four weeks administration of Liraglutide improves memory and learning as well as glycemic control in mice with high fat dietary-induced obesity and insulin resistance" Diab Obes Metab (2010) pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini "Methods of measuring gallbladder motor functions—the need for standardization: scintigraphy." Dig Liver Dis. 35 Suppl 3:S62-6 (2003).
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Pugeat et al., "Insulin Resistance, Polycystic Ovary Syndrome and Metformin" Review Article, Drugs 1999; 58(Suppl 1):41-46 (Sep. 1999).
Quianzon & Shomali, "Lixisentide-Once Daily Glucagon-like Peptide-1 receptor Agonist in the Management of Type 2 Diabetes", US Endocrinology, 7(2):104-9 (Winter 2011).
Raccah et al., "When Basal Insulin Therapy in Type 2 Diabetes Mellitus is Not Enough—What Next?" Diabetes Metabolism Research and Reviews 23:257-64 (published online Feb. 21, 2007).
Raju et al., "Optimum Palliation of Inoperable Hilar Cholangiocarcinoma: Comparative Assessment of the Efficacy of Plastic and Self-Expanding Metal Stents," Dig Dis Sci. 56:1557-64 (published online, Jan. 11, 2011).
Raman & Heptulla, "New potential adjuncts to treatment of children with type 1 diabetes mellitus" Pediatric Research, 65(4):370-74 (Apr. 2009).
Ramos et al., "Early neuropathology of somatostatin/NPY GABAergic cells in the hippocampus of a PS1 x APP transgenic model of Alzheimer's disease" Neurobiology of Aging, 27:1658-1672 (2006).
Rao et al., "Is the combination of sulfonylureas and metformin associated with an increased risk of cardiovascular disease or all-cause mortality? A meta-analysis of observational studies." Diabetes Care. 31(8):1672-8 (2008).
Ratner et al. "Dose-dependent effects of the once-daily GLP-1 receptor agonist lixisenatide in patients with Type 2 diabetes inadequately controlled with metformin: a randomized double-blind, placebo-controlled trial," Diabetic Med. 27(9):1024-1032 (Sep. 2010).
Ratner et al. Abstract 131 "Post-meal pharmacodynamics profile of AVE0010, a once-daily GLP-1 receptor agonist, in patiens with type 2 diabetes inadequately controlled on metformin" Diabetologia 52(Suppl. 1): S60, #131 (Sep. 2009).
Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Ratner et al., Poster "A dose-finding study of the new GLP-1 agonist AVE0010 in Type 2 Diabetes insufficiently controlled with metformin.", Diabetes, 57:Suppl.1, A129, Abstract No. 433-P, 68th Annual Meeting of the American Diabetes Association, San Francisco, Jun. 6-10, 2008.
Raufman "Bioactive peptides from lizard venoms," Regul Pept 61(1):1-18 (1996).
Ray et al., "Effect of intensive control of glucose on cardiovascular outcomes and death in patients with diabetes mellitus: a meta-analysis of randomized controlled trials." Lancet 373(9677):1765-72 (May 2009).
Register of medicaments (RM), 2003, issue 10, p. 517.
Remington: The Science and Practice of Pharmacy, Twentieth Edition, Lippincott Williams & Wilkins, USA, "Oral Hypoglycemic and Hyperglycemic Drugs" pp. 1373 and 1375; 2000.
Remington: The Science and Practice of Pharmacy, Twentieth Edition, Lippincott Williams & Wilkins, USA, "Pancreatic Disorders" pp. 1081-1082 and "Metformin Hydrochloride" p. 1375; 2000.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle et al., "Adding Once-Daily Lixisenatide for Type 2 Diabetes Inadequately Controlled with Newly Initiated and Continuously Titrated Basal Insulin Glargine: a 24-week, randomized, placebo-controlled study (GetGoal-Duo 1)" Diabetes Care, pp. 2497-2503 (Sep. 2013).
Riddle et al., "The treat-to-target trial: randomized addition of glargine or human NPH insulin to oral therapy of type 2 diabetes patients." Diabetes Care 26(11):3080-86 (Nov. 2003).
Riddle et al., Adding once-daily Lixisenatide for Type 2 Diabetes inadequately controlled by established basal insulin: a 24-week, randomized, placebo-controlled comparison (GetGoal-L). Diabetes Care 36(9):2489-96 (Sep. 2013).
Riddle et al., Contributions of Basal and Postprandial Hyperglycemia Over a Wide Range of A1C Levels Before and After Treatment Intensification in Type 2 Diabetes, Diabetes Care 34:2508-2514 (published online Oct. 25, 2011).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Ritzel et al., "A Synthetic Glucagon-Like Peptide-1 Analog with Improved Plasma Stability," J. Endocrine. 159(1):93-102 (1998).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-59 (Sep./Oct. 2009).
Rohrmann, "Differential Diagnosis of Pancreatic and Biliary Duct Diseases," Diseases of the Abdomen and Pelvis Syllabus, pp. 170-174 (1999).
Rosenstock et al., "Benefits fo a fixed-ratio formulation of once-daily insulin glargine/lixisenatide (LixiLan) vs glargine in type 2 diaebtes inadequately controlled on metformin", Clinical Trial Registration No. NCT01476475, Abstract, 2014, p. 241.
Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).

(56) References Cited

OTHER PUBLICATIONS

Rosenstock et al., Abstract, 564P "Post-meal effects of AVE0010, a once-daily GLP-1 receptor agonist, in type 2 diabetes inadequately controlled on metformin," Diabetes 58(Suppl.1):A151-A152 (Jun. 1, 2009).
Rosenstock et al., OP 25 GLP-1 Based therapies, Abstract 145 "Dose range effects of the new once daily GLP-1 receptor agonist AVE0010 added to metformin in type 2 diabetes," Diabetologia 51 (Supplement 1):S66 (Sep. 2008).
Rosenstock et al., Poster "Efficacy and safety of lixisenatide once daily vs exenatiide twice daily in type 2 DM inadequately controlled on metformin (GetGoal-X)." 71st Scientific Sessions (Nov. 2011).
Rosenstock J et al., Advancing Basal Insulin Glargine with Prandial Lixisenatide QD vs. Insulin Glulisine QD or TID in T2DM: The GetGoalDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Rubino et al., "Delayed initiation of subcutaneous insulin therapy after failure of oral glucose-lowering agents in patients with type 2 diabetes: a population-based analysis in the UK." Diabet Med. 24(12):1412-18 (2007).
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones & Khan, Insulin-associated weight gain in diabetes: causes, effects and coping strategies. Diabetes Obes Metab.9(6):799-812 (Nov. 2007).
Russell-Jones, "Current developments in the treatment of diabetes: the incretin therapies" Br J Diabetes Vasc Dis. 10:21-30 (Feb. 2010).
Sacks et al., "Guidelines and Recommendations for Laboratory Analysis in the Diagnosis and Management of Diabetes Mellitus." Clinical Chemistry 48(3):436-72 (Mar. 2002).
Sampson et al., "Second symposium on the definition and management of anaphylaxis: summary report—Second National Institute of Allergy and Infectious Disease/Food Allergy and Anaphylaxis Network symposium." Journal of Allergy and Clinical Immunology, 117(2):391-397 (2006).
Sanger et al., The amide groups of insulin, Biochem J. 59(3):509-18 (1955).
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi Aventis, "A randomized, double-blind, euglycemic glucose clamp study of four formulations of SAR161271, in single doses in healthy subjects and sinlge ascending doses in patients with Type 1 diabetes mellitus", Jun. 4, 2012, Retrieved from url: <https://www.sanofi.com/assets/dotcom/content-app/clinical-studies/pharma/Letter-N/TDU10987_summary.pdf>.
Sanofi Presentation, "Natixis Conference on Diabetes" Pierre Chancel, pp. 1-23, Nov. 8, 2011.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.

Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi Press Release entitled "FDA Accepts Sanofi's New Drug Application for Basal Insulin Toujeo®," dated Jul. 8, 2014, pp. 1-2.
Sanofi Press Release entitled "Sanofi Announces Top-Line Results for Cardiovascular Outcomes Study of Lyxumia® (lixisenatide).", dated Mar. 19, 2015, Paris, France, pp. 1-2.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release (Melia), "New Diabetes Compound AVE0010 Showed Clear Dose Response Results With Once-A-Day Injection in Phase IIb Study" San Francisco, California (Jun. 7, 2008) pp. 1-3.
Sanofi-aventis Press Release (Peron and Schaeffer), "Sanofi-aventis Announces Positive Top-line Lixisentatide Phase III Results" Paris, France (Feb. 2, 2011) pp. 1-2.
Sanofi-aventis Press Release, "A promising R&D portfolio, well positioned to deliver future growth" (dated Sep. 17, 2007) pp. 1-11.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi-aventis Press Release, "Once Daily Lixisenatide in Combination with Basal Insulin Demonstrates Significant Improvement in Glucose Control" Paris, France (Sep. 30, 2010) pp. 1-3.
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release entitled "Sanofi Receives FDA Approval of Once-Daily Basal Insulin Toujeo®," dated Feb. 26, 2015, pp. 1-4.
Schapira, "Causes of neuronal death in Parkinson's disease." Adv Neurol 86:155-162 (2001).
Schellenberger et al., "Attempts for Quantifying the S' Subsite Specificity of Serine Proteases," Selected Papers Presented at the 2nd International Meeting on the Molecular and Cellular Regulation of Enzyme Activity, Advances in the Biosciences, Peptides and Proteases: Recent Advances 65:159-66 (1987).
Schellenberger et al., "Protease-Catalyzed Kinetically Controlled Peptide Synthesis," Angewante Chemie, International Edition 30(11):1437-49 (1991).
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Schindowski et al., "Impact of Aging: Sporadic, and Genetic Risk Factors on Vulnerability to Apoptosis in Alzheimer's Disease" NeuroMolecular Medicine, 4:161-177 (2003).
Schmitz et al., "Hippocampal Neuron Loss Exceeds Amyloid Plaque Load in a Transgenic Mouse Model of Alzheimer's Disease" American Journal of Pathology, 164(4):1495-1502 (2004).
Schmolka, "Poloxamers in the Pharmaceutical Industry" in Polymers for Controlled Drug Delivery, Chapter 10, pp. 189-214 (CRC Press) (1991).
Schubert-Zsilavecz et al., "Better blood sugar control in diabetics. Insulin glargin—a long acting insulin analogue," Pharmazie in Unserer Zeit 30(2):125-30 (2001). With English translation.
Schwartz et al., "A superactive insulin: [B10-Aspartic acid]insulin(human)," Proc. Natl. Acad. Sci. USA, 84(18):6408-11 (Sep. 1987).

(56) References Cited

OTHER PUBLICATIONS

Schwartz et al., "New Equations to Estimate GFR in Children with CKD." J Am Soc Nephrol. 20(3):629-37 (Mar. 2009; epub Jan. 21, 2009).
Search Report in Chinese Patent Application No. 201410818149.0; dated Jan. 10, 2017, pp. 1-3. English translation submitted.
Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Search Report of the Intellectual Property Office of Singapore for Patent Application No. 10201403840V; search completed Nov. 21, 2017 and mailed Jan. 4, 2017, pp. 1-3.
Search Report of the Intellectual Property Office of Singapore for Patent Application No. 10201500871T, dated Nov. 2, 2015, pp. 1-3.
Secnik Boye et al., "Patient-reported outcomes in a trial of exenatide and insulin glargine for the treatment of type 2 diabetes," Health and Quality of Life Outcomes, vol. 4, No. 80, pp. 1-8 (Oct. 2006).
Seino et al., "Lixisenatide significantly improves glycemic control in Asian patients with T2DM insufficiently controlled on basal insulin ± SU." Diabetes, Abstract book for 71st Scientific Session. p. A76; Abstract 278-OR (2011).
Seino et al., "Randomized, double-blind, placebo-controlled trial of the once-daily GLP-1 receptor agonist lixisenatide in Asian patients with type 2 diabetes insufficiently controlled on basal insulin with or without a sulfonylurea (GetGoal-L-Asia)." Diabetes, Obesity and Metabolism 14(10):910-17 (2012).
Seino et al., and the Committee of Japan Diabetes Society on the diagnostic criteria of diabetes mellitus. "Report of the committee on the classification and diagnostic criteria of diabetes mellitus." Journal of the Japan Diabetes Society. 53:450-467 (2010). In Japanese, English translation of selected passages provided.
Sharplin et al., "Improved glycaemic control by switching from insulin NPH to insulin glargine: a retrospective observational study," Cardiovascular Diabetology, 8(3):1-8 (published Jan. 19, 2009).
Shaw et al., "US valuation of the EQ-5D health states: development and testing of the D1 valuation model." Med Care 43(3):203-20 (Mar. 2005).
Shehadeh et al., "Can GLP-1 preparations be used in children and adolescents with diabetes mellitus?" Pediatric Endocrinology Reviews, 11(3):324-27 (Mar. 2014).
Sherer et al., "Subcutaneous Rotenone Exposure Causes Highly Selective Dopaminergic Degeneration and a-Synuclein Aggregation," Experimental Neurology, 179:9-16 (2003).
Shi, "The Newest Handbook of Clinical Drugs" Military Medical Science Press, p. 809, (Jan. 2008). English translation submitted.
Sillars et al., "Sulphonylurea-metformin combination therapy, cardiovascular disease and all-cause mortality: the Fremantle Diabetes Study." Diabetes Obes Metab. 12(9):757-65 (Sep. 2010).
Sloop et al., "Glucagon as a target for the treatment of Type 2 diabetes." Expert Opin Ther Targets. 9(3):593-600 (Jun. 2005).
Sluzky et al., "Kinetics of Insulin Aggregation in Aqueous Solutions Upon Agitation in the Presence of Hydrophobic Surfaces," Proc. Natl. Acad. Sci. USA. 88(21):9377-81 (Nov. 1991).
Smolka et al., "Optimization of the isotope-coded affinity tag-labeling procedure for quantitative proteome analysis." Anal Biochem. 297(1):25-31 (Oct. 2001). Abstract only submitted.
Soeborg et al., "Absorption kinetics of insulin after subcutaneous administration" European Journal of Pharmaceutical Sciences 36(1):78-90 (Jan. 2009; Epub Nov. 5, 2008).
Spasov & Chepurnova, "Scientific Approaches to Combination Therapy for Type 2 Diabetes Mellitus," Bulletin of Volgograd State Medical University, 1(37):8-10 (2011). See English Abstract.
Spertus et al., "Development and evaluation of the Seattle Anginal Questionnaire: a new functional status measure for coronary artery disease." J Am Coli Cardiol. 25(2):333-41 (Feb. 1995).
Spertus et al., "Health status predicts long-term outcome in outpatients with coronary disease." Circulation. 106(1):43-49 (Jul. 2002).
Spertus et al., "Monitoring the quality of life in patients with coronary heart disease." Am J Cardiol. 74(12):1240-44 (Dec. 1994).
Sporn & Suh, "Chemoprevention of cancer" Carcinogenesis, 21(3):535-530 (2000).
Srinivasan & Ramarao, "Animal models in type 2 diabetes research: An overview." Indian J Med Res. 125:451-472 (Mar. 2007).
St. John Providence Health Center, "Preventing Obesity" http://www.stjohnprovidence.org/HealthInfolib/swarticle.aspx?type=85&id=P07863, Retrieved Aug. 22, 2013, pp. 1-2.
Standardized Definitions for Cardiovascular Outcomes Trials: Draft Recommendations. Division of Metabolism and Endocrinology Products. Center for Drug Evaluation and Research (CDER). pp. 1-34, Mar. 24, 2010.
Starkova, ed., "Clinical Endocrinology", Guide for physicians, Moscow, "Medicine", 1991, p. 192-262.
Stolk et al., "Insulin and cognitive function in an elderly population. The Rotterdam Study." Diabetes Care, 20:792-95 (1997).
Stumvoll et al., "Type 2 diabetes: Principles of pathogenesis and therapy." Lancet 365(9467):1333-46 (Apr. 2005).
Summary of Product Characteristics Lyxumia 10 micrograms solution for injection, pp. 1-93, published Mar. 14, 2013.
Sundby "Separation and Characterization of Acid-Induced Insulin Transformation Products by Paper Electrophoresis in 7 M Urea," J. Biol. Chem. 237(11):3406-11 (Nov. 1962).
Sutter Medical Foundation, "Type 2 Diabetes Adult Outpatient Insulin Guidelines" Feb. 2011, pp. 1-6.
Tang, "Biotech Drugs—Introduction and Practice Handbook" Chemical Industry Press, pp. 635-636, (Jan. 2008). English translation submitted.
Tanner & Davies, "Clinical longitudinal standards for height and height velocity for North American children." J Pediatr. 107(3):317-29 (Sep. 1985).
Tanner et al., "Rotenone, Paraquat, and Parkinson's Disease," Environmental Health Perspectives, 119:866-872 (2011).
Tanner et al., "Standards from birth to maturity for height, weight, height velocity, and weight velocity: British children, Part II." Arch Dis Child. 41(220):613-35 (1966).
Tempero, "How I treat Pancreatic Ductal Adenocarcinoma," Current Clinical Issues, Journal of Oncology Practice, vol. 4, Issue 1, pp. 46-47 (2008).
Teramoto et al., "Exendin-4, a glucagon-like peptide-1 receptor agonist, provides neuroprotection in mice transient focal cerebral ischemia" J Cerebr Blood Flow Metab (2011) pp. 1696-1705, vol. 31, No. 8.
Tessari et al., "Insulin in Methionine and Homocysteine Kinetics in Healthy Humans: Plasma Vs. Intracellular Models", Am J. Physiol Endocrine Metab 288(6):E1270-E1276 (2005).
Tetich et al., "Neuroprotective effects of (24R)-1,24-dihydroxycholecalciferol in human neuroblastoma SH-SY5Y cell line" J Steroid Biochemistry & Molecular Biology 89-90:365-70 (2004).
Tews et al., "Enhanced protection against cytokine- and fatty acid-induced apoptosis in pancreatic beta cells by combined treatment with glucagon-like peptide-1 receptor agonists and insulin analogues." Horm Metab Res. 40(3):172-80 (Mar. 2008).
Tews et al., Abstract of Oral Presentation "Enhanced Protection Against Cytokine- and Fatty Acid-induced Apoptosis in Ins-1 Beta-Cells by Combined Treatment with Insulin Glargine and the Novel GLP-1 Receptor Agonist AVE0010" Diabetes, 56(Suppl. 1):A72-A73 (2007).
The Advance Collaborative Group, "Intensive blood glucose control and vascular outcomes in patients with type 2 diabetes." N Engl J Med 358(24):2560-72 (Jun. 2008).
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
The Diabetes Control and Complications Trial Research Group, "The Effect of Intensive Treatment of Diabetes on the Development and Progression of Long-Term Complications in Insulin-Dependent Diabetes Mellitus", The New England Journal of Medicine, 329:977-86 (Sep. 1993).

(56) References Cited

OTHER PUBLICATIONS

Thong et al., "Safety, efficacy and tolerability of exenatide in combination with insulin in the Association of British Clinical Diabetologists nationwide exenatide audit." Diabetes, Obesity and Metabolism 13:703-10 (2011).
Thurow & Geisen, "Stabilisation of dissolved proteins against denaturation at hydrophobic interfaces," Diabetologia, 27(2):212-18 (Aug. 1984).
Tirosh et al., "Normal Fasting Plasma Glucose Levels and Type 2 Diabetes in Young Men" New England Journal of Medicine, 353(14):1454-62 (Oct. 2005).
Toth et al., "Neurite sprouting and synapse deterioration in the aging Caenorhabditis elegans nervous system" J Neurosci. 32(26):8778-90 (2012).
Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 750, 753 and 754 of Igaku No Ayumi, "Incretin Receptors," May 2010, vol. 233; No. 9: 750-754, pp. 1-4.
Turner et al., UK Prospective Diabetes Study (UKPDS) Group "Glycemic control with diet, sulfonylurea, metformin, or insulin in patients with type 2 diabetes mellitus: Progressive requirement for multiple therapies (UKPDS 49)." JAMA 281(21):Dec. 2005 (1999).
Tyler-Cross Schirch, "Effects of amino acid sequence, buffers, and ionic strength on the rate and mechanism of deamidation of asparagine residues in small peptides," J Biol Chem. 266(33):22549-56 (1991).
UK Prospective Diabetes Study (UKPDS) Group 28: A randomized trial of efficacy of early addition of metformin in sulfonylurea-treated type 2 diabetes. Diabetes Care, 21(1):87-92 (Jan. 1998).
UK Prospective Diabetes Study (UKPDS) Group, "Intensive blood-glucose control with sulphonylureas or insulin compared with conventional treatment and risk of complications in patients with type 2 diabetes (UKPDS 33)" Lancet 352(9131):837-53 (Sep. 1998).
UK Prospective Diabetes Study (UKPDS) Group, "Effect of intensive blood-glucose control with metformin on complications in overweight patients with type 2 diabetes (UKPDS 34)." Lancet 352(9131):854-65 (Sep. 1998).
UK Prospective Diabetes Study (UKPDS) Group, "Tight blood pressure control and risk of macrovascular and microvascular complications in type 2 diabetes (UKPDS 38)." BMJ 317:703-13 (Sep. 1998).
Uttenthel et al., "Molecular forms of flucagon-like peptide-1 in human pancreas and glucagonomas," J. Clin. Endocrinol. Metabol. 61(3):472-79 (1985).
Valle et al., "Cisplatin plus Gemcitabine versus Gemcitabine for Biliary Tract Cancer," N Engl J Med. 362(14):1273-81 (Apr. 2010).
Van Delden, "Pancreas-Carcinoma, CT Assessment of Resectability," Radiology Department of the Academical Medical Centre, pp. 1-12 (Apr. 2006).
Van Gaal & De Leeuw, "Rationale and options for combination treatment of type 2 diabetes." Diabletogia 46(Supplement 1):M44-M50 (Mar. 2003).
Van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
Varadarajan et al., "Review: Alzheimer's Amyloid b-Peptide-Associated Free Radical Oxidative Stress and Neurotoxicity," Journal of Structural Biology, 130:184-208 (2000).
Venezia et al., "Apoptotic cell death and amyloid precursor protein signaling in neuroblastoma SH-SY5Y cells," Ann NY Acad Sci., 1030:339-47 (2004).
Victoza Press Release, "Diabetes drugs show promise in Alzheimer's" published Jan. 17, 2011, pp. 1-2.
Victoza® Annex I—Summary of product characteristics. First published 2009, pp. 1-32.
Victoza® Product information—European Medicines Agency, first published Aug. 7, 2009, pp. 1-2.
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
Volund et al., "In Vitro and In Vivo Potency of Insulin Analogues Designed for Clinical Use," Diab. Med. 8(9):839-47 (Nov. 1991).
Vora et al., "Incretin-based therapy in combination with basal insulin: A promising tactic for the treatment of type 2 diabetes." Diabetes & Metab. 39(1):6-15 (2013).
Wafa et al., "Use of U-500 Regular Insulin in Type 2 Diabetes", Diabetes Care, 29(9):2175-2176 (2006).
Wahlin-Boll et al., "Impaired effect of sulfonylurea following increased dosage." Eur J Clin Pharmacol 22(1):21-25 (1982).
Wajchenberg, Chapter 23 "Clinical Approaches to preserve beta-cell function in Diabetes", Adv Exp Med Biol. 654:515-35 (2010).
Wan et al., "Enhancing the Activity of Insulin at the Receptor Interface: Crystal Structure and Photo-Cross-Linking of A8 Analogues," Biochemistry 43:16119-33 (2004).
Wang et al., "Real-world outcomes of US employees with type 2 diabetes mellitus treated with insulin glargine or neutral protamine Hagedorn insulin: a comparative retrospective database study." BMJ Open. 3:e002348 (2013), pp. 1-9.
Wang, "Instability, Stabilization and Formulation of Liquid Protein Pharmaceuticals," Int'l J Pharm, 185(2):129-88 (Aug. 1999).
Ward "Diabetic neuropathy," British Medical Bulletin, 45(1):111-26 (Jan. 1989).
Watson et al., "Insulin increases CSF Aβ42 levels in normal older adults" Neurology 60:1899-1903 (2003).
Weir "Glucagon-like peptide-1 (7-37) actions on endocrine pancreas." Diabetes 38(3):338-42 (Mar. 1989).
Weiss et al., "Activities of Monomeric Insulin Analogs at Position A8 Are Uncorrelated With Their Thermodynamic Stabilities", The Journal of Biological Chemistry 276(43):40018-24 (2001).
Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India Esicon (2007) (2 pages including Abstract and Poster).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
Werner, "Preclinical pharmacology of the new GLP-1 receptor agonist AVE0010", Ann. Endocrinol. (Paris), 69(2):164-65 (Apr. 2008).
Weyer et al., "Long-term changes in insulin action and insulin secretion associated with gain, loss, regain and maintenance of body weight", Diabetologia, (43)1:36-46 (Jan. 2000).
White et al., "Randomized clinical trials with added rescue medication: some approaches to their analysis and interpretation." Statistics in Medicine 20:2995-3008 (2001).
Whittingham et al., "Insulin at PH2: Structural Analysis of the Conditions Promoting Insulin Fibre Formation" J. Mol. Biol., (2002), vol. 318, pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
WHO Rational Use of Medicines, http://www.who.int/medicines/areas/rational_use/en/ downloaded Dec. 18, 2014 10:02:48 AM (2012).

(56) References Cited

OTHER PUBLICATIONS

WHO, World Health Organization Media Center. Diabetes Fact Sheet. Available from: http://www.who.int/mediacentre/factsheets/fs312/en/index.html. Accessed Jun. 13, 2016, pp. 1-6.
WHO, World Health Organization Media Center. Obesity and overweight, Fact Sheet No. 311. Updated Jan. 2015, pp. 1-5.
Widjaja et al., "UKPDS 20: plasma leptin, obesity, and plasma insulin in type 2 diabetic subjects." J Clin Endocrinol Metab. 82(2):654-7 (1997).
Wiernsperger, et al. "The Antihyperglycaemic Effect of Metformin Therapeutic and Cellular Mechanisms" Review Article, Drugs 1999:58(Suppl 1):31-39 (Sep. 1999).
Wikipedia® entry for "Body mass index" Retrieved from the Internet: https://en.wikipedia.org/wiki/Body mass_index pp. 1-14, retrieved Feb. 26, 2016.
Wikipedia® entry for "Lixisenatide" Retrieved from the Internet: https://en.wikipedia.org/wiki/Lixisenatide pp. 1-2, last updated Dec. 2015.
Wikipedia® entry for "Metformin" Retrieved from the Internet: https://en.wikipedia.org/wiki/Metformin pp. 1-21, retrieved Apr. 11, 2016.
Wikipedia® entry for "Pioglitazone" Retrieved from the Internet: https://en.wikipedia.org/wiki/Pioglitazone pp. 1-3, retrieved Apr. 11, 2016.
Wikipedia® entry for "Standard deviation" Retrieved on Oct. 10, 2017, pp. 1-3.
Wikipedia® entry for "Stratified sampling" Retrieved on Mar. 28, 2017, pp. 1-4.
Wild et al., "Global prevalence of diabetes: estimates for the year 2000 and projections for 2030." Diabetes Care 27(5):1047-53 (May 2004).
Williams & Pickup, "Macrovascular disease in Diabetes." In handbook of Diabetes. 2nd ed. Williams G, Pickup JC, Eds. Oxford, UK, Blackwell Science Chapter 21; pp. 151-158 (1999).
Williams et al., "Macrovascular disease in Diabetes." In handbook of Diabetes. 2nd ed. Williams G, Pickup JC, Eds. Oxford, UK, Blackwell Science Chapter 20; pp. 152-160 (2010).
Wirths et al., "Intraneuronal Abeta accumulation precedes plaque formation in beta-amyloid precursor protein and presenilin-1 double-transgenic mice." Neurosci Lett. 306(1-2):116-20 (2001).
Wirths et al., "Intraneuronal APP/Aβ Trafficking and Plaque Formation in β-Amyloid Precursor Protein and Presenilin-1 Transgenic Mice" Brain Pathol. 12:275-286 (2002).
Wirths et al., "Reelin in plaques of beta-amyloid precursor protein and presenilin-1 double-transgenic mice." Neurosci Lett. 316(3):145-48 (2001).
Wiviott et al., "Greater Clinical Benefit of More Intensive Oral Antiplatelet Therapy With Prasugrel in Patients With Diabetes Mellitus in the Trial to Assess Improvement in Therapeutic Outcomes by Optimizing Platelet Inhibition With Prasugrel-Thrombolysis in Myocardial Infarction 38." Circulation 118(16):1626-36 (Oct. 2008; Epub Aug. 31, 2008).
Wohlfart et al., "Cardioprotective effects of lixisenatide in rat myocardial ischemia-reperfusion injury studies" Journal of Translational Medicine, 11(1):84, 12 pages (Mar. 2013).
Wolever et al., "Second-meal effect: low-glycemic-index foods eaten at dinner improve subsequent breakfast glycemic response." Am J Clin Nutr 48(4):1041-47 (Oct. 1988).
Wollen, Alzheimer's disease: the pros and cons of pharmaceutical, nutritional, botanical, and stimulatory therapies, with a discussion of treatment strategies from the perspective of patients and practitioners, Altern Med. Rev., 15:223-44 (2010).
World Health Organisation report on "Definition and diagnosis of diabetes mellitus and intermediate hyperglycemia: report of a WHO/IDF consultation" pp. 1-50 (2006).
World Health Organization, "Definition, Diagnosis and Classification of Diabetes Mellitus and its Complications. Part 1: Diagnosis and Classification of Diabetes Mellitus." WHO/NCD/NCS/99.2. Geneva; pp. 1-66, (1999).

Wright et al., U.K. Prospective Diabetes Study Group. "Sulfonylurea inadequacy: efficacy of addition of insulin over 6 years in patients with type 2 diabetes in the UK. Prospective Diabetes Study (UKPDS 57)." Diabetes Care 25(2):330-36 (Feb. 2002).
Written Opinion of the ISA for International Application No. PCT/EP2011/058079, mailed Mar. 22, 2012, pp. 1-8.
Xie et al., "Characterization of protein impurities and site-specific modifications using peptide mapping with liquid chromatography and data independent acquisition mass spectrometry." Anal Chem. 81(14):5699-708 (Jul. 2009).
Yki-Jarvinen et al., "Thiazolidinediones," N Engl J Med. 351(11):1106-18 (Sep. 2004).
Yki-Järvinen et al., "Comparison of Bedtime insulin regimes in patients with type 2 diabetes mellitus." Annals of Internal Medicine 130(5):389-96 (Mar. 1999).
Yki-Jarvinen et al., "Insulin glargine or NPH combined with metformin in type 2 diabetes: the Lanmet study." Diabetologia 49(3):442-51 (Mar. 2006).
Yki-Järvinen, "Combination Therapies with insulin in type 2 diabetes." Diabetes Care 24(4):758-67 (Apr. 2001).
Yoon et al., "Exenatide added to insulin therapy: a retrospective review of clinical practice over two years in an academic endocrinology outpatient setting." Clinical Therapeutics 31(7):1511-23 (2009).
Yu et al., "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32 (4):273-78 (2005). Abstract only.
Yusuf et al., "Effects of clopidogrel in addition to aspirin in patients with acute coronary syndromes without ST-segment elevation." N Engl J Med 345(7):494-502 (Aug. 2001).
Zealand Pharma Company Announcement "Zealand Pharma, Additional positive results from Global Phase III program with -3-lixisenatide for type 2 diabetes", Apr. 12, 2011, pp. 1-3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Zealand Pharma Press Release No. 3 entitled "Sanofi-Aventis finalize phase IIa clinical study with GLP-1 agonist for type 2 diabetes licensed from Zealand Pharma" dated Mar. 3, 2005, one page.
Zeitler et al., "ISPAD Clinical Practice Consensus Guidelines 2014. Type 2 diabetes in the child and adolescent." Pediatr Diabetes 15(Suppl 20):26-46 (Sep. 2014).
Ziemer et al., "Clinical inertia contributes to poor diabetes control in a primary care setting" The Diabetes Educ 31(4):564-71 (2005).
Ziessman et al., "Sincalide-stimulated cholescintigraphy: a multi-center investigation to determine optimal infusion methodology and gallbladder ejection fraction normal values." J Nucl Med. 51(2):277-81 (Feb. 2010).
Zimmet et al., "The metabolic syndrome in children and adolescents." Lancet 369(9579):2059-61 (Jun. 2007).
Zimmet et al., "Global and societal implications of the diabetes epidemic." Nature 414(6865):782-87 (Dec. 2001).
Zimmet, et al. "Clinical Efficacy of Metformin against Insulin Resistance Parameters, Sinking the Iceberg" Review Article, Drugs 1999: 58(Suppl 1):21-28 (Sep. 1999).
Zinman "The Physiologic Replacement of Insulin," New England J. Med. 321(6):363-70 (Aug. 1989).
Zinman et al., "Efficacy and safety of the human glucagon-like peptide-1 analog liraglutide in combination with metformin and thiazolidinedione in patients with type 2 diabetes (LEAD-4 Met+ TZD)." Diabetes Care, 32(7):1224-30 (Jul. 2009).
Zinman et al., "The Effect of Adding Exenatide to a Thiazolidinedione in Suboptimally Controlled Type 2 Diabetes" Annals of Internal Medicine, 146(7):477-85 (Apr. 2007).
Zoungas et al., "Combined Effects of Routine Blood Pressure Lowering and Intensive Glucose Control on Macrovascular and Microvascular Outcomes in Patients With Type 2 Diabetes. New results from the Advance trial." Diabetes Care 32(11):2068-74 (Nov. 2009; Epub Aug. 3, 2009).

(56) References Cited

OTHER PUBLICATIONS

КоН дратвеВ В.А. МеТо ди уескди е уКазаНия , May 5, 2010,с. 5 (Kondrat'ev V.A. Methodical Guidelines, May 7, 2010, p. 5)], found on Mar. 24, 2016, found from Internet: StudFields.ru>preview/ 4510743), English Translation.

* cited by examiner

PHARMACEUTICAL COMPOSITION COMPRISING A GLP-1-AGONIST AND METHIONINE

RELATED APPLICATIONS

This application is a continuation of U.S. patent application Ser. No. 16/921,422, filed Jul. 6, 2020, which is a continuation of U.S. patent application Ser. No. 16/013,617, filed Jun. 20, 2018, which is a continuation of U.S. patent application Ser. No. 15/595,929, filed May 15, 2017, now U.S. Pat. No. 10,028,910, which is a continuation of U.S. patent application Ser. No. 13/509,507, filed Jul. 30, 2012, now U.S. Pat. No. 9,707,176, which is a 35 U.S.C. § 371 filing of International Patent Application No. PCT/EP2010/067249, filed Nov. 11, 2010, and which claims the benefit of priority to German Patent Application Nos. 102010011919.9, filed Mar. 18, 2010, and 102009052832.6, filed Nov. 13, 2009, the entire disclosures of which are hereby incorporated by reference herein.

The present application relates to a liquid composition comprising a GLP-1 agonist or/and a pharmacologically tolerable salt thereof and, optionally, at least one pharmaceutically acceptable excipient, wherein the composition comprises methionine.

The present application further relates to the composition according to the present invention for treating diabetes mellitus. The present application further relates to the use of a composition according to the present invention in the manufacture of a pharmaceutical for treating diabetes mellitus. The present application further relates to a method for manufacturing a composition according to the present invention, comprising formulating a GLP-1 agonist or/and a pharmacologically tolerable salt thereof with methionine and, optionally, at least one pharmaceutically acceptable excipient. The present application further relates to a method for treating a patient with a composition according to the present invention, comprising administering the composition to the patient.

Customary compositions of GLP-1 compounds comprise a tonicity modifier, a buffer for adjusting the pH, and a preservative.

WO2001/04156 (Zealand Pharmaceuticals) discloses a liquid composition of Ser$^{39}$-exendin-4(1-39)-NH$_2$), sodium dihydrogenphosphate, and preservatives.

WO 2004/035623 (Zealand Pharmaceuticals) discloses a liquid composition comprising a stabilized exendin, 50 mM histidine, 100 to 200 mM sucrose, mannitol or other acceptable sugar, 20 mM methionine, 20 mM asparagine-glutamine or Asp, at a pH of 5.3. Stabilization is effected by certain modifications of the amino acid building blocks of exendin-4(1-39), for example, at positions Gln13, Met14, Trp25, or Asn28.

WO 2005/021022 (Novo Nordisk) discloses a liquid composition comprising acetylated GLP-1, phenol as a preservative, mannitol and glycerol as a tonicity modifier, and, optionally, a buffer.

WO 2006/051110 (Novo Nordisk) discloses liquid compositions comprising liraglutide (GLP-1 compound), poloxamer 188 or poloxamer 407 (Pluronic F-127) as a surface-active substance, phenol, propylene glycol, and sodium phosphate (pH 7.7). Addition of poloxamer-188 or poloxamer-407 led to stabilization.

Exendins are a group of peptides which can lower blood glucose concentrations. Exendins have a certain similarity to the sequence of GLP-1(7-36) (53%, Goke et al. J. Biol Chem 268, 19650-55). Exendin-3 and exendin-4 stimulate an increase in cellular cAMP production in the acinar cells of the guinea pig pancreas by interacting with exendin receptors (Raufman, 1996, Reg. Peptides 61:1-18). Exendin-3, in contrast to exendin-4, effects an increase in the release of amylase in the acinar cells of the pancreas. Exendins act as GLP-1 agonists.

Glucagon-like peptide 1 (GLP-1) is an endocrine hormone which enhances the insulin response following oral intake of glucose or fat. In general, GLP-1 lowers glucagon concentrations, slows gastric emptying, stimulates (pro) insulin synthesis, enhances sensitivity to insulin, and stimulates insulin-independent glycogen synthesis (Hoist (1999), Curr. Med. Chem 6:1005, Nauck et al. (1997) Exp Clin Endocrinol Diabetes 105: 187, Lopez-Delgado et al. (1998) Endocrinology 139:2811). Human GLP-1 has 37 amino acid residues (Heinrich et al., Endocrinol. 115:2176 (1984), Uttenthal et al., J Clin Endocrinol Metabol (1985) 61:472). Active fragments of GLP-1 include GLP-1 (7-36) and GLP-1(7-37).

Exendin-3, exendin-4 and exendin agonists have been proposed for treating diabetes mellitus and preventing hyperglycemia, by reducing gastric motility and gastric emptying (U.S. Pat. No. 5,424,286 and WO98/05351).

Exendin analogs can be characterized by amino acid substitutions and/or C-terminal truncation of the native exendin-4 sequence. Such exendin analogs are described in WO 99/07404, WO 99/25727, and WO 99/25728.

Solid-phase synthesis of AVE0010 is described in WO 01/04156 A1. AVE0010 has the sequence: desPro$^{36}$exendin-4(1-39)-Lys$_6$-NH$_2$. This substance is published as SEQ ID NO:93 in WO 01/04156:

```
                                        (SEQ ID NO: 1)
H-G-E-G-T-F-T-S-D-L-S-K-Q-M-E-E-E-A-V-R-L-F-I-E-W-

L-K-N-G-G-P-S-S-G-A-P-P-S-K-K-K-K-K-K-NH₂
```

Exendin-4 (39 AS) has the Sequence:

```
                                        (SEQ ID NO: 2)
H-G-E-G-T-F-T-S-D-L-S-K-Q-M-E-E-E-A-V-R-L-F-I-E-W-

L-K-N-G-G-P-S-S-G-A-P-P-P-S-NH₂
```

Exendin-3 has the Sequence (J. Bio. Chem., 267, 1992, 7402-7405):

```
                                        (SEQ ID NO: 3)
H-His-Ser-Asp-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-NH₂
```

GLP-1 has the Sequence:

```
                                        (SEQ ID NO: 4)
H-A-E-G-T-F-T-S-D-V-S-S-Y-L-E-G-Q-A-A-K-E-F-I-A-W-

L-V-K-G-R-NH₂
```

It is an object of the present invention to Increase the stability of liquid formulations comprising a GLP-1 agonist. More particularly, it is an object of the present invention to improve physical and chemical integrity. We have found that this object is achieved by formulating the GLP-1 agonist with methionine.

It was found that methionine is able to increase the storage stability of a composition comprising a GLP-1 agonist such as AVE0010. Methionine does not affect the physical integrity of these compositions.

It was found that, surprisingly, the addition of methionine is able to improve the storage stability of a composition according to the present invention by reducing the proportion of oxidation products of methionine, of proteins of high molecular weight, and of total impurities. These parameters are, individually or together, a measure of the chemical integrity of the compositions.

It was further found that, surprisingly, the biological activity of the compositions according to the present invention is increased by the addition of methionine.

The stability of pharmaceutically active polypeptides can be impaired by various mechanisms. These include pH, temperature, light, and the effects of certain constituents.

A range of customary constituents of formulations of GLP-1 agonists can be disadvantageous for the chemical or/and physical integrity and the storage stability of formulations which comprise a GLP-1 agonist. These are, for example, polysorbate 20, polysorbate 80, poloxamer 188, benzalkonium chloride, and lysine. The compositions according to the present invention are therefore preferably free of these constituents.

The present invention accordingly provides for a liquid composition comprising a GLP-1 agonist or/and a pharmacologically tolerable salt thereof and, optionally, at least one pharmaceutically acceptable excipient, wherein the composition comprises methionine.

The composition according to the present invention preferably comprises methionine in an amount ranging from 0.5 mg/mL to 20 mg/mL, more preferably in an amount ranging from 1 mg/mL to 5 mg/mL. Methionine in the D-form can be used. Likewise, methionine in the L-form can be used. Likewise, mixtures of the D-form and the L-form in any desired proportions can be used.

More particularly, the composition according to the present invention is free of surfactants, such as polyols and partial and fatty acid esters and ethers of polyhydric alcohols such as those of glycerol and sorbitol. The compositions according to the present invention are more particularly free of partial and fatty acid esters and ethers of glycerol and sorbitol selected from the group consisting of Span®, Tween®, Myrj®, Brij®, Cremophor®. Furthermore, the compositions according to the present invention are more particularly free of polyols selected from the group consisting of polypropylene glycols, polyethylene glycols, poloxamers, Pluronics, Tetronics. More particularly, the composition according to the present invention is free of at least one substance selected from the group consisting of polysorbate, polysorbate and poloxamer.

More particularly, the composition according to the present invention is substantially free, preferably free, of polysorbate, such as, for example, polysorbate 20.

More particularly, the composition according to the present invention is substantially free, preferably free, of polysorbate 80.

More particularly, the composition according to the present invention is substantially free, preferably free, of poloxamer, such as, for example, poloxamer 188.

More particularly, the composition according to the present invention is substantially free, preferably free, of benzalkonium chloride.

More particularly, the composition according to the present invention is substantially free, preferably free, of histidine.

More particularly, the composition according to the present invention is substantially free, preferably free, of EDTA, more particularly sodium EDTA.

The composition according to the present invention can comprise one or more substances which are customarily used to buffer the pH (buffer substances).

Examples of such buffer substances are acetate, citrate, and phosphate, for example, in amounts of up to 5 mg/ml, up to 4 mg/ml, up to 3 mg/ml, or up to 2 mg/ml.

The composition according to the present invention can, likewise, be substantially free of buffer substances. Likewise, the composition according to the present invention can be free of buffer substances.

The composition according to the present invention can be substantially free of citrate, acetate, and/or phosphate, or else free of citrate, acetate, and/or phosphate.

More particularly, the composition according to the present invention is substantially free, preferably free, of histidine and sodium EDTA.

More particularly, no insulin is present in the composition according to the present invention.

The pharmaceutical composition of the present invention can have an acidic or physiological pH. An acidic pH range is preferably in the range of pH 1-6.8, pH 3.5-6.8, or pH 3.5-5. A physiological pH is preferably in the range of pH 2.5-8.5, more preferably pH 4.0 to 8.5, even more preferably pH 4.0 to 6.0. Especially preferred is a pH of approximately 4.5. For pH adjustment, physiologically safe dilute acids (typically HCl) and alkalis (typically NaOH) are suitable.

The composition according to the present invention can comprise a suitable preservative. Suitable preservatives are, for example, phenol, m-cresol, benzyl alcohol, and/or p-hydroxybenzoate esters. m-Cresol is preferred.

Furthermore, the composition according to the present invention can comprise suitable tonicity modifiers. Suitable tonicity modifiers are, for example, glycerol, dextrose, lactose, sorbitol, mannitol, glucose, NaCl, calcium or magnesium compounds such as $CaCl_2$ etc. The concentrations of glycerol, dextrose, lactose, sorbitol, mannitol, and glucose are customarily in the range of 100-250 mM, NaCl in a concentration of up to 150 mM. Glycerol is preferred.

More particularly, the composition is intended for parenteral administration. The composition according to the present invention is preferably an injectable composition, more preferably for subcutaneous injection. More particularly, the composition of the present invention is suitable for injection once a day.

More particularly, the formulation according to the present invention has, after storage for 1 month, 2 months, 4 months, or 6 months at a temperature of +5° C. or 25° C., an activity of at least 80%, at least 90%, at least 95%, or at least 98% of the activity at the start of storage.

In the present application, "activity" means the activity of the GLP-1 agonist which is used in the formulation according to the present invention. Methods for determining the activity of a GLP-1 agonist are known to a person skilled in the art.

Preferably, the composition according to the present invention has a biological activity of GLP-1 agonist of at least 89% or at least 90% after storage for 6 months at 25° C. The composition according to the present invention preferably has a biological activity of GLP-1 agonist of at least 45% or at least 50% after storage for 6 months at 40° C.

More particularly, the formulation according to the present invention exhibits chemical integrity after storage for 1 month, 2 months, 3 months, 4 months, or 6 months. Chemical integrity means, more particularly, that after storage at a temperature of +5° C., 25° C., or 40° C. the formulation comprises at least 80%, at least 90%, at least 95%, or at least 98% of the active substance, compared with the start of storage, in a substantially chemically unchanged form.

Chemical integrity can mean the chemical integrity of the GLP-1 agonist. GLP-1 agonists may comprise a methionine residue (e.g. position 14 in AVE0010). Chemical Integrity of the GLP-1 agonist means, more particularly, that oxidation of the methionine residue is prevented. Here, chemical integrity means, more particularly, that the proportion of oxidized methionine with respect to the entire methionine content of the GLP-1 agonist after storage for 1, 2, 3, 4, or 6 months is below 0.7%, below 0.6%, below 0.5%, below 0.4%, or below 0.3%. Storage can be effected, for example, at 5° C., 25° C., or 40° C. Storage for 6 months at 5° C. is preferred, in which case the proportion of oxidized methionine is below 0.3%. Likewise, storage for 6 months at 25° C. is preferred, in which case the proportion of oxidized methionine is below 0.7%, below 0.6%, below 0.5%, below 0.4%, or below 0.3%. Likewise, storage for 6 months at 40° C. is preferred, in which case the proportion of oxidized methionine is below 1%, below 0.7%, below 0.6%, below 0.5%, below 0.4%, or below 0.3%.

Chemical integrity can mean a very low proportion of total impurities in the formulation according to the present invention. The proportion of total impurities with respect to the entire mass of the GLP-1 agonist present in the formulation after storage for 6 months at 40° C. is more particularly below 50%, below 10% after storage at 25° C., or/and below 1.8% after storage at 5° C.

Chemical integrity can mean a very low proportion of proteins of high molecular weight in the formulation according to the present invention. The proportion of proteins of high molecular weight with respect to the entire mass of the GLP-1 agonist present in the formulation after storage for 6 months at 40° C. is more particularly below 5%, below 4%, below 3%, or below 2%. After storage for 6 months at 25° C., the proportion of proteins of high molecular weight with respect to the entire mass of the GLP-1 agonist present in the formulation is more particularly below 0.8%, below 0.7%, or below 0.6%.

More particularly, the formulation according to the present invention exhibits physical integrity after storage for 1 month, 2 months, 4 months, or 6 months. Physical integrity means, more particularly, that after storage at a temperature of +5° C., 25° C., or 40° C. the formulation comprises at least 80%, at least 90%, at least 95%, or at least 98% of the active substance, compared with the start of storage, in a substantially physically unchanged form.

Physical integrity can mean the integrity of the GLP-1 agonist. Physical integrity means, more particularly, that the GLP-1 agonist does not form aggregates, such as, for example, fibrils.

The GLP-1 agonist is preferably selected from the group consisting of exendin-3 and analogs and derivates thereof, exendin-4 and analogs and derivates thereof, and in which case the GLP-1 agonist is more preferably selected from the group consisting of AVE0010 and exendin-4.

Exendin-3, analogs and derivates of exendin-3, exendin-4, and analogs and derivates of exendin-4 can be found in WO 01/04156, WO 98/30231, U.S. Pat. No. 5,424,286, EP application 99 610043.4, and WO 2004/005342. These documents are incorporated herein by reference. The exendin-3, exendin-4, and analogs and derivates thereof described in these documents can be synthesized by means of the methods described therein, after which modifications are optionally carried out.

The sequences of AVE0010 (SEQ ID NO:1), exendin-4 (SEQ ID NO:2), and exendin-3 (SEQ ID NO:3) show a high degree of similarity. The sequences of AVE0010 and exendin-4 are identical at positions 1-37. Sequence 1-39 from exendin-4 is at 37 of the 39 positions (94%) identical to the exendin-3 sequence at positions 48-86. With reference to the sequences, a person skilled in the art can readily convert the positions specified herein, which relate to a particular sequence (e.g. to the sequence of AVE0010 or exendin-4), to other sequences.

Analogs and derivates of exendin-3 or/and exendin-4 contain more particularly a modified amino acid sequence. For example, single amino acids can be deleted (e.g. desPro36, desPro37, desAsp28, desMet(O)14 in exendin-4 and the corresponding positions in exendin-3). Likewise, single positions can be substituted (e.g. Met(O)$^{14}$, Trp(O$_2$)$^{25}$, IsoAsp$^{28}$, Asp$^{28}$ Pro$^{38}$ in exendin-4 and the corresponding positions in exendin-3), in which case unnatural amino acids such as Met(O) (methionine sulfoxide or methionine sulfone), Trp(O$_2$) (N-formylkynurenine), or/and IsoAsp (p-aspartate or isoaspartate) can also be used. Unnatural amino acids can be readily inserted, in the form of corresponding amino acid building blocks, into the sequence.

Furthermore, the C-terminus or/and the N-terminus can be modified, for example, by an additional sequence such as -(Lys)-, -(Lys)$_2$-, -(Lys)$_3$-, -(Lys)$_4$-, -(Lys)$_5$-, -(Lys)$_6$-, -Asn-(Glu)$_5$-, in which case -(Lys)$_4$-, -(Lys)$_5$-, -(Lys)$_6$-, -Asn-(Glu)$_5$- are preferred. The carboxyl group at the C-terminus is preferably modified to an amide group (—NH$_2$). Optionally, modification of the C-terminus or/and of the N-terminus is carried out as a further step after completion of synthesis.

Pharmaceutically tolerable salts can be manufactured in a further step after completion of the synthesis cycles of the method according to the present invention. The manufacture of pharmaceutically tolerable salts of peptides is known to a person skilled in the art. A preferred pharmaceutically tolerable salt is acetate.

The GLP-1 agonist is preferably selected from the group consisting of exendin-4, analogs and derivates of exendin-4, and pharmacologically tolerable salts thereof.

A further preferred GLP-1 agonist is an analog of exendin-4 selected from the group consisting of:
H-desPro$^{36}$-exendin-4-Lys$_6$-NH$_2$,
H-des(Pro$^{36,37}$)-exendin-4-Lys$_4$-NH$_2$,
H-des(Pro$^{36,37}$)-exendin-4-Lys$_5$-NH$_2$ and pharmacologically tolerable salts thereof.

A further preferred GLP-1 agonist is an analog of exendin-4 selected from the group consisting of:
desPro$^{36}$[Asp$^{28}$]exendin-4 (1-39),
desPro$^{36}$[IsoAsp$^{28}$]exendin-4 (1-39),
desPro$^{36}$[Met(O)$^{14}$,Asp$^{28}$]exendin-4 (1-39),
desPro$^{36}$[Met(O)$^{14}$,IsoAsp$^{28}$]exendin-4 (1-39),
desPro$^{36}$[Trp(O$_2$)$^{25}$,Asp$^{28}$]exendin-2 (1-39),
desPro$^{36}$[Trp(O$_2$)$^{25}$,IsoAsp$^{28}$]exendin-2 (1-39),
desPro$^{36}$[Met(O)$^{14}$Trp(O$_2$)$^{25}$,Asp$^{28}$]exendin-4 (1-39),
desPro$^{36}$[Met(O)$^{14}$Trp(O$_2$)$^{25}$,IsoAsp$^{28}$]exendin-4(1-39) and pharmacologically tolerable salts thereof.

A further preferred GLP-1 agonist is an analog of exendin-4 selected from a group as described in the previous paragraph, wherein the peptide -Lys$_6$-NH$_2$ is attached to the C-termini of the analogs of exendin-4.

A further preferred GLP-1 agonist is an analog of exendin-4 selected from the group consisting of:

H-(Lys)$_6$-desPro$^{36}$[Asp$^{28}$]exendin-4(1-39)-Lys$_6$-NH$_2$,
desAsp$^{28}$Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Asp$^{28}$]exendin-4(1-39)-NH$_2$,
H-Asn-(Glu)$_5$desPro$^{36}$,Pro$^{37}$,Pro$^{38}$[Asp$^{28}$]exendin-4(1-39)-NH$_2$,
desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$,Pro$^{37}$, Pro$^{38}$[Asp$^{28}$]exendin-4(1-39)-(Lys)$_6$-NH$_2$,
H-Asn-(Glu)$_5$-desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$[Trp(O$_2$)$^{25}$,Asp$^{28}$]exendin-4(1-39)-Lys$_6$-NH$_2$,
H-desAsp$^{28}$ Pro$^{36}$,Pro$^{37}$,Pro$^{38}$[Trp(O$_2$)$^{25}$]exendin-4(1-39)-NH$_2$,
H-(Lys)$_6$-desPro$^{36}$,Pro$^{37}$,Pro$^{38}$[Trp(O$_2$)$^{25}$,Asp$^{28}$]exendin-4(1-39)-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-NH$_2$,
desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$[Met(O)$^{14}$,Asp$^{28}$]exendin-4(1-39)-Lys$_6$-NH$_2$,
desMet(O)$^{14}$ Asp$^{28}$ Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Met(O)$^{14}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$] exendin-4(1-39)-NH$_2$,
desPro$^{36}$, Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Asp$^{28}$]exendin-4(1-39)-Lys$_6$-NH$_2$,
H-Asn-(Glu)$_5$-desPro$^{36}$,Pro$^{37}$,Pro$^{38}$[Met(O)$^{14}$,Asp$^{28}$] exendin-4(1-39)-(Lys)$_6$-NH$_2$,
H-(Lys)$_6$-desPro$^{36}$[Met(O)$^{14}$, Trp(O$_2$)$^{25}$,Asp$^{28}$]exendin-4(1-39)-Lys$_6$-NH$_2$,
desAsp$^{28}$Pro$^{36}$,Pro$^{37}$,Pro$^{38}$[Met(O)$^{14}$, Trp(O$_2$)$^{25}$]exendin-4(1-39)-NH$_2$,
H-(Lys)$_6$-desPro$^{36}$,Pro$^{37}$,Pro$^{38}$[Met(O)$^{14}$, Trp(O$_2$)$^{25}$,Asp$^{28}$] exendin-4(1-39)-NH$_2$
H-Asn-(Glu)$_5$-desPro$^{36}$,Pro$^{37}$,Pro$^{38}$[Met(O)$^{14}$,Asp$^{28}$] exendin-4(1-39)-NH$_2$,
desPro$^{36}$,Pro$^{37}$,Pro$^{38}$[Met(O)$^{14}$, Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Trp(O$_2$)$^{25}$,Asp$^{28}$] exendin-4(1-39)-(Lys)$_6$-NH$_2$,
H-Asn-(Glu)$_5$-desPro$^{36}$, Pro$^{37}$,Pro$^{38}$[Met(O)$^{14}$,Trp(O$_2$)$^{25}$, Asp$^{28}$]exendin-4(1-39)-(Lys)$_6$-NH$_2$ and pharmacologically tolerable salts thereof.

Likewise, the GLP-1 agonist can be selected from the group consisting of GLP-1 and analogs and derivates of GLP-1. A further preferred GLP-1 agonist is selected from the group consisting of Arg$^{34}$,Lys$^{26}$(N$^E$(γ-glutamyl(N$^\alpha$-hexadecanoyl)))GLP-1(7-37) [liraglutide] and a pharmacologically tolerable salt thereof.

A further preferred GLP-1 agonist is AVE0010. AVE0010 has the sequence desPro$^{36}$exendin-4(1-39)-Lys$_6$-NH$_2$ (SEQ ID NO:1). Likewise, pharmacologically tolerable salts of AVE0010 are preferred.

The GLP-1 agonist, for example AVE0010, is more particularly used in an amount ranging from 0.01 mg/mi to 0.5 mg/mi or 0.05 mg/mi to 1.5 mg/ml.

In a particular embodiment, the formulation according to the present invention comprises the following constituents:
(a) desPro$^{36}$exendin-4(1-39)-Lys$_6$-NH$_2$ (e.g. approximately 0.1 mg/mL),
(b) sodium acetate trihydrate (approximately 3.5 mg/mL),
(c) m-cresol (approximately 2.7 mg/mL),
(d) L-methionine (approximately 3 mg/mL),
(e) 85% glycerol (approximately 18 mg/mL),
(f) approximately 0.1 N hydrochloric acid, if adjustment to a pH of approximately 4.5 is required,
(g) approximately 0.1 N NaOH solution, if adjustment to a pH of approximately 4.5 is required, and
(h) water.

More particularly, the formulation according to the present invention consists of the constituents mentioned in (a) to (h).

In the present application, "approximately" means that the constituents can be present, for example, within the ranges of ±10, ±20, or ±30% around the specified values in the compositions according to the present invention.

If the composition according to the present invention comprises more than one GLP-1 agonist, then these GLP-1 agonists are selected independently of one another.

Suitable packaging for the composition according to the present invention is, for example, a syringe or a glass vessel with a suitable closure, from which individual therapeutically effective doses can be withdrawn as needed. Equally suitable are injection pens for administering doses; such pens comprise a container (e.g. a cartridge) which contains a pharmaceutical composition according to the present invention.

The present invention further provides for a method for treating a patient with a composition according to the present invention, comprising administering the composition to the patient.

The composition according to the present invention is intended more particularly for treating diabetes mellitus, more particularly for treating type I or type II diabetes mellitus. Further possible indications are symptoms which are associated with diabetes mellitus. Preferably, the composition according to the present invention is used to control the fasting, postprandial, or/and postabsorptive plasma glucose concentration, to improve glucose tolerance, to prevent hypoglycemia, to prevent functional loss of the β-cells of the pancreas, to effect weight loss, or/and to prevent weight gain.

The present invention further provides for the use of a composition according to the present invention in the manufacture of a pharmaceutical for treating diabetes mellitus, more particularly type I or type II, or/and the symptoms associated with it, as described herein.

The present invention further provides a method for manufacturing a composition according to the present invention, comprising formulating a GLP-1 agonist or/and a pharmacologically tolerable salt thereof with methionine and, optionally, at least one pharmaceutically acceptable excipient.

The present invention further provides for the use of the composition according to the present invention together with the administration of metformin, sulfonylurea, or glitazones, a long-acting insulin/insulin derivate, and/or a combination thereof, more particularly as an add-on therapy in the administration of metformin.

The present invention further provides for the use of the composition according to the present invention in patients whose blood sugar levels cannot be controlled sufficiently by the administration of metformin, sulfonylurea, or glitazones, a long-acting insulin/insulin derivate, and/or a combination thereof.

The present invention further provides for the use of the composition according to the present invention in patients with type II diabetes as a supplement to a diet in order to improve blood sugar control.

More particularly, the composition comprises desPro$_{36}$ exendin-4(1-39)-Lyse-NH$_2$ (AVE0010), liraglutide and/or a pharmacologically tolerable salt together with methionine and/or a pharmacologically tolerable salt.

More particularly, Lantus*, N$^{\epsilon B29}$-tetradecanoyl des (B30) human insulin, or Insuman® is useful as a long-acting insulin derivative.

Especially preferred is the add-on therapy with metformin and/or a long-acting insulin/insulin derivate and/or a pharmacologically tolerable salt thereof for treating type II diabetes and/or obesity, more particularly in patients who are younger than 50 years and/or have a body mass index of at least 30.

In the present invention, the add-on therapy involves more particularly the treatment of type II diabetes with metformin and AVE0010. Metformin and AVE0010 can be administered in a time interval of 24 hours. Metformin and AVE0010 can each be administered in a once-a-day dosage. Metformin and AVE0010 can be administered by means of different routes of administration. Metformin can be administered orally, AVE0010 subcutaneously.

Patients treated with the add-on therapy according to the present invention can have an HbA1c value in the range of 7% to 10%. They are preferably in the age range of 18 to 50 years.

The use in the add-on therapy according to the present invention is more particularly applicable to patients in whom type II diabetes cannot be sufficiently controlled with metformin alone.

More particularly, metformin is administered as follows: at least 1.0 g/day, preferably at least 1.5 g/day for 3 months.

The invention is further elucidated by the following examples and figures.

LEGENDS

Figure 2:
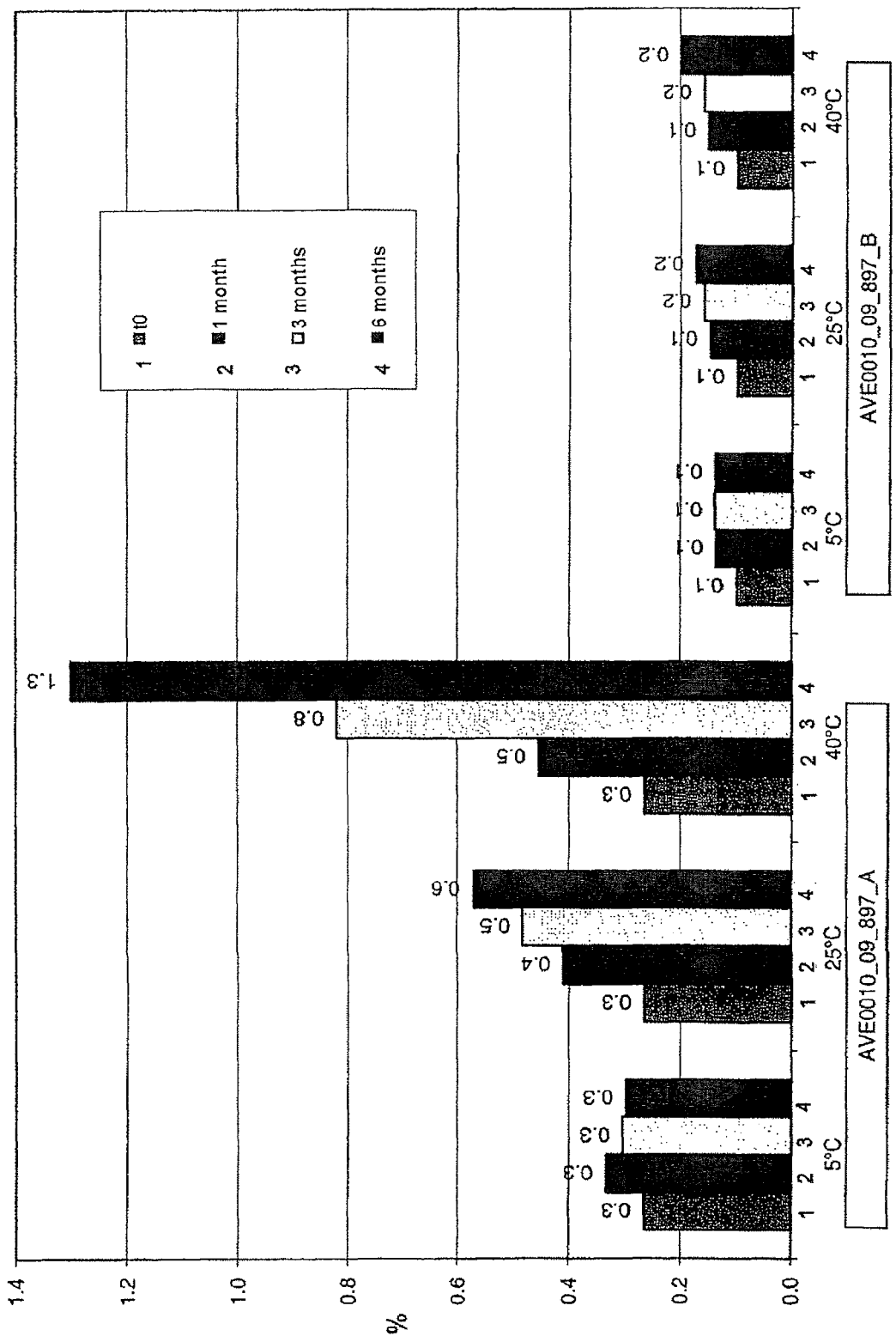

FIGS. 1 and 2 show the percentage content of oxidized methionine Met(ox) with respect to the entire methionine content of AVE0010 after storage at different temperatures. 1: start of storage t0. 2: storage for 1 month. 3: storage for 3 months. 3: storage for 6 months. FIG. 1: batch 894. FIG. 2: batch 897.

Figure 3:
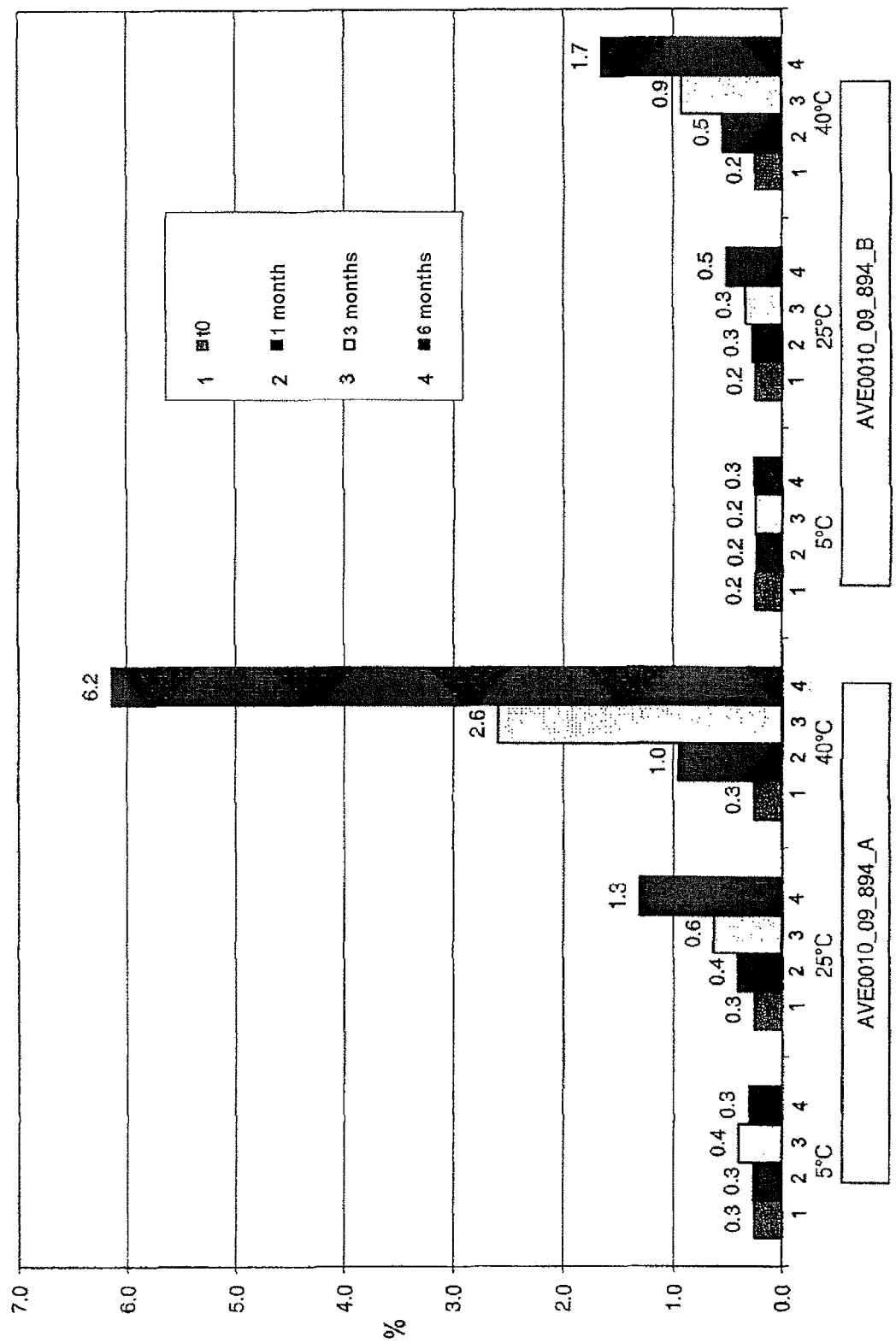
Figure 4:
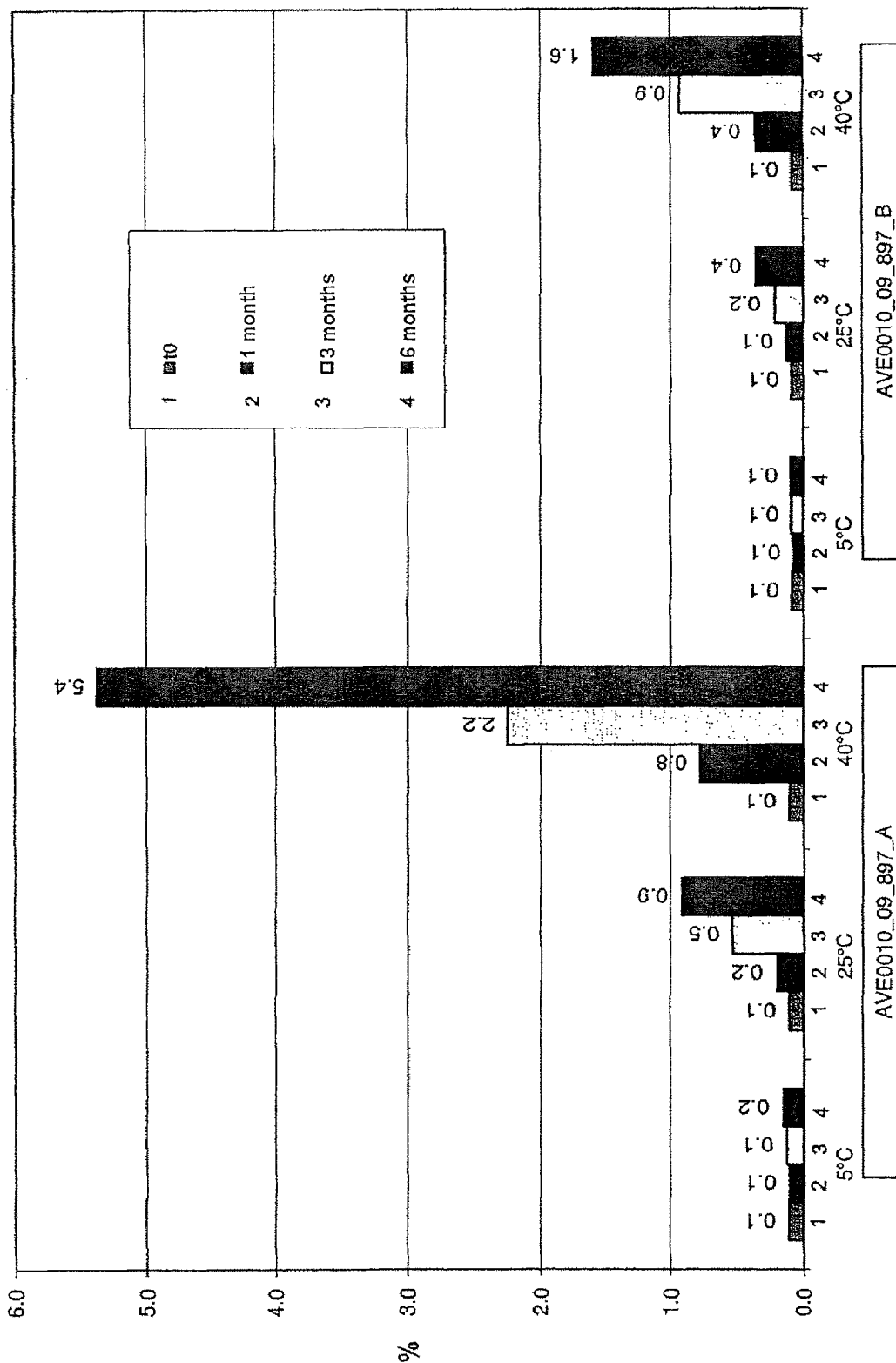

FIGS. 3 and 4 show the percentage content of protein impurities of high molecular weight (with respect to AVE0010) after storage at different temperatures. 1: start of storage t0. 2: storage for 1 month. 3: storage for 3 months. 3: storage for 6 months. FIG. 3: batch 894. FIG. 4: batch 897.

Figure 5:
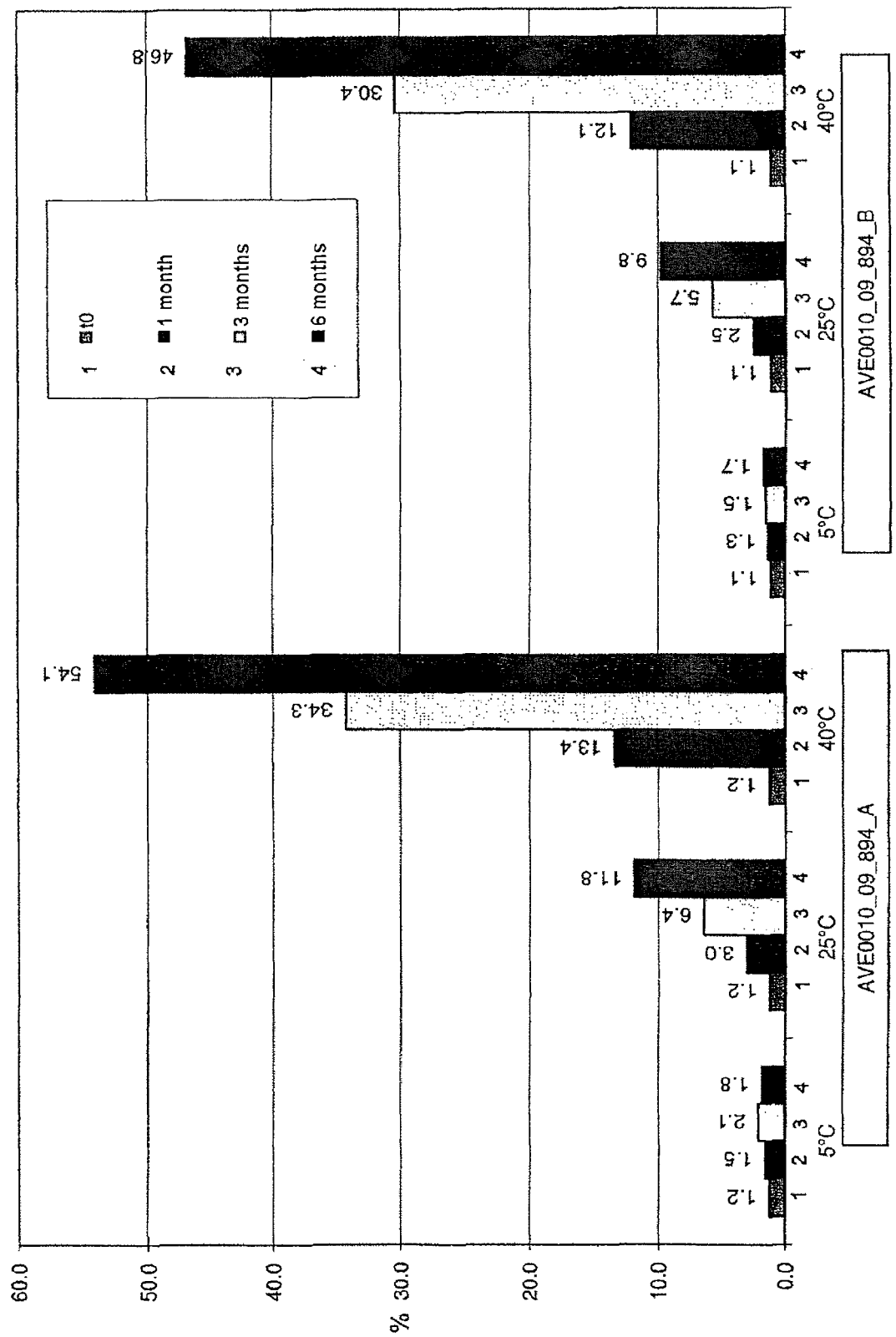
Figure 6:
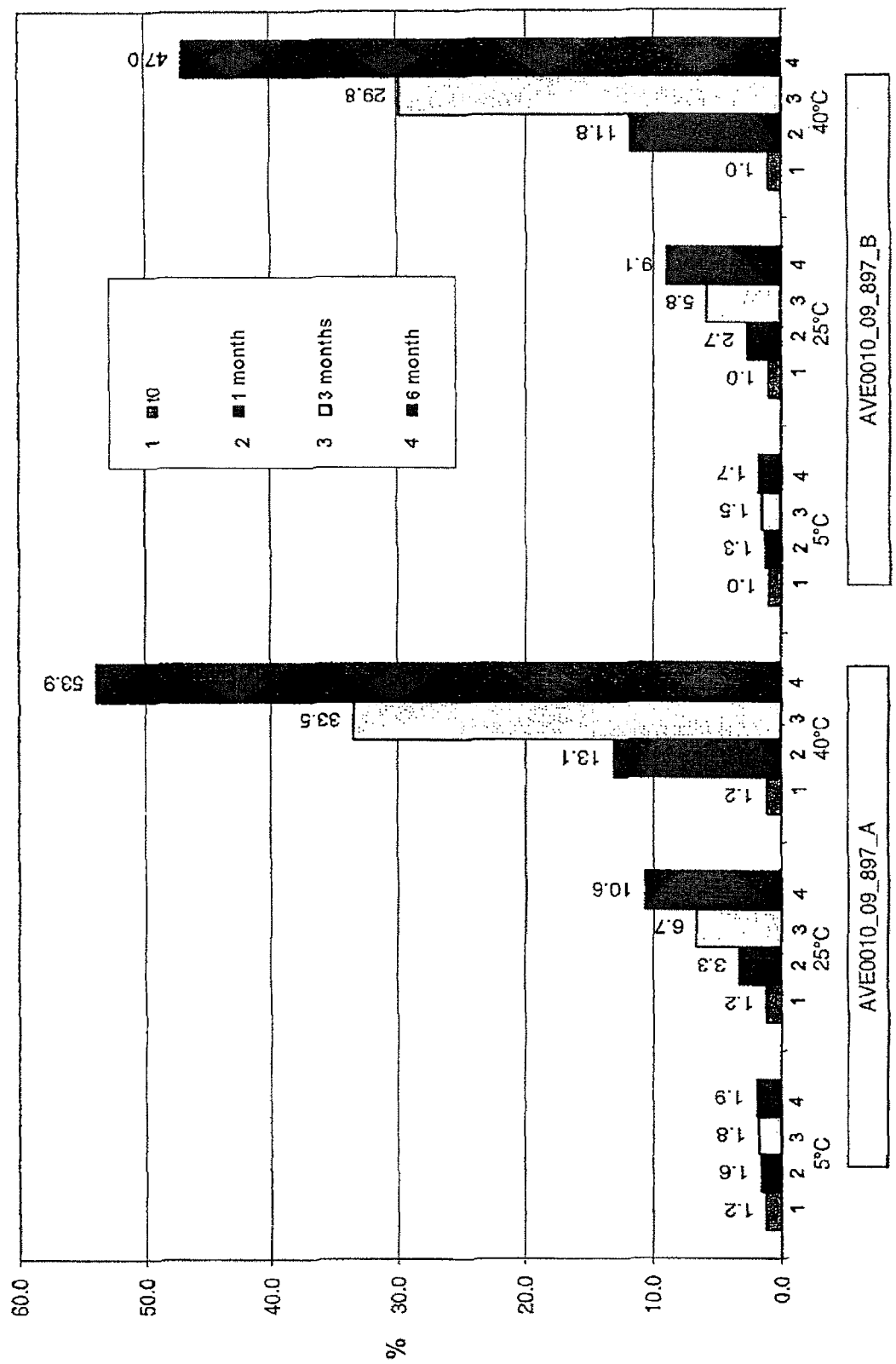

FIGS. 5 and 6 show the percentage content of all impurities (with respect to AVE0010) after storage at different temperatures. 1: start of storage t0. 2: storage for 1 month. 3: storage for 3 months. 3: storage for 6 months. FIG. 5: batch 894. FIG. 6: batch 897.

EXAMPLE 1

Liquid Composition Comprising AVE0010 and Methionine

The purpose of the study is the evaluation of the chemical or/and physical stability of formulations of AVE0010 (solution for injection, 0.1 mg/ml) with and without methionine, when the product is stored in cartridges under long-term conditions and accelerated conditions for up to 6 months.

The following compositions are tested:

Composition A (2 Parallel Batches: AVE0010_09_894_A and AVE0010_09_897_A)

| Substance | Specification according to pharmacopeia | Amount per unit |
|---|---|---|
| AVE0010 | Sanofi-Aventis | 0.10 mg |
| Sodium acetate trihydrate | Ph. Eur./USP | 3.50 mg |
| m-Cresol | Ph. Eur./USP | 2.70 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (Wfl) | Ph. Eur./USP | ad 1.0 ml |

Composition B (2 parallel batches: AVE0010_09_894_B and AVE0010_09_897_B

| Substance | Specification according to pharmacopeia | Amount per unit |
|---|---|---|
| AVE0010 | Sanofi-Aventis | 0.10 mg |
| Sodium acetate trihydrate | Ph. Eur./USP | 3.50 mg |
| m-Cresol | Ph. Eur./USP | 2.70 mg |
| L-Methionine | Ph. Eur./USP | 3.00 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (Wfl) | Ph. Eur./USP | ad 1.0 ml |

The formulations are stored in units which are intended for clinical studies and for sales and distribution.

| Term | Description |
|---|---|
| Cartridge for injection pen | Cartridge, 3 ml colorless, type I glass (Ph. Eur.), SAP number 100922 |
| Crimped lid and inserted within a gray sealing disk | 7.5 mm<br>Crimped lid: aluminum<br>Sealing disk (exterior): isoprene rubber, material number 7773/35<br>Sealing disk (interior): bromobutyl rubber, material number 4780/40<br>Type I closure (Ph. Eur./USP)<br>SAP number 164571 |
| Plunger | 9.2 × 11 mm<br>Bromobutyl rubber, black<br>SAP number 120521 |

Storage times, storage conditions, time points are summarized in the following table.

| | Test interval (months) | | | |
|---|---|---|---|---|
| Condition | 0 | 1 | 3 | 6 |
| Long-term storage | | | | |
| +5 ± 3° C. | x | x | x | x |
| Accelerated conditions (temperature, humidity) | | | | |
| +25 ± 2° C./60 ± 5% RH | | x | x | x |
| +40 ± 2° C./75 ± 5% RH | | x | x | x |

The formulations are stored horizontally. RH means relative humidity. Time point 0 is the start of storage. The measurements at time point 0 are used as a reference for all conditions tested. During the tests, the samples are stored at +5±3° C.

The physical and chemical stability of the stored formulations is determined with the help of the following tests:
Description
Clarity of the solution and color thereof
pH
Chemical stability (purity and impurities, determined by HPLC, more particularly the proportion of oxidation products and of total impurities)
Proteins of high molecular weight, determined by HPSEC
Visible particles
Biological activity of the formulations
Results The formulations were studied separately for the parallel batches (894 and 897) with regard to the following parameters:

Biological activity of AVE0010. At 5° C. and 25° C., activity after 6 months was at least 96% of initial activity. The activities of the compositions according to the present invention were greater than the activities of the comparative compositions. At 40° C., activity after 6 months in the absence of methionine was approximately 43%. In the presence of methionine, activity was approximately 51% and thus clearly greater than in the absence of methionine.

Oxidation products. Measurements were carried out on an HPLC instrument (model: alliance) from Water Systems, using the 100% peak area method. For separation, a gradient of 0.1% TFA and acetonitrile as the mobile phase and a C18 reversed-phase column (Jupiter) as the stationary phase were used. At 5° C., the proportion of oxidized methionine Met(ox) in AVE0010 in the absence of methionine was 0.3%. At 25° C., the proportion was in the range of 0.6-0.8%, at 40° C. 1.3%. When the formulation comprised methionine, the proportion of oxidized methionine was distinctly lower. It was never more than 0.2% under all conditions tested. At 25° C., the proportion was thus approximately only ¼ to ⅓ of the content in the absence of methionine, even at 40° C. approximately only ⅙ (see FIGS. 1 and 2).

Proteins of high molecular weight. At 5° C., the proportion was between 0.1 and 0.3% and remained substantially unchanged during the entire storage time. At 25° C., the proportion rose in the absence of methionine to 0.9 and 1.3%, respectively. In the presence of methionine, the proportion was 0.4 to 0.5% and thus less than half as high. At 40° C., the proportion was in the absence of methionine 5.4% and 6.2%, respectively, while it was in the presence of methionine only 1.6 and 1.7%, respectively, and thus clearly lower (see FIGS. 3 and 4).

Total Impurities. At 5° C., total impurities rose over the storage time of 6 months slightly from 1.2 to 1.8 or 1.9% (absence of methionine). When methionine was present, the rise was a little lower. At 25° C., a rise to 10.6% and 11.8%, respectively, was observed. In the presence of methionine, the values were below 10%. At 40° C., the proportion rose up to 54% (without methionine). When methionine was present, the proportion was approximately only 47% (see FIGS. 5 and 6).

The percentage values are the content values (percentage values of impurities) of the oxidation products, of total impurities, and of high-molecular-weight proteins (HMWP).

All values were determined by HPLC with the so-called 100% method. Here, in particular, it involves reversed-phase HPLC (C 18 column), in which a gradient method was used for the mobile phase:
a) 0.1% TFA, 15% ACN and b) 0.1% TFA, 75% ACN.
Detection at 215 nm (UV).

The high-molecular-weight proteins (HMWP) were detected by HPSEC, described in European Pharmacopeia 6.0 for injectable insulin preparations. The data are summarized in the following tables:

| Mean values: AVE0010_09_894_A + B | | | | | | | | |
|---|---|---|---|---|---|---|---|---|
| | AVE0010_09_894_A | | | | AVE0010_09_894_B | | | |
| | $t_0$ | 1 Mon. | 3 Mon. | 6 Mon. | $t_0$ | 1 Mon. | 3 Mon. | 6 Mon. |
| 5° C. | | | | | | | | |
| Total impurities | 1.2 | 1.5 | 2.1 | 1.8 | 1.1 | 1.3 | 1.5 | 1.7 |
| AVE0010 Test | 101.5 | 99.6 | 98.0 | 97.8 | 101.1 | 100.5 | 99.4 | 98.6 |
| Proteins of high molecular weight | 0.3 | 0.3 | 0.4 | 0.3 | 0.2 | 0.2 | 0.2 | 0.3 |
| Oxidation products | 0.3 | 0.4 | 0.4 | 0.3 | 0.1 | 0.2 | 0.1 | 0.1 |
| 25° C. | | | | | | | | |
| Total impurities | 1.2 | 3.0 | 6.4 | 11.8 | 1.1 | 2.5 | 5.7 | 9.8 |
| AVE0010 Test | 101.5 | 97.9 | 94.0 | 88.6 | 101.1 | 98.7 | 94.8 | 90.9 |
| Proteins of high molecular weight | 0.3 | 0.4 | 0.6 | 1.3 | 0.2 | 0.3 | 0.3 | 0.5 |
| Oxidation products | 0.3 | 0.4 | 0.5 | 0.8 | 0.1 | 0.2 | 0.2 | 0.2 |
| 40° C. | | | | | | | | |
| Total impurities | 1.2 | 13.4 | 34.3 | 54.1 | 1.1 | 12.1 | 30.4 | 46.8 |
| AVE0010 Test | 101.5 | 87.1 | 66.6 | 42.5 | 101.1 | 88.8 | 70.8 | 50.9 |
| Proteins of high molecular weight | 0.3 | 1.0 | 2.6 | 6.2 | 0.2 | 0.5 | 0.9 | 1.7 |
| Oxidation products | 0.3 | 0.6 | 0.9 | 1.3 | 0.1 | 0.2 | 0.2 | 0.2 |

| Mean values: AVE0010_09_897_A + B | | | | | | | | |
|---|---|---|---|---|---|---|---|---|
| | AVE0010_09_897_A | | | | AVE0010_09_897_B | | | |
| | $t_0$ | 1 Mon. | 3 Mon. | 6 Mon. | $t_0$ | 1 Mon. | 3 Mon. | 6 Mon. |
| 5° C. | | | | | | | | |
| Total impurities | 1.2 | 1.6 | 1.8 | 1.9 | 1.0 | 1.3 | 1.5 | 1.7 |
| AVE0010 Test | 99.2 | 98.2 | 97.5 | 96.7 | 99.5 | 99.2 | 98.0 | 97.1 |
| Proteins of high molecular weight | 0.1 | 0.1 | 0.1 | 0.2 | 0.1 | 0.1 | 0.1 | 0.1 |
| Oxidation products | 0.3 | 0.3 | 0.3 | 0.3 | 0.1 | 0.1 | 0.1 | 0.1 |
| 25° C. | | | | | | | | |
| Total impurities | 1.2 | 3.3 | 6.7 | 10.6 | 1.0 | 2.7 | 5.8 | 9.1 |
| AVE0010 Test | 99.2 | 96.6 | 92.8 | 87.4 | 99.5 | 97.8 | 93.6 | 90.0 |
| Proteins of high molecular weight | 0.1 | 0.2 | 0.5 | 0.9 | 0.1 | 0.1 | 0.2 | 0.4 |
| Oxidation products | 0.3 | 0.4 | 0.5 | 0.6 | 0.1 | 0.1 | 0.2 | 0.2 |
| 40° C. | | | | | | | | |
| Total impurities | 1.2 | 13.1 | 33.5 | 53.9 | 1.0 | 11.8 | 29.8 | 47.0 |
| AVE0010 Test | 99.2 | 86.8 | 66.5 | 42.6 | 99.5 | 88.0 | 70.7 | 51.0 |
| Proteins of high molecular weight | 0.1 | 0.8 | 2.2 | 5.4 | 0.1 | 0.4 | 0.9 | 1.6 |
| Oxidation products | 0.3 | 0.5 | 0.8 | 1.3 | 0.1 | 0.1 | 0.2 | 0.2 |

CONCLUSION

The proportion of oxidation products, of proteins of high molecular weight, and of total impurities are, individually or together, a measure of the chemical integrity of the compositions. From the results described above with the example compositions, it follows that the liquid compositions according to the present invention comprising

- a GLP-1 agonist or/and a pharmacologically tolerable salt thereof (more particularly AVE0010 or/and a pharmacologically tolerable salt thereof),
- optionally at least one pharmaceutically acceptable excipient,
- and methionine have improved stability or/and chemical integrity. The proportion of oxidized methionine, of total impurities, and of proteins of high molecular weight is lower in the compositions according to the present invention than in the comparative compositions. The composition according to the present invention (batches 894_B and 897_B) and the comparative compositions (batches 894_A and 897_A) differ in the presence/absence of methionine. Therefore, improved stability or/and chemical integrity can be ascribed to the methionine constituent in the compositions according to the present invention.

EXAMPLE 2

In a further experiment, it was studied how sodium EDTA and histidine have an effect in a composition according to the present invention.

Composition B (as in Example 1)

| Substance | Specification according to pharmacopeia | Amount per unit |
|---|---|---|
| AVE0010 | Sanofi-Aventis | 0.10 mg |
| Sodium acetate trihydrate | Ph. Eur./USP | 3.50 mg |
| m-Cresol | Ph. Eur./USP | 2.70 mg |
| L-Methionine | Ph. Eur./USP | 3.00 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (WfI) | Ph. Eur./USP | ad 1.0 ml |

Composition C

| Substance | Specification according to pharmacopeia | Amount per unit |
|---|---|---|
| AVE0010 | Sanofi-Aventis | 0.10 mg |
| Sodium acetate trihydrate | Ph. Eur./USP | 3.50 mg |
| Sodium EDTA | Ph. Eur./USP | 1.00 mg |
| m-Cresol | Ph. Eur./USP | 2.70 mg |
| L-Methionine | Ph. Eur./USP | 3.00 mg |
| L-Histidine | Ph. Eur./USP | 3.10 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (WfI) | Ph. Eur./USP | ad 1.0 ml |

In a standard experimental design, rabbits were treated with composition B or C or a saline solution subcutaneously (s.c.) or intramuscularly (i.m.). In each case, half the rabbits were sacrificed after 24 hours or 120 hours in order to determine the acute or subacute effects of the administration histologically. Also, it was determined whether repair/regeneration of any changes occurred.

Following subcutaneous injection of composition C, the animals showed after 24 hours, in contrast to the saline control, a light to moderate inflammatory reaction in the subcutaneous connective tissue. After subcutaneous injection 120 hours earlier, a clear trend was observable for the observed changes to repair by a fibroblastic reaction. Thus, compatibility could still be rated as moderate (instead of as incompatible).

With composition B, the animals showed after subcutaneous injection no or minimal differences to the saline control (good compatibility).

After intramuscular injection of composition C, the animals exhibited muscular necrosis (multifocal or disseminated), clearly differing from the saline controls, in which only the site of injection was visible as a clearly circumscribed necrotic area.

With composition C, mineralization of the necrotic muscular tissue was observed after 120 hours, visible even in a necropsy of the animals. Although small or focal mineralization at various sites in rabbits is not unusual, the mineralization after injection of composition C was clearly associated with the necrotic areas. Thus, the reversibility of the lesions caused by the injection is more than questionable. Based on these findings, composition C after intramuscular injection in rabbits was rated as incompatible.

Composition B after intramuscular injection showed good compatibility (no or minimal differences to the saline control).

From these data, it follows that composition B, compared to composition C, had an improved compatibility in intramuscular or subcutaneous administration. Subcutaneous injection is the preferred route of administration for the compositions comprising a GLP-1 agonist, more particularly AVE0010, described in this application.

Thus, the compositions according to the present invention, which comprise a GLP-1 agonist, more particularly AVE0010, can be free of EDTA or/and histidine. Likewise, the compositions according to the present invention can be substantially free of EDTA and histidine.

The invention claimed is:

1. An aqueous liquid composition consisting essentially of:
   desPro$^{36}$exendin-4(1-39)-Lys$_6$-NH2 ("AVE0010") or a pharmacologically tolerable salt thereof at a concentration of about 0.025 mg/mL to about 0.1 mg/ml;
   insulin glargine or a pharmacologically tolerable salt thereof at a concentration of about 3.64 mg/ml;
   about 3 mg/mL L-methionine;
   about 2.7 mg/ml m-cresol;
   about 20 mg/mL 85% glycerol, and
   about 30 μg/mL zinc.

2. The aqueous liquid composition of claim 1, wherein the composition further consists essentially of hydrochloric acid and sodium hydroxide such that the composition has a pH of about 4.5.

3. An aqueous liquid composition consisting essentially of:
   about 33 μg desPro$^{36}$exendin-4(1-39)-Lys$_6$-NH2 ("AVE0010") or a pharmacologically tolerable salt thereof;
   about 100 units insulin glargine or a pharmacologically tolerable salt thereof;
   about 3 mg L-methionine;
   about 2.7 mg m-cresol;
   about 20 mg 85% glycerol;
   about 30 μg zinc, and
   water in a quantity sufficient for the volume of the composition to total about 1 mL.

4. The aqueous liquid composition of claim 3, wherein the composition further consists essentially of hydrochloric acid and sodium hydroxide such that the composition has a pH of about 4.5.

5. An aqueous liquid composition consisting essentially of:
   about 50 μg/mL or about 100 μg/mL desPro$^{36}$exendin-4(1-39)-Lys$_6$-NH2 ("AVE0010") or a pharmacologically tolerable salt thereof;
   about 9 mg/mL L-methionine;
   about 8.1 mg/ml m-cresol;
   about 54 mg/mL 85% glycerol;
   about 10.5 mg sodium acetate trihydrate, and
   water in a quantity sufficient for the volume of the composition to total about 1 mL.

6. The aqueous liquid composition of claim 5, wherein the composition further consists essentially of hydrochloric acid and sodium hydroxide such that the composition has a pH of about 4.5.

* * * * *

```
                        SEQUENCE LISTING

<160> NUMBER OF SEQ ID NOS: 4

<210> SEQ ID NO 1
<211> LENGTH: 44
<212> TYPE: PRT
<213> ORGANISM: Artificial Sequence
<220> FEATURE:
<223> OTHER INFORMATION: Synthetic peptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic peptide

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 4
<211> LENGTH: 30
<212> TYPE: PRT
<213> ORGANISM: Artificial Sequence
<220> FEATURE:
<223> OTHER INFORMATION: Synthetic peptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```